United States Patent
Osborne et al.

(10) Patent No.: US 11,826,538 B2
(45) Date of Patent: Nov. 28, 2023

(54) HUMIDIFICATION SYSTEM CONNECTIONS

(71) Applicant: Fisher & Paykel Healthcare Limited, Auckland (NZ)

(72) Inventors: Hamish Adrian Osborne, Auckland (NZ); James William Stanton, Auckland (NZ); Bruce Gordon Holyoake, Auckland (NZ); Stephen David Evans, Auckland (NZ); David Leon McCauley, Auckland (NZ); Nicholas James Michael McKenna, Auckland (NZ); Gareth Thomas McDermott, Auckland (NZ); Myfanwy Jane Antica Norton, Auckland (NZ); Gavin Walsh Millar, Auckland (NZ); Thomas Jacques Fernand Maeckelberghe, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 236 days.

(21) Appl. No.: 17/061,408

(22) Filed: Oct. 1, 2020

(65) Prior Publication Data
US 2021/0016076 A1 Jan. 21, 2021

Related U.S. Application Data

(63) Continuation of application No. 15/105,531, filed as application No. PCT/NZ2014/050024 on Dec. 19, 2014, now Pat. No. 10,828,482.
(Continued)

(51) Int. Cl.
*A61M 16/08* (2006.01)
*A61M 16/16* (2006.01)
(Continued)

(52) U.S. Cl.
CPC .......... *A61M 39/12* (2013.01); *A61M 16/021* (2017.08); *A61M 16/0816* (2013.01);
(Continued)

(58) Field of Classification Search
CPC ............ A61M 16/109; A61M 16/1095; A61M 16/0816; A61M 16/1085; H01R 13/005;
(Continued)

(56) References Cited

U.S. PATENT DOCUMENTS 485,127 A 10/1892 Lynch
1,154,259 A 9/1915 Light
(Continued)

FOREIGN PATENT DOCUMENTS

AU 1448473 9/1976
AU 2000071791 3/2001
(Continued)

OTHER PUBLICATIONS

US 10,426,912 B2, 10/2019, Buswell et al. (withdrawn)
(Continued)

*Primary Examiner* — Daniel J Colilla
(74) *Attorney, Agent, or Firm* — Knobbe Martens Olson & Bear, LLP

(57) ABSTRACT

A circuit connector for a humidification system, the system comprising a base unit configured to be engaged by a humidification chamber. The circuit connector comprises an inlet to fluidly connect to an outlet of the humidification chamber to receive humidified gases therefrom, an outlet to sealably connect to or integral with a conduit for directing the humidified gases to a user, and an electrical terminal for electrically coupling the circuit connector to an electrical terminal associated with the base unit. The circuit connector may be releasably and lockably connectable to the outlet of the humidification chamber and/or orientation features may
(Continued)

control orientation of component parts of the system as they are assembled.

20 Claims, 36 Drawing Sheets

Related U.S. Application Data

(60) Provisional application No. 62/059,339, filed on Oct. 3, 2014, provisional application No. 61/919,485, filed on Dec. 20, 2013.

(51) Int. Cl.
*A61M 39/12* (2006.01)
*A61M 16/10* (2006.01)
*A61M 16/00* (2006.01)
*H01R 13/00* (2006.01)
*H01R 13/05* (2006.01)
*A61M 16/06* (2006.01)
*A61M 39/10* (2006.01)
*A61M 13/00* (2006.01)

(52) U.S. Cl.
CPC .... *A61M 16/0875* (2013.01); *A61M 16/0883* (2014.02); *A61M 16/109* (2014.02); *A61M 16/1085* (2014.02); *A61M 16/1095* (2014.02); *A61M 16/16* (2013.01); *H01R 13/005* (2013.01); *A61M 13/003* (2013.01); *A61M 16/0069* (2014.02); *A61M 16/06* (2013.01); *A61M 16/0833* (2014.02); *A61M 2039/1022* (2013.01); *A61M 2205/3368* (2013.01); *A61M 2205/3653* (2013.01); *A61M 2205/502* (2013.01); *A61M 2205/60* (2013.01); *A61M 2205/6045* (2013.01)

(58) Field of Classification Search
CPC .... H01R 13/5224; H01R 13/52; H01R 24/00; H01R 13/02; H01R 13/40; H01R 13/46; H01R 13/60; H01R 13/62
See application file for complete search history.

(56) References Cited

U.S. PATENT DOCUMENTS

| | | |
|---|---|---|
| 2,073,335 A | 3/1937 | Connell |
| 2,516,864 A | 8/1950 | Gilmore et al. |
| 2,634,311 A | 4/1953 | Darling |
| 2,745,074 A | 5/1956 | Darling |
| 2,788,936 A | 4/1957 | Kemnitz |
| 2,874,722 A | 2/1959 | Hamblin |
| 3,117,596 A | 1/1964 | Kahn |
| 3,163,707 A | 12/1964 | Darling |
| 3,283,580 A | 11/1966 | Jacob et al. |
| 3,394,954 A | 7/1968 | Sarns |
| 3,485,237 A | 12/1969 | Bedford |
| 3,495,628 A | 2/1970 | Boender |
| 3,582,094 A | 6/1971 | Whittaker |
| 3,582,968 A | 6/1971 | Buiting |
| 3,584,193 A | 6/1971 | Badertscher |
| 3,588,859 A | 6/1971 | Petree |
| 3,638,926 A | 2/1972 | Melville et al. |
| 3,659,604 A | 5/1972 | Melville et al. |
| 3,695,267 A | 10/1972 | Hirtz et al. |
| 3,703,892 A | 11/1972 | Meyers |
| 3,766,914 A | 10/1973 | Jacobs |
| 3,777,298 A | 12/1973 | Newman |
| 3,903,742 A | 9/1975 | Colton |
| 3,914,349 A | 10/1975 | Stipanuk |
| 3,926,223 A | 12/1975 | Petzetakis |
| 3,954,920 A | 5/1976 | Heath |
| 3,963,856 A | 6/1976 | Carlson et al. |
| 3,987,133 A | 10/1976 | Andra |
| 3,990,727 A | 11/1976 | Gallagher |
| 4,013,122 A | 3/1977 | Long |
| 4,013,742 A | 3/1977 | Lang |
| 4,028,444 A | 6/1977 | Brown et al. |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,139,762 A | 2/1979 | Pohrer et al. |
| 4,160,466 A | 7/1979 | Jousson |
| 4,172,105 A | 10/1979 | Miller et al. |
| 4,172,709 A | 10/1979 | Kippel et al. |
| 4,183,248 A | 1/1980 | West |
| 4,301,200 A | 11/1981 | Langenfeld et al. |
| 4,333,451 A | 6/1982 | Paluch |
| 4,428,403 A | 1/1984 | Lee |
| 4,430,994 A | 2/1984 | Clawson et al. |
| 4,463,593 A | 8/1984 | Parker |
| 4,473,923 A | 10/1984 | Neroni et al. |
| 4,487,232 A | 12/1984 | Kanao |
| 4,490,575 A | 12/1984 | Kutnyak |
| 4,500,480 A | 2/1985 | Cambio, Jr. |
| 4,507,707 A | 3/1985 | Willis |
| 4,529,867 A | 7/1985 | Velnosky et al. |
| 4,531,551 A | 7/1985 | Eichelberger et al. |
| 4,545,290 A | 10/1985 | Lieberman |
| 4,553,023 A | 11/1985 | Jameson et al. |
| 4,564,748 A | 1/1986 | Gupton |
| 4,574,188 A | 3/1986 | Midgley et al. |
| 4,588,425 A | 5/1986 | Usry et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,722,334 A | 2/1988 | Blackmer et al. |
| 4,753,758 A | 6/1988 | Miller |
| 4,774,032 A | 9/1988 | Coates et al. |
| 4,780,247 A | 10/1988 | Yasuda |
| 4,809,698 A | 3/1989 | Kogo |
| 4,813,280 A | 3/1989 | Miller et al. |
| 4,829,781 A | 5/1989 | Hitzler |
| 4,829,997 A | 5/1989 | Douwens et al. |
| 4,829,998 A | 5/1989 | Jackson |
| 4,830,515 A | 5/1989 | Cortes |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | Latorraca |
| 4,941,469 A | 7/1990 | Adahan |
| 4,942,877 A | 7/1990 | Sakai et al. |
| 4,944,310 A | 7/1990 | Sullivan |
| 4,967,744 A | 11/1990 | Chua |
| 5,031,612 A | 7/1991 | Clementi |
| 5,058,588 A | 10/1991 | Kaestle |
| 5,060,506 A | 10/1991 | Douglas |
| 5,062,145 A | 10/1991 | Zwaan et al. |
| 5,092,326 A | 3/1992 | Winn et al. |
| 5,101,820 A | 4/1992 | Christopher |
| 5,117,819 A | 6/1992 | Servidio et al. |
| 5,127,442 A | 7/1992 | Blomqvist |
| 5,134,996 A | 8/1992 | Bell |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,303,701 A | 4/1994 | Heins et al. |

(56) References Cited

U.S. PATENT DOCUMENTS

| | | |
|---|---|---|
| 5,307,243 A | 4/1994 | Sharp et al. |
| RE34,599 E | 5/1994 | Suszynk et al. |
| 5,336,156 A | 8/1994 | Miller et al. |
| 5,342,126 A | 8/1994 | Heston |
| 5,346,128 A | 9/1994 | Wacker |
| 5,347,211 A | 9/1994 | Jakubowski |
| 5,357,948 A | 10/1994 | Eilentropp |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,448,447 A | 9/1995 | Patton |
| 5,449,234 A | 9/1995 | Gipp et al. |
| 5,454,061 A | 9/1995 | Carlson |
| 5,454,479 A | 10/1995 | Kraus |
| 5,482,031 A | 1/1996 | Lambert |
| 5,483,616 A | 1/1996 | Chiu et al. |
| 5,499,737 A | 3/1996 | Kraus |
| 5,516,466 A | 5/1996 | Schlesch et al. |
| 5,529,060 A | 6/1996 | Salmon et al. |
| 5,537,996 A | 7/1996 | Mcphee |
| 5,551,731 A | 9/1996 | Gray et al. |
| 5,551,883 A | 9/1996 | Davis |
| 5,558,084 A | 9/1996 | Daniell |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinky |
| 5,630,752 A | 5/1997 | Inagaki et al. |
| 5,630,806 A | 5/1997 | Inagaki et al. |
| 5,637,168 A | 6/1997 | Carlson |
| 5,640,951 A | 6/1997 | Huddart et al. |
| 5,660,567 A | 8/1997 | Nierlich et al. |
| 5,667,306 A | 9/1997 | Montreuil |
| 5,673,687 A | 10/1997 | Dobson et al. |
| 5,720,293 A | 2/1998 | Quinn et al. |
| 5,759,149 A | 6/1998 | Goldberg et al. |
| 5,769,071 A | 6/1998 | Turnbull |
| 5,778,872 A | 7/1998 | Fukunaga et al. |
| 5,829,880 A | 11/1998 | Diedrich |
| 5,848,223 A | 12/1998 | Carlson |
| 5,881,393 A | 3/1999 | Marchello |
| 5,906,201 A | 5/1999 | Nilson |
| 5,943,473 A | 8/1999 | Levine |
| 5,988,164 A | 11/1999 | Paluch |
| 5,991,507 A | 11/1999 | Bencsits |
| D419,522 S | 1/2000 | Kamagai |
| 6,010,118 A | 1/2000 | Milewicz |
| 6,024,694 A | 2/2000 | Golberg |
| 6,038,457 A | 3/2000 | Barkat |
| 6,039,696 A | 3/2000 | Bell |
| 6,050,260 A | 4/2000 | Daniell et al. |
| 6,053,482 A | 4/2000 | Glenn et al. |
| 6,058,977 A | 5/2000 | Hotta |
| 6,078,729 A | 6/2000 | Kopel |
| 6,078,730 A | 6/2000 | Huddart et al. |
| 6,095,505 A | 8/2000 | Miller |
| 6,102,037 A | 8/2000 | Koch |
| 6,105,649 A | 8/2000 | Levingston et al. |
| 6,105,970 A | 8/2000 | Siegrist et al. |
| 6,109,782 A | 8/2000 | Fukura et al. |
| 6,116,965 A | 9/2000 | Arnett et al. |
| 6,125,847 A | 10/2000 | Lin |
| 6,126,610 A | 10/2000 | Rich et al. |
| 6,138,674 A | 10/2000 | Gull et al. |
| 6,142,974 A | 11/2000 | Kistner et al. |
| 6,158,431 A | 12/2000 | Poole |
| 6,167,883 B1 | 1/2001 | Beran et al. |
| 6,189,870 B1 | 2/2001 | Withall |
| 6,190,480 B1 | 2/2001 | Carlson |
| 6,196,980 B1 | 3/2001 | Akerfeldt et al. |
| 6,201,983 B1 | 3/2001 | Haumann et al. |
| 6,208,514 B1 | 3/2001 | Stark |
| 6,219,490 B1 | 4/2001 | Gibertoni et al. |
| 6,226,451 B1 | 5/2001 | Wong |
| 6,256,454 B1 | 7/2001 | Dykes |
| 6,272,933 B1 | 8/2001 | Gradon et al. |
| 6,311,958 B1 | 11/2001 | Stanek |
| 6,347,646 B2 | 2/2002 | Fukui |
| 6,349,722 B1 | 2/2002 | Gradon et al. |
| 6,349,724 B1 | 2/2002 | Burton et al. |
| 6,358,067 B1 | 3/2002 | Takase et al. |
| 6,360,741 B2 | 3/2002 | Truschel |
| 6,367,472 B1 | 4/2002 | Koch |
| 6,367,510 B1 | 4/2002 | Carlson |
| 6,367,974 B1 | 4/2002 | Lin |
| 6,374,864 B1 | 4/2002 | Philp |
| 6,379,188 B1 | 4/2002 | Cohen et al. |
| 6,384,755 B1 | 5/2002 | Hayden |
| 6,394,084 B1 | 5/2002 | Nitta |
| 6,394,145 B1 | 5/2002 | Gessil |
| 6,397,841 B1 | 6/2002 | Kenyon et al. |
| 6,397,846 B1 | 6/2002 | Skog et al. |
| 6,398,197 B1 | 6/2002 | Dickinson et al. |
| 6,402,207 B1 | 6/2002 | Segal et al. |
| 6,435,180 B1 | 8/2002 | Hewson |
| 6,454,583 B2 | 9/2002 | Lepine et al. |
| 6,463,925 B2 | 10/2002 | Nuckols et al. |
| 6,467,477 B1 | 10/2002 | Frank et al. |
| 6,474,335 B1 | 11/2002 | Lammers |
| 6,508,249 B2 | 1/2003 | Hoenig |
| 6,511,075 B1 | 1/2003 | Schmidt |
| 6,537,405 B1 | 3/2003 | Henderson et al. |
| 6,540,734 B1 | 4/2003 | Chiu |
| 6,543,412 B2 | 4/2003 | Amou et al. |
| 6,551,143 B2 | 4/2003 | Tanaka et al. |
| 6,554,260 B1 | 4/2003 | Lipscombe et al. |
| 6,564,011 B1 | 5/2003 | Janoff et al. |
| 6,584,972 B2 | 7/2003 | Mcphee |
| 6,591,061 B2 | 7/2003 | Wang |
| 6,594,366 B1 | 7/2003 | Adams |
| 6,598,604 B1 | 7/2003 | Seakins |
| 6,612,624 B1 | 9/2003 | Segal et al. |
| 6,631,718 B1 | 10/2003 | Lovell |
| 6,648,669 B1 | 11/2003 | Kim et al. |
| 6,668,828 B1 | 12/2003 | Figley et al. |
| 6,685,491 B2 | 2/2004 | Gergek |
| 6,691,707 B1 | 2/2004 | Gunaratnam et al. |
| 6,694,974 B1 | 2/2004 | George-Gradon et al. |
| 6,705,478 B1 | 3/2004 | Engle |
| 6,718,974 B1 | 4/2004 | Moberg |
| 6,827,084 B2 | 12/2004 | Grubb, Jr. |
| 6,827,109 B2 | 12/2004 | Mccaughtry |
| 6,874,771 B2 | 4/2005 | Birdsell et al. |
| 6,895,803 B2 | 5/2005 | Seakins et al. |
| 6,918,389 B2 | 7/2005 | Seakins et al. |
| 6,932,119 B2 | 8/2005 | Carlson |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,156,127 B2 | 1/2007 | Moulton et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,291,240 B2 | 11/2007 | Smith et al. |
| 7,316,768 B2 | 1/2008 | Aldridge |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,468,116 B2 | 12/2008 | Smith et al. |

(56) References Cited

U.S. PATENT DOCUMENTS

| | | |
|---|---|---|
| 7,478,635 B2 | 1/2009 | Wixey et al. |
| 7,525,663 B2 | 4/2009 | Kwok et al. |
| 7,588,029 B2 | 9/2009 | Smith et al. |
| 7,588,186 B2 | 9/2009 | Steffen et al. |
| 7,637,288 B2 | 12/2009 | Huber et al. |
| 7,647,926 B2 | 1/2010 | Gerder et al. |
| 7,677,246 B2 | 3/2010 | Kepler et al. |
| 7,727,028 B1 | 6/2010 | Zhang et al. |
| 7,743,767 B2 | 6/2010 | Ging et al. |
| 7,766,050 B2 | 8/2010 | Patel |
| 7,794,426 B2 | 9/2010 | Briones et al. |
| 7,814,907 B2 | 10/2010 | Bremner et al. |
| D628,288 S | 11/2010 | Row et al. |
| 7,827,981 B2 | 11/2010 | Bamford |
| 7,870,857 B2 | 1/2011 | Dhuper et al. |
| 7,874,291 B2 | 1/2011 | Ging et al. |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | Mcghin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | Mcghin et al. |
| 8,078,040 B2 | 12/2011 | Forrester |
| 8,091,547 B2 | 1/2012 | Thudor et al. |
| 8,100,124 B2 | 1/2012 | Becker et al. |
| 8,122,882 B2 | 2/2012 | Mcghin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,221,530 B2 | 7/2012 | Peter et al. |
| 8,235,041 B2 | 8/2012 | Seakins et al. |
| 8,245,709 B2 | 8/2012 | Rossen |
| 8,245,710 B2 | 8/2012 | Makinson et al. |
| 8,253,076 B2 | 8/2012 | Andel et al. |
| 8,257,286 B2 | 9/2012 | Meyer et al. |
| 8,266,293 B2 | 9/2012 | Faries, Jr. |
| 8,267,084 B2 | 9/2012 | Kwok |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,430,921 B2 | 4/2013 | Wong et al. |
| 8,453,641 B2 | 6/2013 | Payton et al. |
| 8,453,643 B2 | 6/2013 | Sanchez et al. |
| 8,459,259 B2 | 6/2013 | Klasek et al. |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,516,911 B2 | 8/2013 | Inoue |
| 8,522,782 B2 | 9/2013 | Lewis et al. |
| 8,528,552 B2 | 9/2013 | Von Blumenthal |
| 8,544,465 B2 | 10/2013 | Smith et al. |
| 8,545,096 B2 | 10/2013 | Reiter |
| 8,550,072 B2 | 10/2013 | Thudor et al. |
| 8,563,863 B2 | 10/2013 | Carlson |
| 8,563,864 B2 | 10/2013 | Carlson |
| 8,631,789 B2 | 1/2014 | Virr et al. |
| 8,640,560 B2 | 2/2014 | Burke |
| 8,640,696 B2 | 2/2014 | Pujol et al. |
| 8,709,187 B2 | 4/2014 | Smith et al. |
| 8,733,348 B2 | 5/2014 | Korneff et al. |
| 8,733,349 B2 | 5/2014 | Bath et al. |
| 8,770,190 B2 | 7/2014 | Doherty et al. |
| 8,783,252 B2 | 7/2014 | Pierro et al. |
| 8,800,970 B2 | 8/2014 | Heine et al. |
| 8,844,388 B2 | 9/2014 | Burke |
| 8,844,521 B2 | 9/2014 | Mccarthy |
| 8,844,522 B2 | 9/2014 | Huby et al. |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,985,105 B2 | 3/2015 | Burton et al. |
| 9,022,946 B2 | 5/2015 | Haque |
| 9,067,036 B2 | 6/2015 | Korneff et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | Von Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,440,040 B2 | 9/2016 | Klasek et al. |
| 9,446,210 B2 | 9/2016 | Orr et al. |
| 9,517,321 B2 | 12/2016 | Buechi et al. |
| 9,545,493 B2 | 1/2017 | Mayer et al. |
| 9,555,210 B2 | 1/2017 | Seakins et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| 9,838,759 B2 | 12/2017 | Kirmse et al. |
| 9,855,398 B2 | 1/2018 | Klasek et al. |
| 9,861,778 B2 | 1/2018 | Bath et al. |
| 9,937,314 B2 | 4/2018 | Buechi et al. |
| 9,937,316 B2 | 4/2018 | Buechi et al. |
| 9,974,921 B2 | 5/2018 | Klenner et al. |
| 9,987,455 B2 | 6/2018 | Stoks et al. |
| 10,046,136 B2 | 8/2018 | Pujol |
| 10,080,866 B2 | 9/2018 | Stoks et al. |
| 10,245,407 B2 | 4/2019 | Osborne et al. |
| 10,828,482 B2 | 11/2020 | Osborne et al. |
| 2001/0017134 A1 | 8/2001 | Bahr |
| 2001/0050080 A1 | 12/2001 | Seakins et al. |
| 2002/0038392 A1 | 3/2002 | De La Huerga |
| 2002/0100320 A1 | 8/2002 | Smith et al. |
| 2002/0120236 A1 | 8/2002 | Diaz et al. |
| 2002/0124847 A1 | 9/2002 | Smith et al. |
| 2002/0173717 A1 | 11/2002 | Rohling et al. |
| 2002/0186966 A1 | 12/2002 | Zimmer et al. |
| 2003/0059213 A1 | 3/2003 | Mackie et al. |
| 2003/0066526 A1 | 4/2003 | Thudor et al. |
| 2003/0107325 A1 | 6/2003 | Birkhead |
| 2003/0148664 A1 | 8/2003 | Cheng |
| 2003/0183294 A1 | 10/2003 | Carlson |
| 2003/0200727 A1 | 10/2003 | Kim |
| 2003/0236015 A1 | 12/2003 | Edirisuriya et al. |
| 2004/0013162 A1 | 1/2004 | Beerwerth |
| 2004/0055597 A1 | 3/2004 | Virr |
| 2004/0074493 A1 | 4/2004 | Seakins et al. |
| 2004/0074495 A1 | 4/2004 | Wickham et al. |
| 2004/0079371 A1 | 4/2004 | Gray |
| 2004/0081784 A1 | 4/2004 | Smith et al. |
| 2004/0087213 A1 | 5/2004 | Kao |
| 2004/0099268 A1 | 5/2004 | Smith et al. |
| 2004/0101026 A1 | 5/2004 | Nitta et al. |
| 2004/0149284 A1 | 8/2004 | Smith et al. |
| 2004/0182392 A1 | 9/2004 | Gerder et al. |
| 2004/0221843 A1 | 11/2004 | Baecke |

(56) References Cited

U.S. PATENT DOCUMENTS

| | | |
|---|---|---|
| 2004/0239001 A1 | 12/2004 | Edirisuriya et al. |
| 2004/0244858 A1 | 12/2004 | Jeong |
| 2005/0059957 A1 | 3/2005 | Campbell et al. |
| 2005/0152733 A1 | 7/2005 | Patel |
| 2006/0030191 A1 | 2/2006 | Tuin et al. |
| 2006/0118113 A1 | 6/2006 | Bremner et al. |
| 2006/0137445 A1 | 6/2006 | Smith |
| 2006/0165829 A1 | 7/2006 | Smith et al. |
| 2006/0196510 A1 | 9/2006 | Mcdonald |
| 2006/0237012 A1 | 10/2006 | Thudor et al. |
| 2006/0249160 A1 | 11/2006 | Scarberry |
| 2006/0272639 A1 | 12/2006 | Makinson et al. |
| 2006/0283447 A1 | 12/2006 | Dhuper et al. |
| 2007/0047733 A1 | 3/2007 | Bremer et al. |
| 2007/0051368 A1 | 3/2007 | Seakins et al. |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0169776 A1 | 7/2007 | Kepler |
| 2007/0175473 A1 | 8/2007 | Lewis et al. |
| 2007/0248934 A1 | 10/2007 | Mosimann |
| 2007/0277828 A1 | 12/2007 | Ho et al. |
| 2007/0284361 A1 | 12/2007 | Nadjafizadeh et al. |
| 2008/0000474 A1 | 1/2008 | Jochle et al. |
| 2008/0051674 A1 | 2/2008 | Davenport et al. |
| 2008/0066751 A1 | 3/2008 | Polacsek |
| 2008/0072900 A1 | 3/2008 | Kenyon et al. |
| 2008/0078259 A1 | 4/2008 | Duff |
| 2008/0078387 A1 | 4/2008 | Vandine |
| 2008/0078388 A1 | 4/2008 | Vandine |
| 2008/0105257 A1 | 5/2008 | Klasek et al. |
| 2008/0142019 A1* | 6/2008 | Lewis ............... A61M 16/0488 128/207.18 |
| 2008/0173305 A1 | 7/2008 | Frater |
| 2008/0202512 A1 | 8/2008 | Huber et al. |
| 2008/0205481 A1 | 8/2008 | Faries |
| 2008/0251073 A1 | 10/2008 | Jassell |
| 2008/0264413 A1 | 10/2008 | Doherty et al. |
| 2008/0308169 A1 | 12/2008 | Nielsen |
| 2009/0041080 A1 | 2/2009 | Koch |
| 2009/0044808 A1 | 2/2009 | Guney et al. |
| 2009/0050150 A1 | 2/2009 | Rossen et al. |
| 2009/0056712 A1 | 3/2009 | Cortez, Jr. |
| 2009/0078259 A1 | 3/2009 | Kooji et al. |
| 2009/0078440 A1 | 3/2009 | Carlson et al. |
| 2009/0107493 A1 | 4/2009 | Liu et al. |
| 2009/0107496 A1 | 4/2009 | Mcghin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0110379 A1 | 4/2009 | Mcghin et al. |
| 2009/0126817 A1 | 5/2009 | Gray |
| 2009/0149696 A1 | 6/2009 | Chilton, III |
| 2009/0174092 A1 | 7/2009 | Kwok et al. |
| 2009/0194106 A1 | 8/2009 | Smith et al. |
| 2009/0223514 A1 | 9/2009 | Smith et al. |
| 2009/0247989 A1 | 10/2009 | Burke |
| 2009/0301482 A1 | 12/2009 | Burton et al. |
| 2009/0320840 A1 | 12/2009 | Klasek et al. |
| 2010/0083965 A1 | 4/2010 | Virr et al. |
| 2010/0102799 A1 | 4/2010 | Schnidrig |
| 2010/0110056 A1 | 5/2010 | Kim et al. |
| 2010/0116272 A1 | 5/2010 | Row et al. |
| 2010/0147301 A1 | 6/2010 | Kwok |
| 2010/0154796 A1 | 6/2010 | Smith et al. |
| 2010/0224276 A1 | 9/2010 | Forrester et al. |
| 2010/0242963 A1 | 9/2010 | Brieger et al. |
| 2011/0017212 A1 | 1/2011 | Kenyon |
| 2011/0023874 A1* | 2/2011 | Bath ..................... A61M 16/06 128/203.14 |
| 2011/0046433 A1 | 2/2011 | Khodak |
| 2011/0046494 A1 | 2/2011 | Balji et al. |
| 2011/0073109 A1 | 3/2011 | Mayer et al. |
| 2011/0078109 A1 | 3/2011 | Mayer et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr |
| 2011/0162647 A1 | 7/2011 | Huby et al. |
| 2011/0168287 A1 | 7/2011 | Carlson |
| 2011/0180068 A1 | 7/2011 | Kenyon et al. |
| 2011/0186048 A1 | 8/2011 | Casse et al. |
| 2011/0244730 A1 | 10/2011 | Kondo et al. |
| 2011/0247623 A1 | 10/2011 | Mccarthy |
| 2011/0253136 A1 | 10/2011 | Sweeney et al. |
| 2011/0283999 A2 | 11/2011 | Smith et al. |
| 2011/0308518 A1 | 12/2011 | Mcgroary et al. |
| 2011/0313689 A1 | 12/2011 | Holley et al. |
| 2011/0316562 A1 | 12/2011 | Cefai et al. |
| 2012/0017904 A1 | 1/2012 | Ratto et al. |
| 2012/0060838 A1 | 3/2012 | Laura Lapoint et al. |
| 2012/0073573 A1 | 3/2012 | Thudor |
| 2012/0125333 A1 | 5/2012 | Bedford |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0248636 A1 | 10/2012 | Fridberg et al. |
| 2012/0255758 A1 | 10/2012 | Lee |
| 2012/0266880 A1 | 10/2012 | Young et al. |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0081621 A1 | 4/2013 | Korneff et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0255677 A1 | 10/2013 | Varga |
| 2013/0280055 A1 | 10/2013 | Daly et al. |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0037276 A1 | 2/2014 | Carlson |
| 2014/0090649 A1 | 4/2014 | Groll et al. |
| 2014/0116433 A1 | 5/2014 | Ghalib et al. |
| 2014/0120751 A1* | 5/2014 | Senatori ................ H01R 13/44 439/131 |
| 2014/0130802 A1 | 5/2014 | Virr et al. |
| 2014/0202460 A1 | 7/2014 | Bath et al. |
| 2014/0202462 A1 | 7/2014 | Stoks |
| 2014/0202463 A1 | 7/2014 | Ging et al. |
| 2014/0216446 A1 | 8/2014 | Wruck |
| 2014/0216459 A1 | 8/2014 | Vos et al. |
| 2014/0246021 A1 | 9/2014 | Buechi et al. |
| 2014/0251322 A1 | 9/2014 | Miller |
| 2014/0251331 A1 | 9/2014 | Korneff et al. |
| 2014/0311487 A1 | 10/2014 | Buechi et al. |
| 2014/0311489 A1 | 10/2014 | Heine et al. |
| 2014/0318536 A1 | 10/2014 | Landis et al. |
| 2014/0338666 A1 | 11/2014 | Visveshwara et al. |
| 2014/0345614 A1 | 11/2014 | Kwok |
| 2014/0349514 A1* | 11/2014 | Yang .................... H01R 12/721 439/487 |
| 2014/0366876 A1 | 12/2014 | Huby et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0107588 A1 | 4/2015 | Cheung et al. |
| 2015/0144130 A1 | 5/2015 | O'donnell et al. |
| 2015/0196725 A1 | 7/2015 | Oates et al. |
| 2015/0306333 A1 | 10/2015 | Amadio et al. |
| 2015/0359990 A1 | 12/2015 | Barker et al. |
| 2016/0008560 A1 | 1/2016 | Kwok |

(56) References Cited

U.S. PATENT DOCUMENTS

| | | | |
|---|---|---|---|
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0228671 A1 | 8/2016 | Jackson et al. |
| 2016/0256642 A1 | 9/2016 | Soysa et al. |
| 2016/0256657 A1 | 9/2016 | Klasek et al. |
| 2016/0271356 A1 | 9/2016 | Robertson et al. |
| 2016/0296721 A1 | 10/2016 | Landis et al. |
| 2016/0310691 A1 | 10/2016 | Bath et al. |
| 2016/0339200 A1 | 11/2016 | Bath et al. |
| 2016/0354573 A1 | 12/2016 | Buswell et al. |
| 2016/0367776 A1 | 12/2016 | Landis et al. |
| 2016/0367779 A1 | 12/2016 | Landis et al. |
| 2017/0095635 A1 | 4/2017 | Huby |
| 2017/0100556 A1 | 4/2017 | Munkelt et al. |
| 2017/0136198 A1 | 5/2017 | Delangre et al. |
| 2017/0161461 A1 | 6/2017 | Delangre et al. |
| 2017/0173293 A1 | 6/2017 | Osborne et al. |
| 2017/0239432 A1 | 8/2017 | Delangre et al. |
| 2017/0326320 A1 | 11/2017 | Baigent et al. |
| 2018/0028773 A1 | 2/2018 | Jan et al. |
| 2018/0078730 A1 | 3/2018 | Bath et al. |
| 2018/0169361 A1 | 6/2018 | Dennis et al. |
| 2018/0250491 A1 | 9/2018 | Row et al. |
| 2018/0280651 A1 | 10/2018 | Liu et al. |
| 2019/0076620 A1 | 3/2019 | Stoks et al. |

FOREIGN PATENT DOCUMENTS

| | | |
|---|---|---|
| AU | 2002244571 | 6/2002 |
| AU | 2007317198 | 5/2008 |
| AU | 2010206053 | 2/2011 |
| CA | 2464530 | 5/2003 |
| CA | 2495451 | 3/2004 |
| CA | 2890591 | 11/2017 |
| CN | 2243015 | 12/1996 |
| CN | 1341463 | 3/2002 |
| CN | 1549910 | 11/2004 |
| CN | 1598510 | 3/2005 |
| CN | 1886167 | 12/2006 |
| CN | 201672170 | 12/2010 |
| DE | 3110903 | 9/1982 |
| DE | 3618614 | 12/1987 |
| DE | 36 29 353 | 1/1988 |
| DE | 4020522 | 1/1992 |
| DE | 40 34 611 | 5/1992 |
| DE | 4102223 | 7/1992 |
| DE | 9200567 | 7/1992 |
| DE | 33 11 811 | 10/1994 |
| DE | 94 09 231.1 | 12/1994 |
| DE | 19647548 | 5/1998 |
| DE | 19958296 | 9/2001 |
| DE | 20202906 | 5/2002 |
| DE | 10312881 | 5/2004 |
| DE | 20 2004 006 484 | 9/2005 |
| DE | 20 2004 006 484.7 | 9/2005 |
| DE | 102004030747 | 1/2006 |
| DE | 20 2005 008 152.3 | 10/2006 |
| DE | 20 2005 008 156.6 | 10/2006 |
| DE | 202005008156 | 11/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 202006007397 | 9/2007 |
| DE | 20 2006 011 754.7 | 12/2007 |
| DE | 201 22 844.0 | 5/2008 |
| DE | 102006056781 A1 | 6/2008 |
| DE | 102007003454 | 7/2008 |
| DE | 102007003455 | 8/2008 |
| DE | 102007039391 | 2/2009 |
| DE | 202007018764 | 6/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 759.7 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 102006056781 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| DE | 102011055439 | 5/2013 |
| EP | 0111248 | 6/1984 |
| EP | 0111248 | 8/1986 |
| EP | 0201985 | 11/1986 |
| EP | 0258928 | 9/1988 |
| EP | 0291921 | 11/1988 |
| EP | 0342802 | 11/1989 |
| EP | 0481459 | 4/1992 |
| EP | 0535952 | 4/1993 |
| EP | 0556561 | 8/1993 |
| EP | 0567158 | 10/1993 |
| EP | 0232864 | 5/1994 |
| EP | 0616166 | 9/1994 |
| EP | 0621050 | 10/1994 |
| EP | 0672430 | 9/1995 |
| EP | 0885623 | 12/1998 |
| EP | 0956068 | 11/1999 |
| EP | 1078645 | 2/2001 |
| EP | 1127583 | 8/2001 |
| EP | 1138341 | 10/2001 |
| EP | 1145678 | 10/2001 |
| EP | 1262208 | 12/2002 |
| EP | 1147004 | 2/2003 |
| EP | 1352670 | 10/2003 |
| EP | 1380276 | 1/2004 |
| EP | 1579984 | 9/2005 |
| EP | 1396277 | 11/2005 |
| EP | 1646910 | 4/2006 |
| EP | 1669098 | 6/2006 |
| EP | 1683066 | 7/2006 |
| EP | 1457223 | 10/2006 |
| EP | 1741462 | 1/2007 |
| EP | 1924311 | 5/2008 |
| EP | 2075026 | 7/2009 |
| EP | 2079505 | 7/2009 |
| EP | 2089086 | 8/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2355881 | 8/2011 |
| EP | 2133611 | 9/2011 |
| EP | 2415445 | 2/2012 |
| EP | 2471568 | 7/2012 |
| EP | 2269680 | 9/2012 |
| EP | 2498854 | 9/2012 |
| EP | 1535722 | 11/2012 |
| EP | 2524714 | 11/2012 |
| EP | 2575944 | 4/2013 |

(56) References Cited

FOREIGN PATENT DOCUMENTS

| | | |
|---|---|---|
| EP | 2340867 | 5/2013 |
| EP | 2514478 | 7/2013 |
| EP | 2143459 | 8/2013 |
| EP | 2640451 | 9/2013 |
| EP | 2651481 | 10/2013 |
| EP | 2654869 | 10/2013 |
| EP | 2667919 | 12/2013 |
| EP | 2689174 | 1/2014 |
| EP | 2337604 | 3/2014 |
| EP | 2760516 | 8/2014 |
| EP | 2830695 | 2/2015 |
| EP | 2877224 | 6/2015 |
| EP | 3013402 | 5/2016 |
| EP | 3053623 | 8/2016 |
| EP | 2703034 | 5/2017 |
| GB | 1167551 | 10/1969 |
| GB | 1310949 | 3/1973 |
| GB | 1364127 | 8/1974 |
| GB | 2056611 | 3/1981 |
| GB | 2176313 | 12/1986 |
| GB | 2173274 | 2/1989 |
| GB | 2277689 | 11/1994 |
| GB | 2495771 | 4/2013 |
| JP | S56-109189 U | 8/1981 |
| JP | 59-113392 | 6/1984 |
| JP | S59-113392 | 6/1984 |
| JP | 03194747 | 8/1991 |
| JP | 05-317428 | 12/1993 |
| JP | H0623051 | 2/1994 |
| JP | 08-061731 | 3/1996 |
| JP | H08-109984 A | 4/1996 |
| JP | H09-234247 | 9/1997 |
| JP | H09-276408 | 10/1997 |
| JP | H11-033119 A | 2/1999 |
| JP | 11-248076 | 9/1999 |
| JP | 11-286058 | 10/1999 |
| JP | H11-286058 A | 10/1999 |
| JP | 2001-095920 | 4/2001 |
| JP | 2001-129091 | 5/2001 |
| JP | 2001-511507 | 8/2001 |
| JP | 2003275312 | 3/2003 |
| JP | 2003-139276 | 5/2003 |
| JP | 2004-148817 | 5/2004 |
| JP | 2005-514121 | 5/2005 |
| JP | 4242816 | 3/2009 |
| JP | 44-022293 | 2/2010 |
| JP | 4422293 | 2/2010 |
| JP | 11-033119 | 2/2011 |
| JP | 2017-500126 | 1/2017 |
| NZ | 564886 | 2/2011 |
| NZ | 579384 | 5/2011 |
| NZ | 587113 | 12/2011 |
| NZ | 586325 | 1/2012 |
| NZ | 589766 | 5/2012 |
| NZ | 575837 | 7/2012 |
| NZ | 583968 | 10/2012 |
| NZ | 597020 | 6/2013 |
| NZ | 597827 | 6/2013 |
| NZ | 590924 | 8/2013 |
| NZ | 600986 | 8/2013 |
| NZ | 597179 | 9/2013 |
| NZ | 604137 | 6/2014 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605 | 4/2016 |
| NZ | 710078 | 1/2017 |
| NZ | 710351 | 1/2017 |
| NZ | 631008 | 7/2017 |
| RU | 2012124053 | 12/2013 |
| SU | 379270 | 4/1973 |
| SU | 768402 | 10/1980 |
| WO | WO 92/21163 | 11/1992 |
| WO | WO 96/020748 | 7/1996 |
| WO | WO 97/18001 | 5/1997 |
| WO | WO 98/26826 | 6/1998 |
| WO | WO 00/029057 | 5/2000 |
| WO | WO 01/010489 | 2/2001 |
| WO | WO 01/032069 | 5/2001 |
| WO | WO 01/097894 | 12/2001 |
| WO | WO 02/032486 | 4/2002 |
| WO | WO 02/066106 | 8/2002 |
| WO | WO 02/066107 | 8/2002 |
| WO | WO 03/022342 | 3/2003 |
| WO | WO 03/026721 | 4/2003 |
| WO | WO 2004/011072 | 2/2004 |
| WO | WO 2004/024429 | 3/2004 |
| WO | WO 2004/039444 | 5/2004 |
| WO | WO 2004/105847 | 12/2004 |
| WO | WO 2004/105848 | 12/2004 |
| WO | WO 2004/112873 | 12/2004 |
| WO | WO 2005/011785 | 2/2005 |
| WO | WO 2005/021076 | 3/2005 |
| WO | WO 2006/017350 | 2/2006 |
| WO | WO 2006/092001 | 9/2006 |
| WO | WO 2006/095151 | 9/2006 |
| WO | WO 2007/051230 | 5/2007 |
| WO | WO 2008/055307 | 5/2008 |
| WO | WO 2008/055308 | 5/2008 |
| WO | WO 2008/058328 | 5/2008 |
| WO | WO 2008/060046 | 5/2008 |
| WO | WO 2008/060295 | 5/2008 |
| WO | WO 2008/076230 | 6/2008 |
| WO | WO 2009/015410 | 2/2009 |
| WO | WO 2009/022004 | 2/2009 |
| WO | WO 2009/085995 | 7/2009 |
| WO | WO 2010/031125 | 3/2010 |
| WO | WO 2010/031126 | 3/2010 |
| WO | WO 2010/084183 | 7/2010 |
| WO | WO 2011/030251 | 3/2011 |
| WO | WO 2011/051837 | 5/2011 |
| WO | WO 2011/051870 | 5/2011 |
| WO | WO 2011/136665 | 11/2011 |
| WO | WO 2011/162622 | 12/2011 |
| WO | WO 2012/053910 | 4/2012 |
| WO | WO 2012/065999 | 5/2012 |
| WO | WO 2012/135912 | 10/2012 |
| WO | WO 2012/154064 | 11/2012 |
| WO | WO 2012/154883 | 11/2012 |
| WO | WO 2012/164407 | 12/2012 |
| WO | WO 2013/022356 | 2/2013 |
| WO | WO 2013/026901 | 2/2013 |
| WO | WO 2013/045572 | 4/2013 |
| WO | WO 2013/045575 | 4/2013 |
| WO | WO 2013/049660 | 4/2013 |
| WO | WO 2013/050907 | 4/2013 |
| WO | WO 2013/127474 | 9/2013 |
| WO | WO 2013/137753 | 9/2013 |
| WO | WO 2013/147623 | 10/2013 |
| WO | WO 2013/165263 | 11/2013 |
| WO | WO 2014/025266 | 2/2014 |
| WO | WO 2014/055407 | 4/2014 |
| WO | WO 2014/077706 | 5/2014 |
| WO | WO 2014/088430 | 6/2014 |
| WO | WO 2014/205513 | 12/2014 |
| WO | WO 2015/038013 | 3/2015 |
| WO | WO 2015/060729 | 4/2015 |
| WO | WO 2015/142192 | 9/2015 |
| WO | WO 2015/160268 | 10/2015 |
| WO | WO 2015/164407 | 10/2015 |
| WO | WO 2016/042522 | 3/2016 |
| WO | WO 2016/089224 | 6/2016 |
| WO | WO 2016/139645 | 9/2016 |
| WO | WO 2017/027906 | 2/2017 |
| WO | WO 2017/043981 | 3/2017 |

(56) References Cited

FOREIGN PATENT DOCUMENTS

| WO | WO 2017/126980 | 7/2017 |
|----|----------------|--------|
| WO | WO 2018/116187 | 6/2018 |

OTHER PUBLICATIONS

Sawyer et al. "An introduction to human factors in medical devices." US Department of Health and Human Services, Public Health Service, Fiid and Drug Administration, Center for Devices and Radiological Health (1996).

* cited by examiner

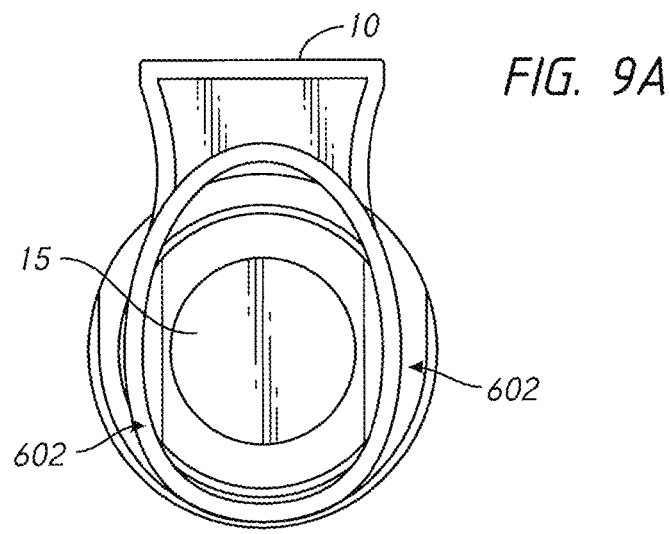
FIG. 9A
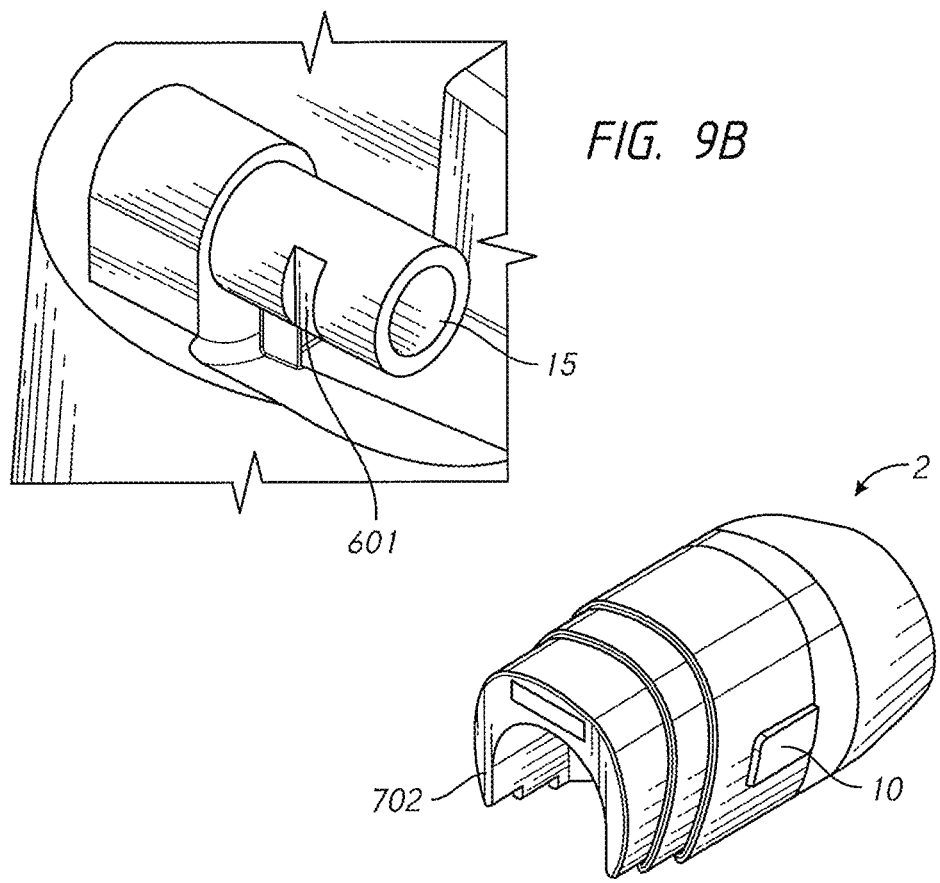
FIG. 9B
FIG. 10A

HUMIDIFICATION SYSTEM CONNECTIONS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. Provisional Application No. 61/919,485, filed Dec. 20, 2013, and U.S. Provisional Application No. 62/059,339, filed Oct. 3, 2014, each of which is hereby incorporated by reference in its entirety.

BACKGROUND

Field

The present disclosure generally relates to methods or devices for providing heated and/or humidified gases to a user, particularly respiratory gases. More particularly, the present disclosure relates to apparatus and techniques that provide for or enable connections between components of a humidification system. The apparatus and techniques disclosed may be used for providing gases to and/or removing gases from a patient, such as in positive airway pressure (PAP), respirator, anaesthesia, ventilator, and insufflation systems.

Description of the Related Art

Humidification systems have been devised that deliver heated and/or humidified gases for various medical procedures, including respiratory treatment, laparoscopy, and the like. These systems may be configured to control temperature, humidity, and flow rates.

Humidification systems also include medical circuits, including various components to transport heated and/or humidified gases to and from patients. For example, in some breathing circuits such as PAP or assisted breathing circuits, gases inhaled by a patient are delivered from a heater-humidifier through an inspiratory tube. As another example, tubes may deliver humidified gas (commonly $CO_2$) into the abdominal cavity in insufflation circuits. This may help prevent dessication or drying out of the patient's internal organs, and may decrease the amount of time needed for recovery from surgery. Unheated tubing allows significant heat loss to ambient cooling. This cooling may result in unwanted condensation or "rainout" along the length of the tubing transporting warm, humidified air. Heater wires may extend along at least a portion of the tubing forming the circuit to prevent or at least reduce condensation forming therein.

While prior arrangements have provided the desired therapies, a need remains for apparatus that provides for greater ease of connection and/or disconnection of components of humidification systems. Accordingly, it is an object of certain features, aspects, and advantages of the present disclosure to overcome or ameliorate one or more of the disadvantages of the prior art or to at least provide the public with a useful choice.

SUMMARY

According to a first aspect of the present disclosure, there is provided a circuit connector for a humidification system, the humidification system comprising a base unit and a humidification chamber, the humidification chamber being configured to be engageable with the base unit, the circuit connector comprising: an inlet configured to provide a fluid connection to an outlet of the humidification chamber to receive heated and/or humidified gases therefrom; an outlet configured to provide a fluid connection to a conduit for directing the heated and/or humidified gases to or from a patient or other person; and an electrical terminal configured to provide an electrical connection to an electrical terminal associated with the base unit, wherein the circuit connector is configured to make a releasable and lockable connection to the outlet of the humidification chamber, thereby providing the fluid connection from the inlet of the circuit connector to the outlet of the humidification chamber, such that the circuit connector also provides the electrical connection from the electrical terminal of the circuit connector to the electrical terminal associated with the base unit when the humidification chamber is engaged with the base unit and the circuit connector is connected to the outlet of the humidification chamber.

According to some aspects of the present disclosure, this is provided a circuit connector for a humidification system. The humidification system comprises a base unit and a humidification chamber. The humidification chamber is configured to be engageable with the base unit. The circuit connector comprises an inlet configured to provide a fluid connection to an outlet of the humidification chamber to receive heated and/or humidified gases therefrom. An outlet is configured to provide a fluid connection to a conduit for directing the heated and/or humidified gases to or from a patient or other person. An electrical terminal is configured to provide an electrical connection to a base unit electrical terminal. The electrical terminal comprises exposed contact pads that are sized, positioned and configured to be brought into contact with the base unit electrical terminal In some such configurations, the electrical terminal comprises six equally spaced contact pads. In some such configurations, the six equally spaced contact pads comprise two contact pads for sensor wires, two contact pads for identification, and two contact pads for heater wires. In some such configurations, the two contact pads for the heater wires are longer than the two contact pads for the sensor wires and the two contact pads for identification. In some such configurations, the six equally spaced contact pads all have the same length. In some such configurations, the electrical terminal comprises six contact pads that are not all uniformly spaced apart. In some such configurations, the six equally spaced contact pads comprise two contact pads for sensor wires, two contact pads for identification, and two contact pads for heater wires. In some such configurations, the two contact pads for the heater wires are longer than the two contact pads for the sensor wires and the two contact pads for identification. In some such configurations, the two contact pads for the heater wires are adjacent each other. In some such configurations, the two contact pads for the sensor wires and the two contact pads for identification are uniformly spaced and the two contact pads for the heater wires are spaced apart from each other by the same spacing as between the two contact pads for the sensor wires but the two contact pads for the heater wires are spaced apart from the closest of the two contact pads for the sensor wires and the two contact pads for identification by a distance greater than the distance separating the two contact pads for the heater wires from each other. In some such configurations, the two contact pads for the heater wires are longer than the two contact pads for the sensor wires and the two contact pads for identification. In some such configurations, the contact pads are formed on a circuit board and the printed circuit board is supported by an outer support surface. In some such configurations, the outer support surface is wider at a distal end than at a proximal end.

According to one embodiment, the circuit connector comprises an orientator configured to orientate the circuit connector relative to the outlet of the humidification chamber and/or to orientate the electrical terminal of the circuit connector relative to the electrical terminal associated with the base unit.

The orientator may comprise a recess configured to slidably engage a projection on the outlet of the humidification chamber such that the circuit connector may only be slid onto the outlet of the humidification chamber in a predetermined orientation. Conversely, the orientator may comprise a projection configured to slidably engage a recess in the outlet of the humidification chamber.

The provision of orientation features helps to ensure there is alignment of the electrical terminal of the circuit connector with the electrical terminal associated with the base unit, providing increased ease of assembly. Further, the releasable and lockable connection of the circuit connector to the outlet of the humidification chamber helps to ensure the correct orientation is maintained.

The outlet of the humidification chamber may comprise a first portion that extends substantially vertically from the humidification chamber and a second portion that extends substantially horizontally from the first portion, the second portion being downstream of the first portion, in use, wherein the inlet of the circuit connector is configured to provide a fluid connection to the second portion of the circuit connector. According to this embodiment, the circuit connector may comprise a cutout to accommodate the first portion, the cutout inhibiting or limiting engagement of the circuit connector to the outlet of the humidification chamber when not correctly orientated to accommodate the first portion received in the cutout.

The cutout may be contoured to have a wider opening and a narrower termination, thereby providing tolerance as to the orientation of the circuit connector on initial engagement and correcting the orientation on continued engagement as the circuit connector is pushed towards the outlet of the humidification chamber.

The electrical terminal of the circuit connector may comprise one or more pins configured to, in use, make contact with one or more tracks of a printed circuit board, the electrical terminal associated with the base unit comprising said printed circuit board. Alternatively, the electrical terminal of the circuit connector may comprise a printed circuit board comprising one or more tracks configured to, in use, make contact with one or more pins, the electrical terminal associated with the base unit comprising said one or more pins.

The electrical terminal of the circuit connector may alternatively comprise an edge card configured to, in use, be received in an edge card receptacle, the electrical terminal associated with the base unit comprising said edge card receptacle.

The electrical terminal of the circuit connector may alternatively comprise an edge card receptacle configured to, in use, receive an edge card, the electrical terminal associated with the base unit comprising said edge card.

Other forms of electrical terminals will be apparent to those skilled in the art and are included within the scope of the present disclosure.

The electrical terminal of the circuit connector may be electrically connected to one or more heater wires and/or one or more sensor wires, the conduit comprising said one or more heater wires and/or said one or more sensor wires, or having said one or more heater wires and/or said one or more sensor wires associated therewith.

The circuit connector may comprise a recess or projection configured to be engaged by a latch of the humidification chamber (the latch being provided on a wall of the outlet of the humidification chamber), thereby providing said releasable and lockable connection of the circuit connector to the outlet of the humidification chamber.

The circuit connector may additionally or alternatively comprise a latch configured to engage a recess or projection of a wall of the outlet of the humidification chamber, thereby providing said releasable and lockable connection of the circuit connector to the outlet of the humidification chamber.

The circuit connector may comprise an activator configured for disengaging the latch from the recess or projection to allow removal of the circuit connector from the outlet of the humidification chamber.

The activator may comprise at least one manually depressible button or switch.

At least a portion of the circuit connector may be receivable inside the outlet of the humidification chamber.

According to a second aspect, there is provided a circuit connector for a humidification system, the humidification system comprising a base unit and a humidification chamber, the circuit connector comprising: an inlet configured to provide a fluid connection to an outlet of the humidification chamber to receive heated and/or humidified gases therefrom; an outlet configured to provide a fluid connection to a conduit for directing heated and/or humidified gases to or from a patient or other person; an electrical terminal configured to provide an electrical connection to an electrical terminal associated with the base unit; and an orientator configured to orientate the circuit connector relative to the outlet of the humidification chamber.

The electrical terminal of the circuit connector may be substantially parallel to the inlet of the circuit connector and/or to a direction of engagement used to electrically connect the electrical terminal of the circuit connector to the electrical terminal associated with the base unit, thereby enabling both the electrical and fluid connections to be effected in a single motion.

According to a third aspect, there is provided a medical tube comprising the circuit connector of the first or second aspects. The circuit connector may be integral to or connected to a conduit and/or configured to form at least part of an inspiratory limb or an expiratory limb of a respiratory circuit.

According to a fourth aspect, there is provided a humidification chamber for a humidification system, the humidification chamber comprising: an outer wall; an upper wall connected to the outer wall, the outer wall and the upper wall at least partially defining a volume for containing a liquid; an inlet to receive gases into the humidification chamber from a gases source; and an outlet configured to connect to a circuit connector for directing heated and/or humidified gases from the humidification chamber to a patient or other person, wherein the outlet is configured to provide a releasable and lockable connection to the circuit connector and/or comprises an orientator to control the orientation of the circuit connector relative to the outlet.

The orientator may comprise a recess configured to slidably engage a projection on the circuit connector such that the circuit connector may only be slid onto the outlet of the humidification chamber in a predetermined orientation. Conversely, the orientator may comprise a projection configured to slidably engage a recess in the circuit connector such that the circuit connector may only be slid onto the outlet of the humidification chamber in a predetermined orientation.

The outlet of the humidification chamber may comprise a first portion that extends substantially vertically from the humidification chamber and a second portion that extends substantially horizontally from the first portion, the second portion being downstream of the first portion, in use.

The humidification chamber may comprise a recess or projection configured to be engaged by a latch of the circuit connector, thereby providing said releasable and lockable connection of the circuit connector to the outlet of the humidification chamber. Alternatively, the humidification chamber may comprise a latch configured to engage a recess or projection of the circuit connector.

The humidification chamber may comprise an activator for disengaging the latch from the recess or projection to allow removal of the circuit connector from the outlet of the humidification chamber.

The activator may comprise at least one manually depressible button or switch.

The outlet of the humidification chamber may be configured to receive at least a portion of the circuit connector inside the outlet of the humidification chamber.

The humidification chamber may comprise an orientator to control orientation of the humidification chamber relative to the base unit.

According to a fifth aspect, there is provided a humidification chamber for a humidification system, the humidification chamber comprising: an outer wall; an upper wall connected to the outer wall, the outer wall and the upper wall at least partially defining a volume for containing a liquid; an inlet to receive gases from a gases source; an outlet configured to connect to a circuit connector for directing heated and/or humidified gases to a patient or other person; and an orientator to control orientation of the humidification chamber relative to the base unit.

The orientator may comprise a recess configured to slidably engage a projection on or associated with the base unit such that the humidification chamber may only be engaged with the base unit in a predetermined orientation. Alternatively, the orientator may comprise a projection configured to slidably engage a recess in or associated with the base unit such that the humidification chamber may only be engaged with the base unit in a predetermined orientation.

The orientator may be configured to orientate, at least in part, the circuit connector relative to the outlet of the humidification chamber. Additionally or alternatively, the orientator may be configured to orientate, at least in part, an electrical terminal of the circuit connector relative to an electrical terminal associated with the base unit.

In an embodiment, the humidification chamber is configured to couple to the base unit, at least in part, via a coupler of or associated with the base unit. Additionally or alternatively, at least the electrical terminal of the circuit connector may be configured to connect with an electrical terminal of the coupler. Further connections may be provided between the coupler and the base unit for exchanging information therebetween and/or electrical power, such as for powering heater wires in the conduit, via the circuit connector.

In an embodiment, at least a downstream end of the outlet of the humidification chamber is oriented in a substantially parallel direction to a direction of engagement of the humidification chamber with the base unit. Additionally or alternatively, a direction of engagement of an electrical terminal of the circuit connector to the electrical terminal associated with the base unit and/or a coupler for the base unit is substantially parallel to at least a downstream end of the outlet of the humidification chamber, and/or a direction of engagement of the humidification chamber with the base unit.

The humidification chamber may comprise an outlet configured to connect to the circuit connector of the first or second aspects.

According to a sixth aspect, there is provided a coupler for a humidification system, the coupler comprising: first connections configured to structurally and electrically connect the coupler to a base unit of the humidification system, the base unit configured to operatively engage a humidification chamber; second connections configured to electrically connect the coupler to a circuit connector that is configured to fluidly connect an outlet of the humidification chamber to a conduit to deliver heated and/or humidified gases to a patient or other person, wherein the coupler comprises one or more guide portions for orientating the humidification chamber and/or the circuit connector relative to the base unit as the humidification chamber and/or the circuit connector are brought into engagement with the coupler.

The first and second connections may be configured to be made by urging the humidification chamber and/or the circuit connector in substantially the same direction, i.e., the directions may be parallel.

According to a seventh aspect, there is provided a base unit for a humidification system, in which system a humidification chamber is configured to be engageable with the base unit, a circuit connector is configured to fluidly connect to an outlet of the humidification chamber, and an electrical terminal of the circuit connector is configured to electrically connect to an electrical terminal associated with the base unit, the base unit comprising: one or more guide portions for orientating the humidification chamber and/or the circuit connector relative to the base unit as the humidification chamber and/or the circuit connector are brought into engagement with the base unit.

According to an eighth aspect, there is provided a base unit for a humidification system, in which system a humidification chamber is configured to be engageable with the base unit, a circuit connector is configured to fluidly connect to an outlet of the humidification chamber, and an electrical terminal of the circuit connector is configured to electrically connect to an electrical terminal associated with the base unit, wherein the base unit is configured to receive the humidification chamber in a direction substantially the same or parallel to a direction in which the electrical terminal of the base unit is configured to electrically connect to the electrical terminal of the circuit connector.

In some configurations, the base unit has an insert block that is positioned between the electrical terminal of the circuit connector and the electrical terminal associated with the base unit. In some such configurations, the insert block is mounted to the base unit. In some such configurations, the base unit comprises a removable coupler and the insert block is mounted to the removable coupler. In some such configurations, the insert block has a body and the removable coupler has a hood with the body of the insert block being sized and configured to be received within the hood of the removable coupler. In some such configurations, the insert block has a downwardly facing contact surface. In some such configurations, one or more contact terminals protrude downwardly beyond the downwardly facing contact surface.

According to a ninth aspect, there is provided a humidification system comprising: a circuit connector of the first or second aspects; and/or a medical tube of the third aspect;

and/or a humidification chamber of the fourth or fifth aspects; and/or a coupler of the sixth aspect; and/or a base unit of the seventh or eighth aspects.

Electrical and/or fluid and/or structural connections may be effected between the various components listed in the ninth aspect, with the details thereof being specified with regards the first through eighth aspects.

According to a tenth aspect, there is provided a humidification system comprising: a base unit; a humidification chamber configured to operatively connect to the base unit, the humidification chamber comprising an outer body defining a chamber, an inlet port comprising a wall defining a passage into the chamber, and an outlet port comprising a wall defining a passage out of the chamber; and a circuit connector configured to connect the outlet port to a gases delivery conduit, wherein connection of the circuit connector to the outlet port is made in substantially the same direction as the connection of the humidification chamber to the base unit.

The circuit connector may comprise an electrical terminal configured to electrically connect the gases delivery conduit and/or the circuit connector to an electrical terminal associated with the base unit.

The electrical terminal of the circuit connector may connect to the electrical terminal associated with the base unit in substantially the same direction as the connection of the circuit connector to the outlet port of the humidification chamber and/or the connection of the humidification chamber to the base unit. Said direction may be substantially horizontal.

Any one or more of the base unit, the humidification chamber, the circuit connector or a coupler provided between the humidification chamber and the base unit may include an orientator to control relative orientation of at least one of the others of the base unit, the humidification chamber, the circuit connector or the coupler.

According to an eleventh aspect, there is provided a humidification system comprising: a base unit; a humidification chamber configured to operatively connect to the base unit, the humidification chamber comprising an outer body defining a chamber, an inlet port comprising a wall defining a passage into the chamber, and an outlet port comprising a wall defining a passage out of the chamber; and a circuit connector configured to connect the outlet port to a gases delivery conduit, the circuit connector comprising an electrical terminal configured to electrically connect to an electrical terminal associated with the base unit, wherein any one or more of the base unit, the humidification chamber, the circuit connector or a coupler provided between the humidification chamber and the base unit may include an orientator to control relative orientation of at least one of the others of the base unit, the humidification chamber, the circuit connector or the coupler.

The humidification system may comprise a pressurized gas source, the pressurized gas source comprising an outlet, the outlet of the pressurized gas source being connected or connectable to the inlet port of the humidification chamber, the humidification chamber defining a flow passage between the pressurized gas source and outlet port.

The circuit connector may be configured to provide a releasable and lockable connection to the outlet port of the humidification chamber.

The humidification chamber may be releasably and lockably engageable with the base unit.

The circuit connector is preferably not fixedly or lockably attachable to the base unit and/or the circuit connector is preferably not fixedly or lockably attachable to a coupler located between the circuit connector and the base unit.

According to a twelfth aspect, there is provided a method of attaching components of a humidification system, the method comprising: slidably engaging a humidification chamber to a base unit in a first direction; and slidably engaging a circuit connector to an outlet of the humidification chamber in a second direction, wherein the first and second directions are substantially the same.

Said slidably engaging the circuit connector to the outlet of the humidification chamber may result in or effect electrical connection of the circuit connector to the base unit and/or a control module associated with the base unit.

According to a thirteenth aspect, there is provided a method of attaching components of a humidification system, the method comprising: slidably engaging a circuit connector to an outlet of a humidification chamber in a first direction; and slidably engaging the humidification chamber and the circuit connector to a base unit in a second direction, wherein the first and second directions are substantially the same.

Said slidably engaging the humidification chamber and the circuit connector to a base unit may result in or effect electrical connection of the circuit connector to the base unit and/or a control module associated with the base unit. The first and second directions may be substantially horizontal.

For purposes of summarizing the disclosure and the advantages achieved over the prior art, certain objects and advantages have been described herein. It is to be understood that not necessarily all such objects or advantages need to be achieved in accordance with any particular embodiment. Thus, for example, those skilled in the art will recognize that the disclosed configuration or configurations may be embodied or carried out in a manner that achieves or optimizes one advantage or group of advantages as taught or suggested herein without necessarily achieving other advantages as may be taught or suggested herein. All of these embodiments are intended to be within the scope of the present disclosure.

BRIEF DESCRIPTION OF THE DRAWINGS

These and other features, aspects and advantages of the present disclosure will be described with reference to the following drawings, which are illustrative but should not be limiting of the present invention.

FIGS. 8A to 8E, 9A, 9B, 10A to 10K, 11A, and 11B are alternative views of example embodiments of circuit connectors and/or humidification chamber outlets configured to connect therewith.

DETAILED DESCRIPTION

Certain embodiments and examples of humidification systems and/or apparatus and/or methods are described herein. Those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described herein.

Humidification System

Figure 1:
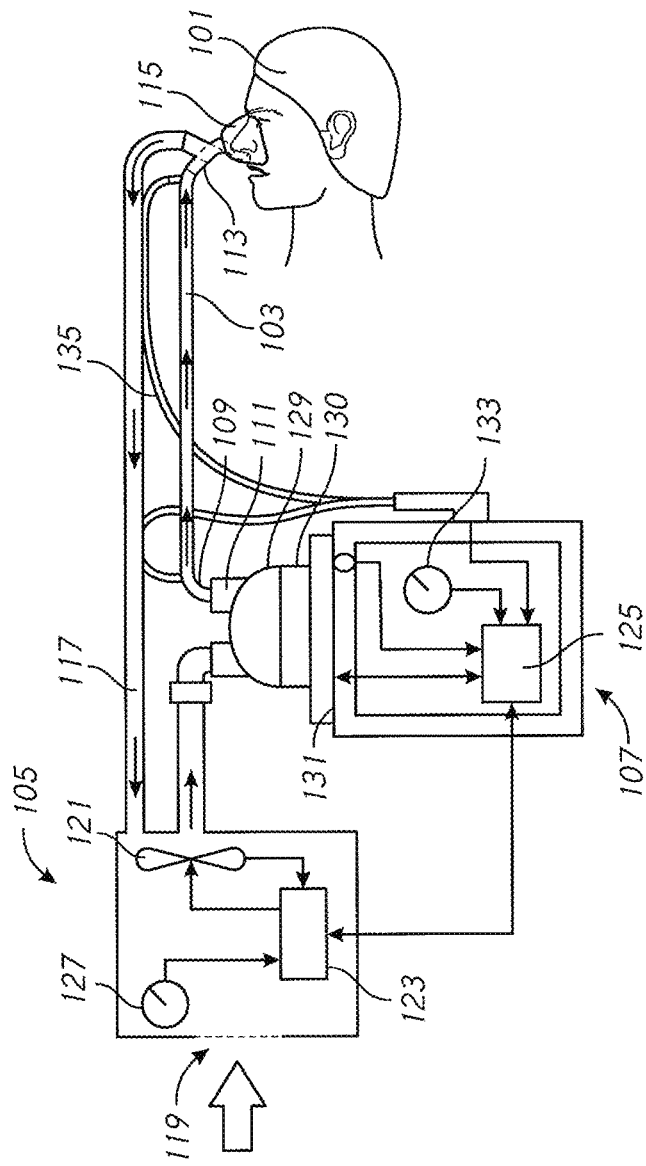
FIG. 1 is a schematic view of an example embodiment of a humidification system.

For a more detailed understanding of the disclosure, reference is first made to FIG. 1, which shows an example breathing circuit which includes one or more medical tubes. Such a breathing circuit may be a continuous, variable, or bi-level positive airway pressure (PAP) system or other form of respiratory therapy.

Gases may be transported in the breathing circuit of FIG. 1 as follows. Dry or relatively dry gases pass from a gases source 105 to a humidifier 107, which humidifies the dry gases. The gases source 105 may be, for example, a ventilator or a blower. The humidifier 107 connects to an end 109 of an inspiratory tube 103 via a port 111, thereby supplying humidified gases to the inspiratory tube 103, which may be configured to deliver breathing gases to a patient. The gases flow through the inspiratory tube 103 to a Y-piece 113, and then to a patient 101 through a patient interface 115 connected to the Y-piece 113. An expiratory tube 117 also connects to the patient interface 115 through the Y-piece 113 and may be configured to move exhaled gases away from the patient 101. Here, the expiratory tube 117 returns exhaled gases from the patient 101 to the gases source 105.

In this example, dry or relatively dry gases enter the gases source 105 through a vent 119. A fan 121 may improve gas flow into the gases source 105 by drawing air or other gases through the vent 119. The fan 121 may be, for instance, a variable speed fan, where an electronic controller 123 controls the fan speed. In particular, the function of the electronic controller 123 may be controlled by an electronic master controller 125 in response to inputs to the master controller 125 and a user-set predetermined required value (preset value) of pressure or fan speed via a dial 127.

The humidifier 107 comprises a humidification chamber 129 containing a volume of water 130 or other suitable humidifying liquid. The humidification chamber 129 is removable from the humidifier 107 after use to allow the humidification chamber 129 to be more readily sterilized or disposed. The body of the humidification chamber 129 may be formed from a non-conductive glass or plastics material, but the humidification chamber 129 may also include conductive components. For instance, the humidification chamber 129 may include a highly heat-conductive base (for example, an aluminum base) contacting or associated with a heater plate 131 on the humidifier 107.

The humidifier 107 may also include electronic controls. In this example, the humidifier 107 includes an electronic, analog, or digital master controller 125. The master controller 125 may be a microprocessor-based controller executing computer software commands stored in associated memory. In response to humidity or temperature values provided via a user interface 133, for example, and other inputs, the master controller 125 determines when (or to what level) to energize the heater plate 131 to heat the water 130 within the humidification chamber 129.

Any suitable patient interface may be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks, and nasal masks), cannulas, and nasal pillows. A temperature probe 135 may connect to the inspiratory tube 103 near the Y-piece 113, or directly to the Y-piece 113 or the patient interface 115. The temperature probe 135 monitors the temperature of the flow of gases near or at the patient interface 115. A heating filament (not shown) may be used to adjust the temperature of the patient interface 115, the Y-piece 113, and/or the inspiratory tube 103 to raise the temperature of the flow of gases above the saturation temperature, thereby reducing the opportunity for unwanted condensation.

In FIG. 1, exhaled gases are returned from the patient interface 115 to the gases source 105 via the expiratory tube 117. The expiratory tube 117 may have a temperature probe and/or heating filament, as described above with respect to the inspiratory tube 103, integrated with it to reduce the opportunity for condensation. Furthermore, the expiratory tube 117 need not return exhaled gases to the gases source 105. Alternatively, exhaled gases may be passed directly to ambient surroundings or to other ancillary equipment, such as an air scrubber/filter (not shown). In certain embodiments, the expiratory tube 117 is omitted altogether.

The system of FIG. 1 may be readily adapted for other applications involving the supply of a heated and/or humidified gas flow to a user or patient, including but not limited to laparoscopy, ventilation, and the like. Such applications may use alternative gases, operating parameters (e.g., flow, pressure, temperature, or humidity) and patient interfaces.

Example embodiments described herein below may be configured for incorporation in the system of FIG. 1, or a similar system, and the further description should be read in combination with the disclosure relating to FIG. 1.

Figure 2A:
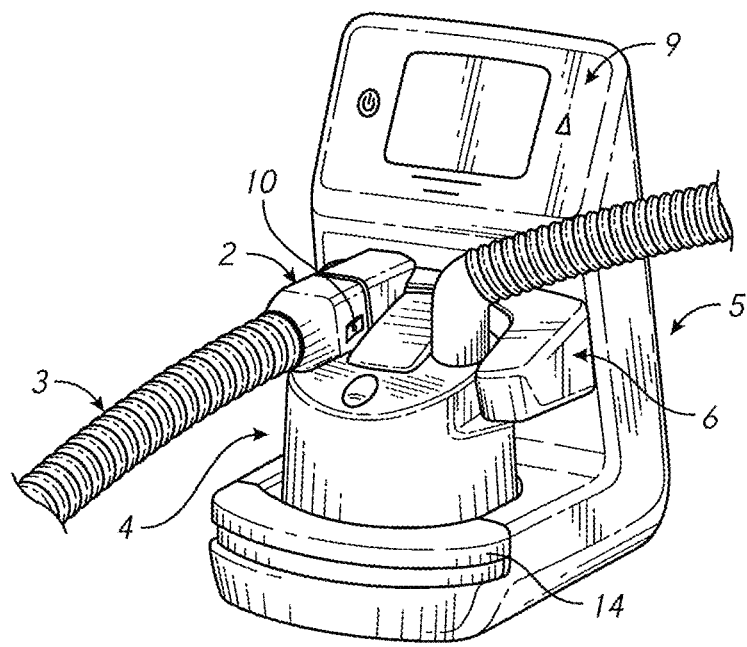
FIGS. 2A and 2B are perspective views of an example embodiment of a humidification system, with some features removed in FIG. 2B to show additional detail.
Figure 2B:
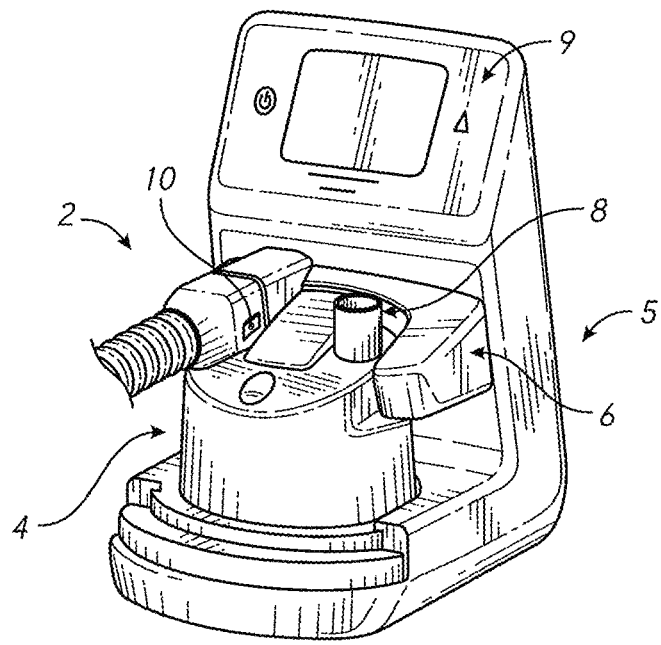
Figure 4:
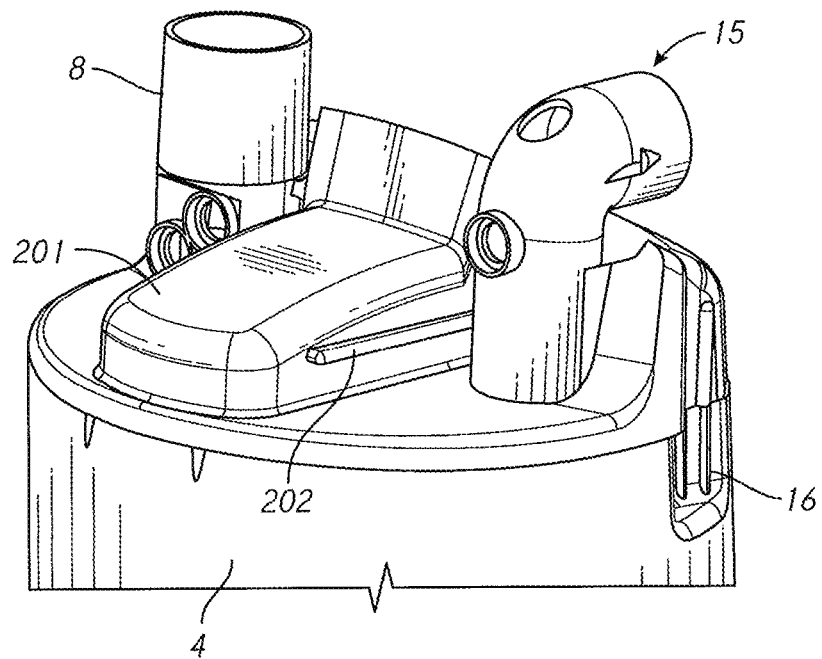
FIGS. 4 and 5A to 5F are alternative views of an example embodiment of a humidification chamber.

FIGS. 2A and 2B illustrate a humidification apparatus 1 according to an example embodiment. In FIG. 2B, some portions are removed to show additional detail. The apparatus includes a circuit connector 2 that pneumatically connects a medical tube or conduit 3 to an outlet 15 of a humidification chamber 4. As shown in FIG. 4, the outlet 15 may terminate in a substantially horizontal portion that is angled away from a base unit 5 when the humidification chamber 4 is installed on the base unit 5. The conduit 3 may be an inspiratory limb of a patient circuit, i.e., configured to deliver humidified gases to a user, such as via a patient interface (not shown). An inlet 8 of the humidification chamber 4 is configured to be fluidly connected to a source of pressurised gas. This may be positioned remote from the humidification apparatus 1 or form an integral part thereof, although it may be detachable therefrom. For example, the inlet 8 may be pneumatically coupled to a motorised fan in or associated with the base unit 5 that drives gases through the inlet 8.

The circuit connector 2 further facilitates electrical connection to the base unit 5 via a coupler 6. The coupler 6 may be integrally formed with the base unit 5 or may be a separate, replaceable module or cartridge. The ability to change modules may advantageously be used to enable use of different forms of humidification chamber and/or circuit connector. Additionally or alternatively, by comprising control circuitry, the module may be changed to alter the operation of the humidification apparatus 1. The conduit 3 may comprise one or more resistive heating wires that provide for heating of gases flowing through the conduit and/or sensor wires that electrically or otherwise facilitate communication of signals relating to one or more parameters of the system. Thus, the term "electrical connection" is used to distinguish from "pneumatic connection" and should not be construed in a limiting way. For example, light signals via optical fibres may be communicated. Consequently, the circuit connector 2 may more generally communicatively and/or electrically connect the conduit 3 (and any associated peripheral equipment, such as sensors, for example) to the base unit 5, such as via the coupler 6.

The circuit connector 2 may include at least one button or switch 10, which may be manually depressed to enable the circuit connector 2 (and hence also the conduit 3) to be disconnected from the humidification chamber 4. As will become apparent herein, the circuit connector 2 and the outlet 15 of the humidification chamber 4 may become lockably engaged on connection therebetween with the at least one button or switch 10 being used to subsequently allow for disengaging the circuit connector 2 from the humidification chamber 4. Any suitable connection may be used.

The base unit 5 further includes a panel 9 which may be used to mount a user display and/or controls. For example, various dials, switches, and other input means may be used to control operation of the device. Additionally or alternatively, a touch screen display may be used. The user display may display parameters of the system, warnings in the event of any errors or malfunctions, or prompts where user action is required, etc. Where a touch screen display is used, the same display may be used to present information to a user and receive inputs from a user, at least in part.

Figure 3:
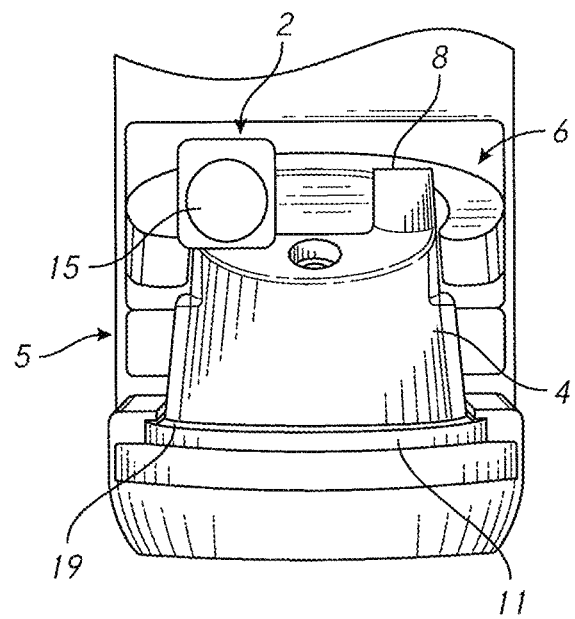
FIG. 3 is a front view of a portion of the humidification system shown in FIG. 2B.

The base unit 5 includes a heater plate 11 as shown in FIG. 3, which is controllably powered to heat the contents of the humidification chamber 4. To achieve more rapid heating, the humidification chamber 4 may comprise a base plate 19 formed from a highly heat conductive material. Further, to ensure a good connection between the base plate 19 of the humidification chamber 4 and the heater plate 11, the two surfaces may be biased towards each other. For example, according to one embodiment, a lip 12 extends outwards from, or proximate to, the base plate 19 of the humidification chamber 4 and is received under a projecting rim 13 of the base unit 5 as the humidification chamber 4 is slid onto the base unit 5. The heater plate 11 may be spring mounted such that the heater plate 11 is urged upwards into the base plate 19 of the humidification chamber 4, with the lip 12 acting against the projecting rim 13.

Referring again to FIG. 2A, the base unit 5 further includes a sprung latch bar 14. To engage the humidification chamber 4 with the base unit 5, the latch bar 14 is first depressed such that the lip 12 is able to be received under the projecting rim 13. This may be conveniently performed by positioning the base plate 19 of the humidification chamber 4 on the latch bar 14 and pressing the humidification chamber 4 downward and then toward the rear of the base unit 5. When the humidification chamber 4 is fully engaged with the base unit 5, the latch bar 14 can raise and act as a mechanical stop to prevent unintended removal of the humidification chamber 4 from the base unit 5. To disengage the humidification chamber 4 from the base unit 5, the latch bar 14 must first be depressed and then the humidification chamber 4 pulled away from the base unit 5 by sliding the base plate 19 of the humidification chamber 4 across the surface of the heater plate 11 and then onto the latch bar 14. As shown, the humidification chamber 4 may include gripping portions 16 that make it easier for a user to grip the humidification chamber 4 as it is pulled away from the base unit 5.

Referring to FIG. 4, the outlet 15 of the humidification chamber 4 may be oriented so as to be substantially parallel to the direction of motion of the humidification chamber 4 as it is slid on or off of the base unit 5, at least at the end of the outlet 15 distal from the humidification chamber 4. By configuring the apparatus in this way, it is possible to assemble the circuit connector 2, the humidification chamber 4, and the base unit 5 by either engaging the humidification chamber 4 with the base unit 5 and then attaching the circuit connector 2 to the outlet 15 of the humidification chamber 4, or attaching the circuit connector 2 to the outlet 15 of the humidification chamber 4 and then engaging the humidification chamber 4 with the base unit 5. The latter assembly option is made even simpler to follow because the circuit connector 2 and the outlet 15 are configured to lockably engage, which prevents separation of the circuit connector 2 from the outlet 15 while the humidification chamber 4 is slid onto the base unit 5. Additionally, like the latter assembly option, the conduit 3 and the humidification chamber 4 may be preassembled for shipping, thereby eliminating one step from the setup process. Irrespective of the order of assembly, electrical or other connections between the conduit 3 and/or the circuit connector 2 to the coupler 6 and/or the base unit 5 may be made as the circuit connector 2 engages with the coupler 6.

Similarly, disassembly may be performed in different sequences. More particularly, the circuit connector 2 may firstly be removed from the outlet 15 of the humidification chamber 4, followed by removal of the humidification chamber 4 from the base unit 5. Alternatively, the humidification chamber 4 may be removed from the base unit 5 while the circuit connector 2 is still attached to the outlet 15 of the humidification chamber 4. The latter option may advantageously help reduce the likelihood of a spill of fluids during disassembly and disposal of the consumables from the base unit 5.

Guide Features

To facilitate engagement of the circuit connector 2, the humidification chamber 4, and the base unit 5 on assembly thereof, various guides may be provided to control the orientation and/or position thereof relative to one another. More particularly, to enable the humidification chamber 4 to be slid into engagement with the base unit 5 and the coupler 6, various orientation features may be provided on the humidification chamber 4 and/or the coupler 6 such that, particularly when the circuit connector 2 is attached to the outlet 15, the component parts are brought readily and easily into alignment. For example, the humidification chamber 4 is able to be brought into full engagement with the base unit 5 such that the circuit connector 2 is also brought into engagement with the coupler 6. As is disclosed herein below, the circuit connector 2 and/or the coupler 6 may additionally or alternatively include orientation features to help ensure that the circuit connector 2 is connected to the humidification chamber 4 with the circuit connector 2 properly oriented to allow for easy coupling of the circuit connector 2 and the humidification chamber 4 to the base unit 5 and the coupler 6.

FIGS. 5A to 5F are various alternative views of an example embodiment of the humidification chamber 4. FIGS. 6A to 6C are alternative views of the coupler 6. As shown in FIGS. 5A to 5F, the humidification chamber 4 may include a nose portion 201 and guide wings 202. These features are configured to engage with a contoured recess 301 and slots 302, respectively, in the coupler 6 (see FIGS. 6A to 6C).

Further disclosure will make reference to a coordinate system in which the Z-axis extends vertically from the heater plate 11, the Y-axis is aligned in the direction of engagement of the humidification chamber 4 with the base unit 5, and the X-axis is perpendicular to both the Z- and Y-axes. Further, a width of the nose portion 201 is defined along the X-axis, a length of the nose portion 201 is defined along the Y-axis, and a height of the nose portion 201 is defined along the Z-axis.

In one embodiment, the nose portion 201 has a smaller width at a first end than at a second end of the nose portion 201, the first end of the nose portion 201 being configured to be received first in the recess 301. This provides some tolerance as to the position of the humidification chamber 4 along the X-axis (as well as rotationally about the Z-axis), in order for the nose portion 201 to be initially received in the recess 301. Further, the wider second end of the nose portion 201 may serve to refine the location of the nose portion 201 (and hence also the humidification chamber 4) along the X-axis (and rotationally about the Z-axis) in that the spacing or tolerance between the nose portion 201 and the recess 301 becomes reduced, thereby reducing the extent of relative movement.

In the embodiment shown, the recess 301 is configured such that the inclined sidewalls of the nose portion 201 abut corresponding and similarly inclined sidewalls of the recess 301. Having the sidewalls of the nose portion 201 and the sidewalls of the recess 301 configured in this manner controls the position of the humidification chamber 4 not only along the X-axis but also rotationally about the Y- and/or Z-axes, since movement of the nose portion 201 along the X-axis in at least two locations along the length of the nose portion 201, and also along the height of the nose portion 201, is substantially inhibited.

It is, however, possible to achieve some of these benefits where the sidewalls of the nose portion 201 do not abut the sidewalls of the recess 301. For example, if the nose portion 201 is configured as shown, but the sidewalls of the recess 301 are substantially parallel along their length and spaced apart by a distance greater than the greatest width of the nose portion 201 at the second end thereof, the configuration will still assist with initial insertion of the nose portion 201 into the recess 301 and at least significantly restrict movement of the nose portion 201 along the X-axis at the second end of the nose portion 201, although some rotational movement about the Z-axis may be possible. A similar result is achieved if the sidewalls of the nose portion 201 are substantially parallel and the recess 301 narrows along its length along the Y-axis from its opening to a width at least as great as that of the nose portion 201.

The nose portion 201 in combination with the recess 301 may additionally or alternatively provide tolerance along at least the Z-axis with regards to the initial placement of the humidification chamber 4. Further, according to particular embodiments, the nose portion 201 and the recess 301 may cooperate to refine the location of the humidification chamber 4 along the Z-axis and/or rotationally about the X- and/or Y-axes.

This tolerance is provided in a similar manner to the tolerance in the X-direction. As shown for example in FIG. 5C, the height of the nose portion 201 is lower at the first end than at the second end, the height being measured from the base plate 19. As shown in FIG. 6B, the recess 301 is similarly contoured, thereby providing for easy initial insertion followed by the refinement of position along the Z-axis on continued insertion of the humidification chamber 4 into full engagement with the base unit 5. Similar to the description regarding width-wise tolerance along the X-axis, the opposing walls of the substantially downwardly facing underside of the recess 301 may not abut along the length thereof with the upwardly facing topside of the nose portion 201. For example, one or the other may be orientated to be substantially parallel to the heater plate 11 with similar drawbacks to those mentioned previously. More particularly, while initial insertion may be facilitated, the degree of refinement of the position of the humidification chamber 4 along the Z-axis may be reduced and there may be less control to ensure that the base plate 19 is parallel to the heater plate 11.

In some embodiments, the engagement of the guide wings 202 with the slots 302 provides sufficient movement restriction to reduce the need for alignment and engagement of the base plate 19 with the heater plate 11 via the projecting rim 13. In some configurations, the base unit 5 may not include a projecting rim 13. In some embodiments, the nose portion 201 may be provided in the absence of the guide wings 202. However, the use of the guide wings 202 is preferred, at least in embodiments in which the heater plate 11 is spring mounted, so as to improve control of the positioning of the humidification chamber 4 along at least the Z-axis and/or to ensure that the heater plate 11 is substantially parallel to the base plate 19. Conversely, the guide wings 202 may be provided in the absence of the nose portion 201, but such a configuration is less preferable, since the nose portion 201 may more readily assist in the initial locating of the humidification chamber 4 and also perform the initial coarse adjustment thereof to refine the position, with the possibility of the guide wings 202 then being used to further refine the position of the humidification chamber 4 along the Z-axis and controlling the orientation about at least the X- and Y-axes. Where the nose portion 201 is omitted, the guide wings 202 may for example be mounted on a substantially rigid mount that extends vertically from the humidification chamber 4, with the guide wings 202 extending laterally therefrom. The substantially rigid mount may be substantially planar, with a generally T-shaped cross-section. However, to increase strength and rigidity, the mount may comprise more substantial element(s) having thickness, but a thickness that does not generally bring the mount into direct contact with the coupler 6.

Figure 5A:
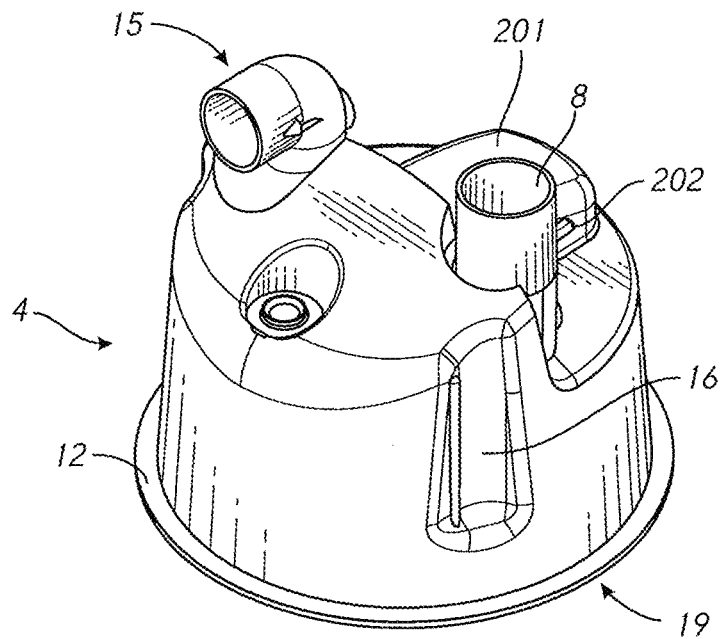
Figure 5B:
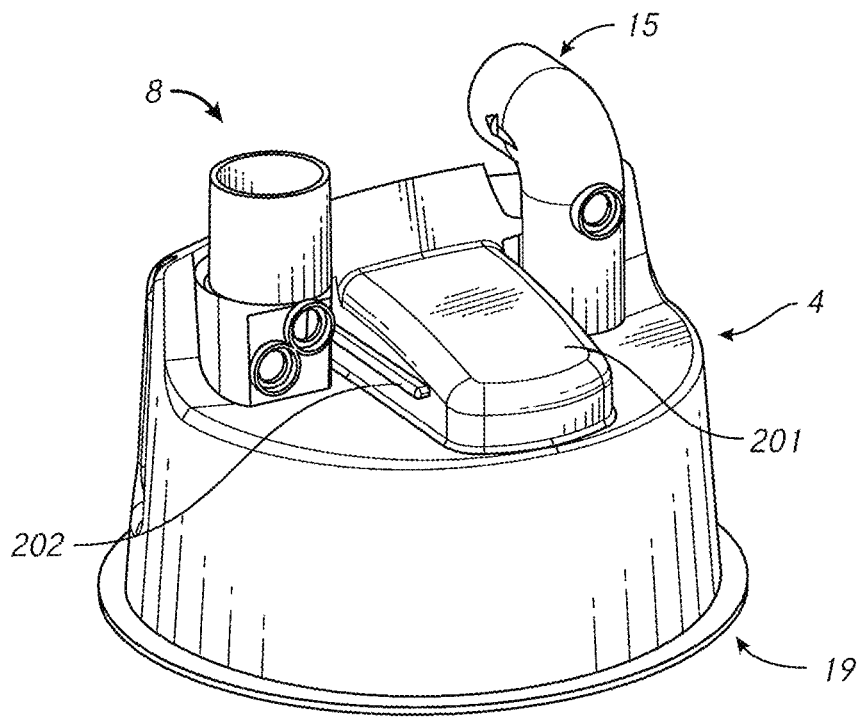
Figure 5C:
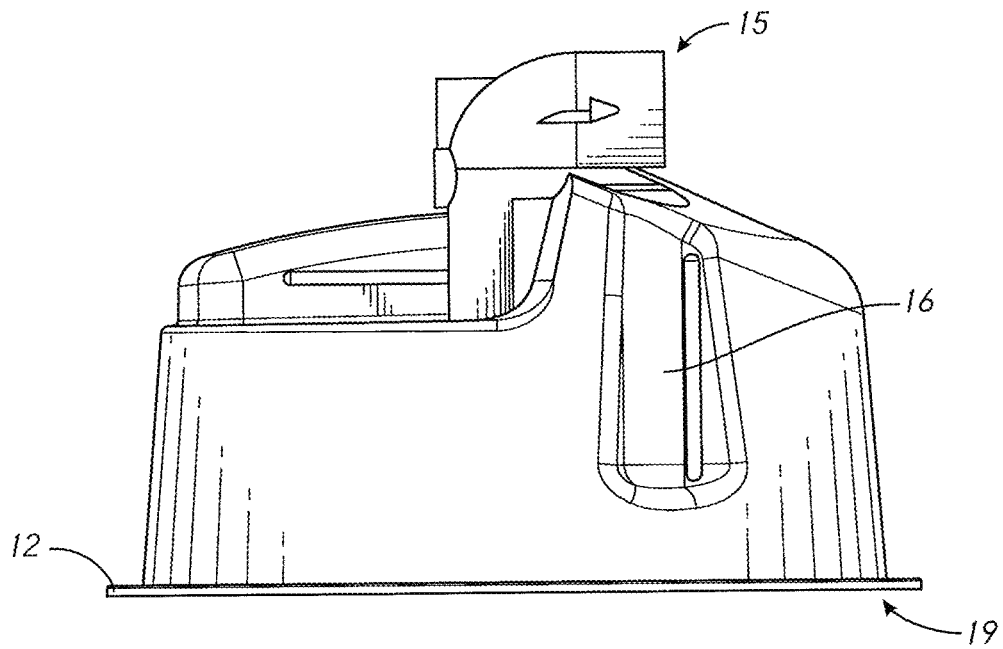
Figure 5D:
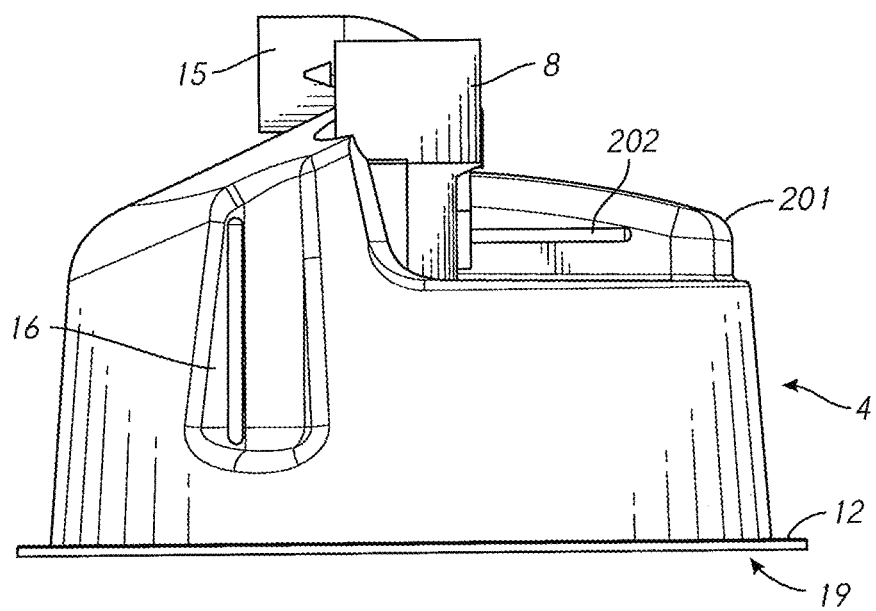
Figure 5E:
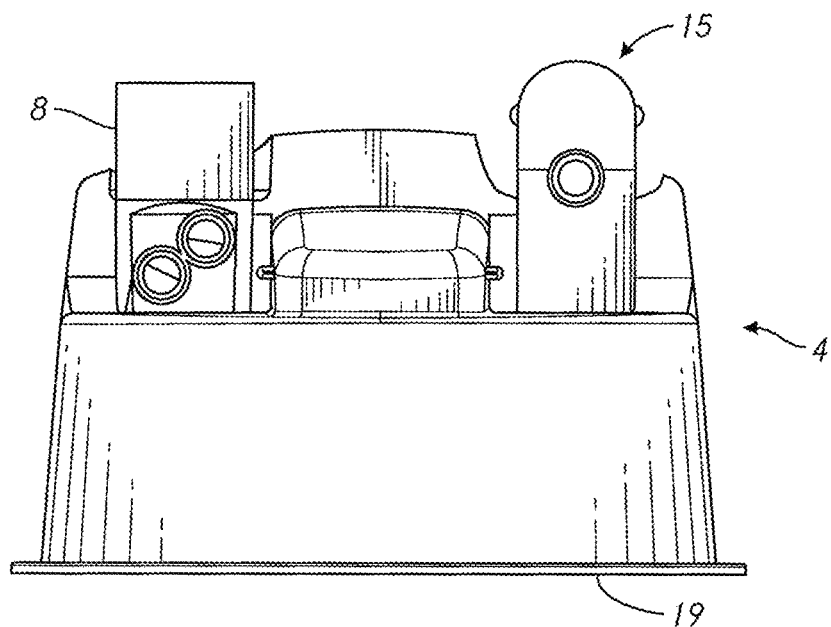
Figure 5F:
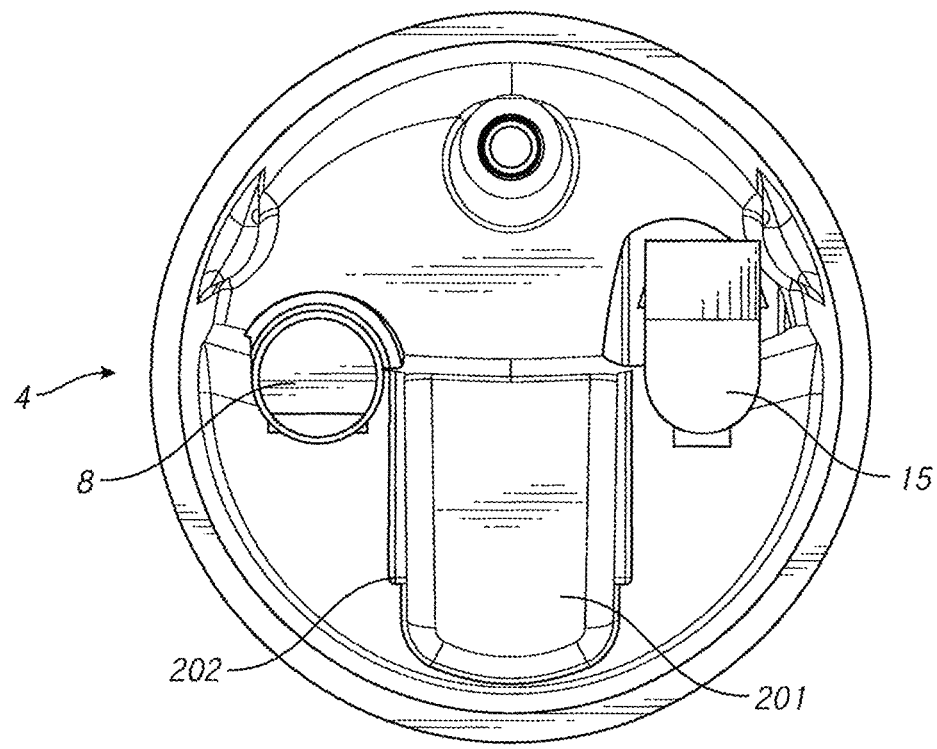
Figure 6A:
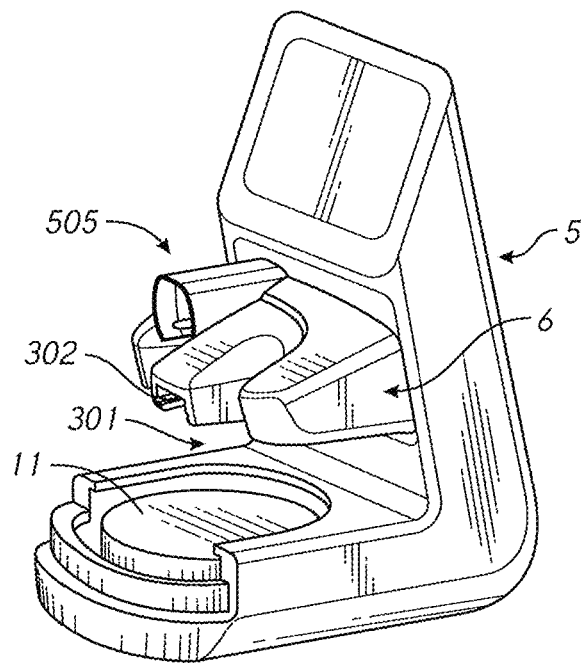
FIGS. 6A to 6C are alternative views of an example embodiment of a a humidification system including a coupler of or associated with a base unit.
Figure 6B:
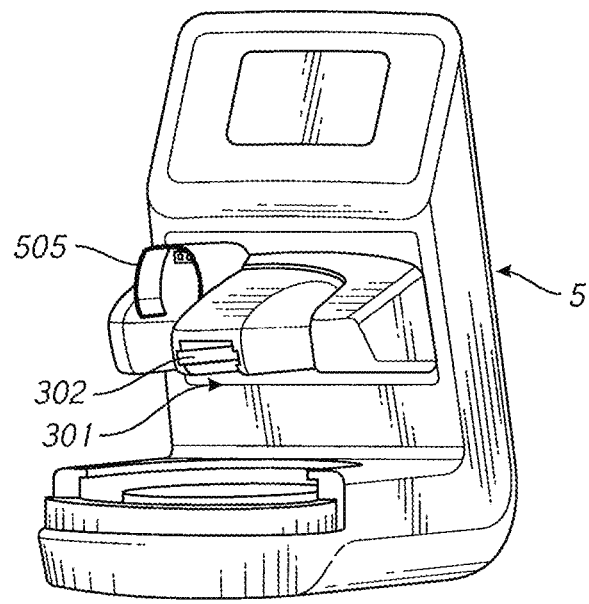
Figure 6C:
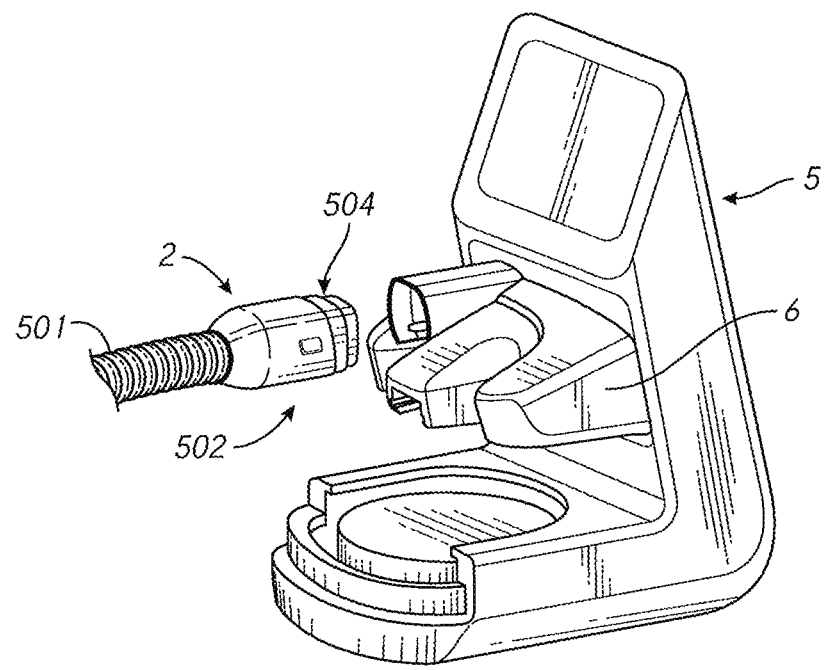

For example, as shown in FIG. 5B, the guide wings 202 do not extend right to the first end of the nose portion 201. Instead, they are spaced therefrom, thereby enabling initial engagement between the nose portion 201 and the recess 301 without engagement of the guide wings 202 with the slots 302, this only occurring on continued engagement of the humidification chamber 4 with the base unit 5 after the relative positions between the two have been refined.

As will be apparent, alternative guide means may be substituted. For example, the nose portion 201 may be in the form of a contoured recess and vice versa such that a contoured recess of the humidification chamber 4 receives a nose portion or projection of the coupler 6. Similarly the guide wings 202 may be substituted with grooves that receive wings or other projections on the coupler 6. Other arrangements that perform the same function may also be used.

Figure 7:
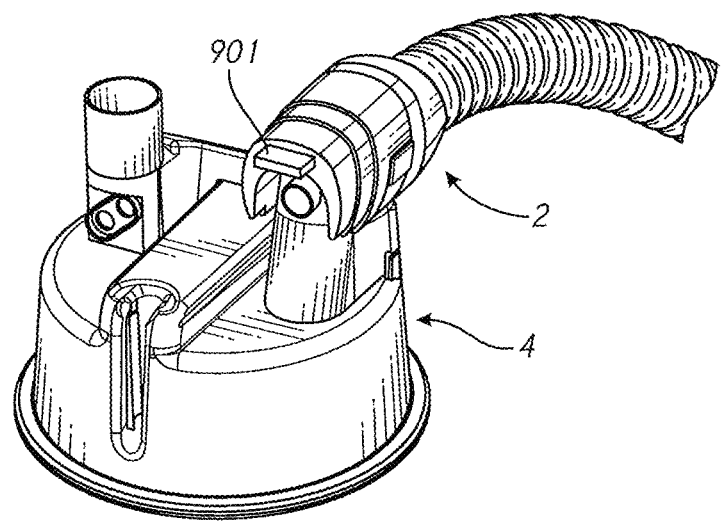
FIG. 7 illustrates an example embodiment of a circuit connector connected to a humidification chamber.
Figure 10B:
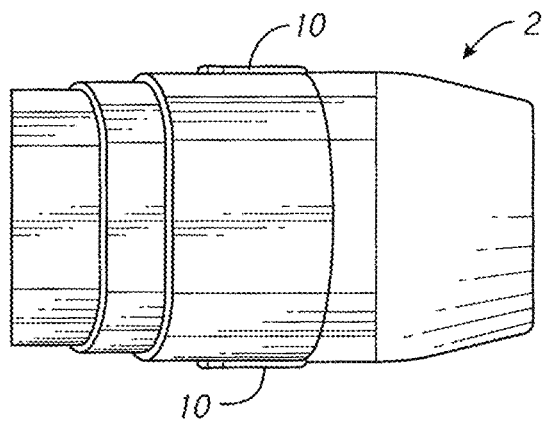
Figure 10C:
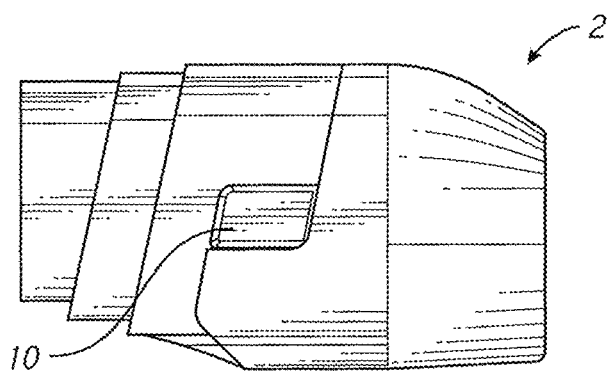
Figure 10D:
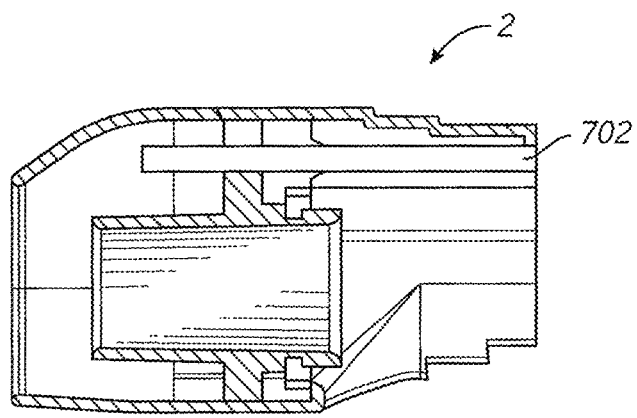
Figure 10E:
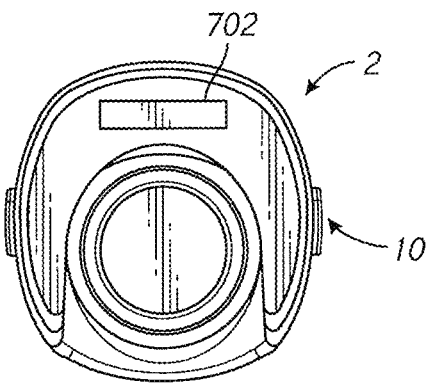

Also apparent from FIG. 7 and as shown more clearly in FIGS. 10A, 10D, and 10E, the circuit connector 2 may include a cutout 403 configured to accommodate a substantially vertical portion of the outlet 15. Again, this helps to ensure that the circuit connector 2 is correctly oriented as it is inserted onto the end of the outlet 15 since full insertion is only possible with correct alignment. Further, this arrangement provides for a stronger coupling and allows for electrical connection as will be described below. Again, at least an initial portion of the cutout 403 may be angled or curved such that the first part of the cutout 403 that receives the vertical portion of the outlet 15 is wider than the outlet 15, providing some tolerance as to the required initial alignment. However, where the outlet 15 is generally of a circular cross-section, this may not be required as some tolerance is inherently provided due to the circular shape of the outlet 15.

Figure 8A:
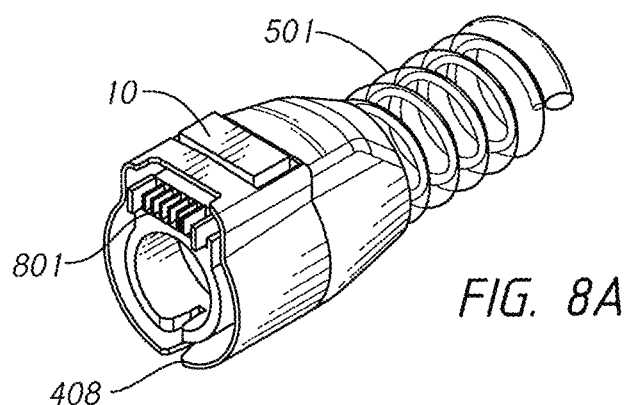
Figure 8B:
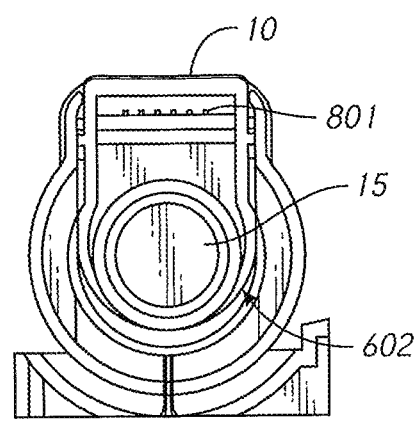
Figure 8C:
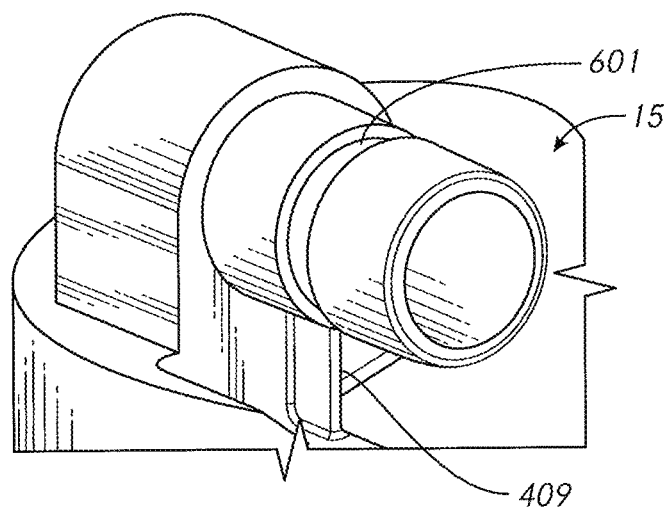

Referring to FIGS. 8A and 8C, the circuit connector 2 may additionally or alternatively include an angled cutout 408 that receives a similarly angled protrusion 409 on the outlet 15. Again this serves to obtain and secure orientation of the circuit connector 2 and the outlet 15 relative to one another.

Additionally or alternatively, guide means may be incorporated in the heater plate 11 and/or the base plate 19 of the humidification chamber 4. For example, a ridge in the heater plate 11 may be configured to be received in a slot in the base plate 19 of the humidification chamber 4, or vice versa.

Circuit Connector

A first embodiment of the circuit connector 2 is illustrated in FIGS. 2A, 2B, 6C, and 7. A first end of the circuit connector 2 (see FIG. 2B) is configured to receive and pneumatically seal an end of a respiratory tube or conduit 501 (see FIG. 6C).

The circuit connector 2 may comprise a main body 502 and an extending portion 504. The interior of the main body 502 defines a channel that connects the conduit 501 to the horizontal portion of the outlet 15 to provide a continuous flow passage when assembled. A seal (e.g., an O-ring, double O-ring, or lip seals) may be provided between the contact surfaces between the interior of the main body 502 and the exterior of the outlet 15 to prevent leakage of gases being delivered.

The coupler 6 is shown including a shroud 505 which receives and covers the extending portion 504. This may help to reduce or eliminate the likelihood of any spilled liquid coming into contact with electrical components of the circuit connector 2 and also serves to strengthen and rigidify the coupling. Further, the shroud 505 may assist in bringing the circuit connector 2 into engagement with the outlet 15 of the humidification chamber 4 and/or into engagement with the base unit 5. More particularly, the shroud 505 provides a visual indication as to where the circuit connector 2 should be positioned. Further, the shroud 505 may provide some physical control over the location of the circuit connector 2. For example, in the embodiment shown, at least the extending portion 504 of the circuit connector 2 is received against a portion of the wall of the shroud 505 opposing the heater plate 11. This may occur particularly where the heater plate 11 is spring-mounted so as to bias the heater plate 11 towards the shroud 505. Thus, at least the height (i.e., along the Z-axis) of the circuit connector 2 may be controlled. Having the shroud 505 provide a curved opposing wall may assist in locating the circuit connector 2 along the X-axis since the circuit connector 2 will be urged towards the center of the arc formed by the shroud 505. The physical locating function of the shroud 505 is yet further improved by having the shroud 505 define a wall that at least partially encloses the circuit connector 2 so as to control not only an upper limit for the position of the circuit connector 2 but an actual location thereof.

Figure 8D:
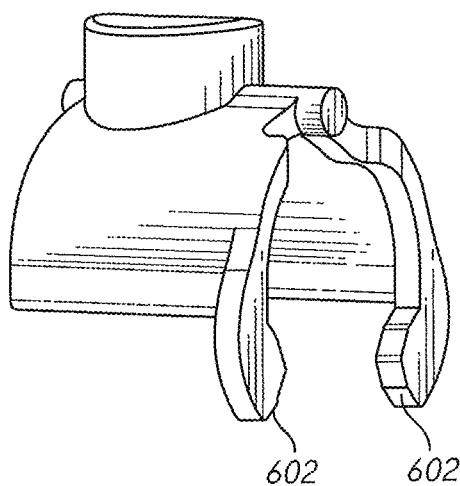
Figure 8E:
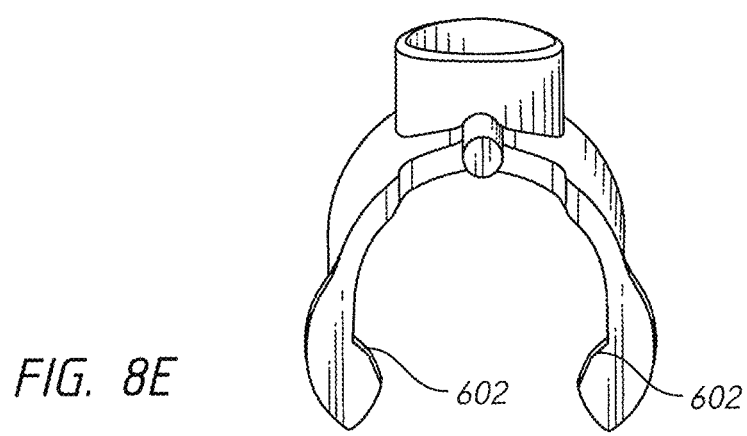

FIGS. 8A to 8C illustrate an embodiment of a lockable but releasable coupling between the circuit connector 2 and the outlet 15. The circuit connector 2 includes the button 10 that may be manually actuated such as by a thumb or finger to enable the circuit connector 2 to be removed from the outlet 15. The button 10 is formed from a resiliently elastic material and has a portion configured to be received in a recess 601 formed in the outer wall of the outlet 15. Depression of the button 10 disengages an engaging portion of the button 10 from the recess 601. FIGS. 8D and 8E illustrate an alternative embodiment where the button 10 is formed from a substantially rigid material but may be spring mounted. Depression of the button 10 acts against the spring and disengages an engaging portion 602 of the button 10 from recesses in an outer wall of the outlet 15.

FIGS. 9A and 9B illustrate an alternative embodiment where the button 10, or at least the engaging portion 602 thereof, is resiliently elastic whereby at least a portion of the button 10 deforms to disengage the engaging portion 602 from recesses 601 in the outlet 15.

Figure 10F:
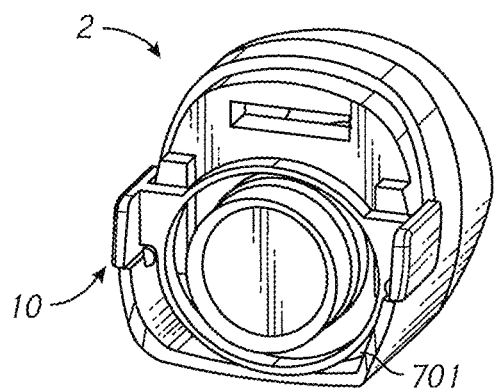
Figure 10G:
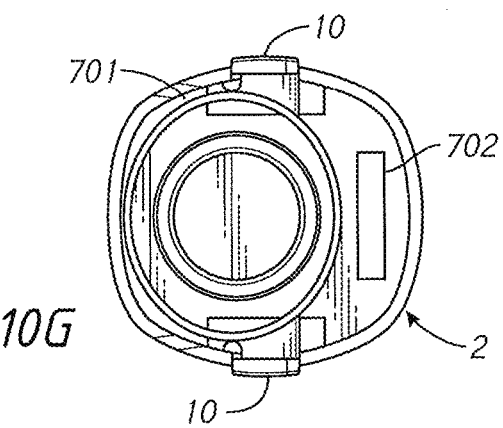
Figure 10H:
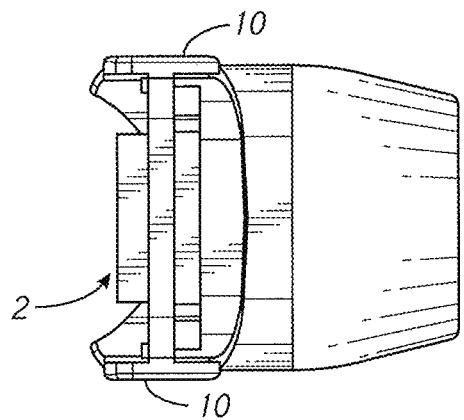
Figure 10I:
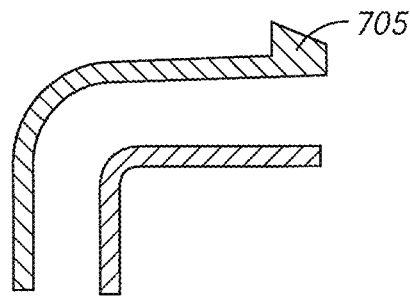
Figure 10J:
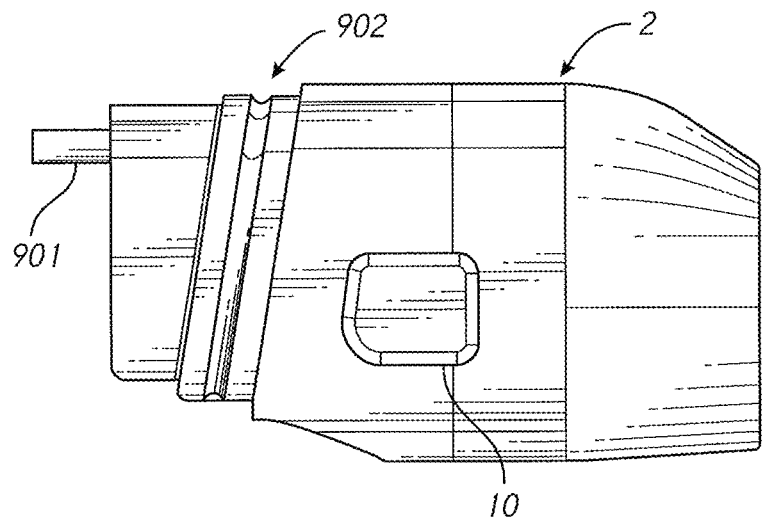
Figure 10K:
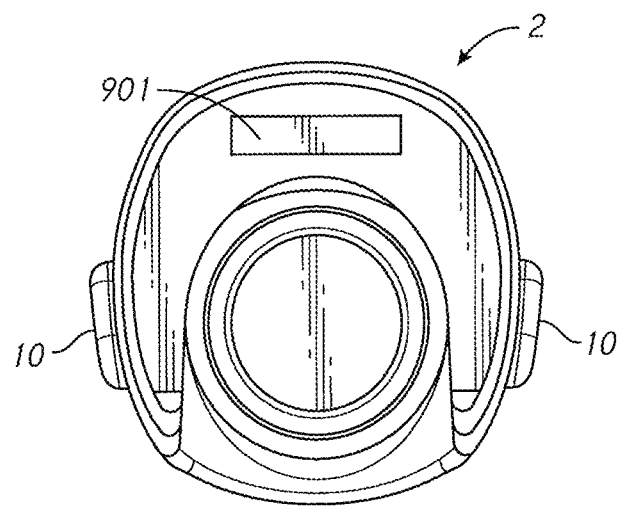

FIGS. 10A to 10H illustrate an alternative embodiment of the circuit connector 2. In FIGS. 10F to 10H, part of the circuit connector 2 is removed to show additional detail. According to this embodiment, the buttons 10 are positioned on sides of the circuit connector 2, as this may be more convenient in being placed at natural contact points for a user when attempting to disconnect the circuit connector 2 from the outlet 15. The buttons 10 are integral with or operably coupled to an elastically deformable ring 701. Depression of the buttons 10 disengages the ring 701 from recesses formed in at least one of the upper and lower outer surfaces of the outlet 15, allowing the circuit connector 2 to be removed. FIGS. 10A to 10H also show a cavity 702 for housing electrical or other connections. As alternative to recesses, protrusions 705 may be used in the outlet 15 as shown in cross-section in FIG. 10I. This applies to this and other embodiments disclosed herein. In some such embodiments, when the circuit connector 2 is coupled to the outlet 15, the top of the ring 701 rests behind (or closer to the base unit 5 than) the protrusion 705. To disengage the circuit connector 2 from the outlet 15, the buttons 10 are depressed to deform the ring 701 such that the top of the ring 701 rises above the level of the protrusion 705 and then the circuit connector 2 can be removed from the outlet 15. A further embodiment is shown in FIGS. 10J and 10K wherein the electrical terminal is in the form of an edge card 901. Further shown is a groove 902 configured to receive a seal such as an o-ring.

Electrical Connections

Figure 6D:
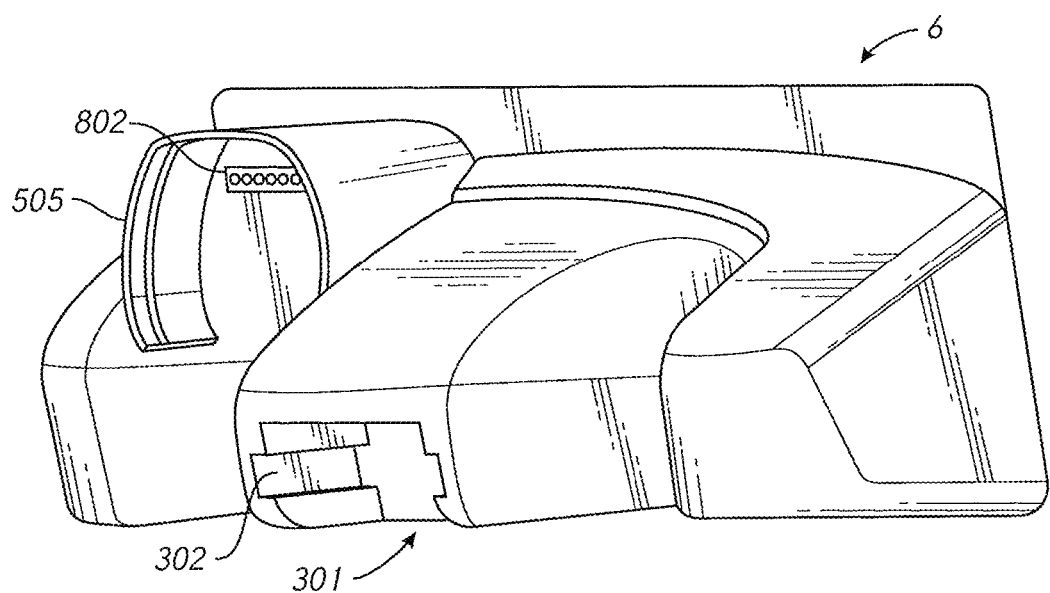
FIG. 6D illustrates the coupler of FIGS. 6A to 6C.

Example electrical connections 801 are shown in FIGS. 8A and 8B. The electrical connections may be provided in the extending portion 504 of the circuit connector 2 such that they extend beyond the pneumatic connection and electrically and/or communicatively couple to a cooperative connector 802 on the coupler 6 as shown in FIG. 6D. As shown in FIGS. 8A and 8B, the electrical and other connections may be formed by blade contacts that are received in respective recesses in the coupler 6 that house contacts for connecting thereto. Other connectors such as pins may alternatively be used but blade contacts are advantageous in providing some tolerance in the exact relative positioning of the blades in the recesses. In the embodiment shown, some vertical tolerance is provided for.

According to an alternative embodiment, the electrical contacts comprise one or more pogo or spring pin contacts that include spring-mounted pins housed in passages that allow them to vary the extent to which they protrude from the housing, thereby providing tolerance in the relative positions of the circuit connector 2 and the coupler 6 along the axes of the pins. Further, the ability for the pins to become depressed may make insertion of the pins into the apertures that house cooperating or mating connectors easier.

According to another alternative embodiment, the electrical connections comprise edge card connectors or card edge connectors, wherein a first part of the connector has one or more conductive tracks provided on a printed circuit board and configured to make contact with one or more pins of a second part of the connector.

Alternative Embodiments

Figure 11A:
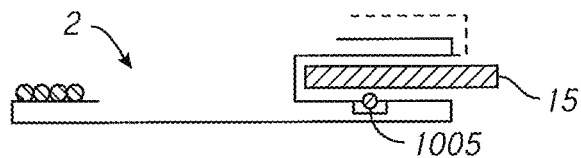
Figure 11A:
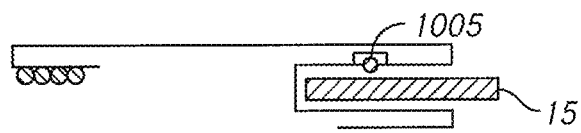

FIG. 11A is a cross-sectional view of an alternate embodiment of the circuit connector 2 engaged with the outlet 15 of the humidification chamber 4. In this embodiment, the circuit connector 2 has a male connection such that at least a portion of the circuit connector 2 is received inside the outlet 15. An o-ring 1005 or other seal is used to seal between the male parts and the inside wall of the outlet 15.

Figure 11B:
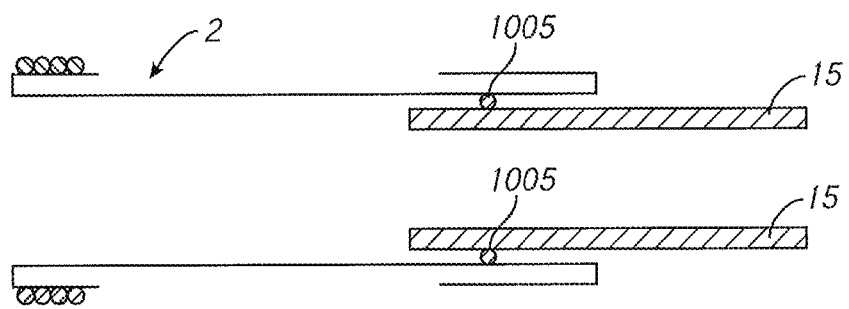

FIG. 11B shows a view similar to that of FIG. 11A but modified such that the outlet 15 is configured as the male part that mates with the inner wall of the inlet of the circuit connector 2. Again, an o-ring 1005 or other seal may be be used to reduce or eliminate the likelihood of leakage.

Figure 12:
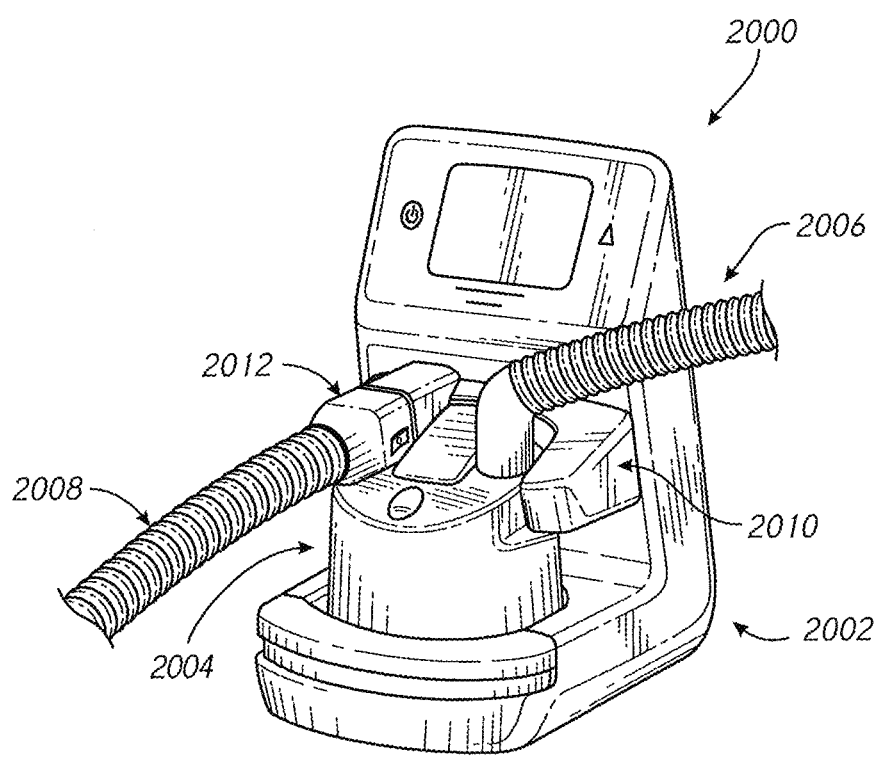
FIG. 12 is a perspective view of an example embodiment of a humidification system.
Figure 13:
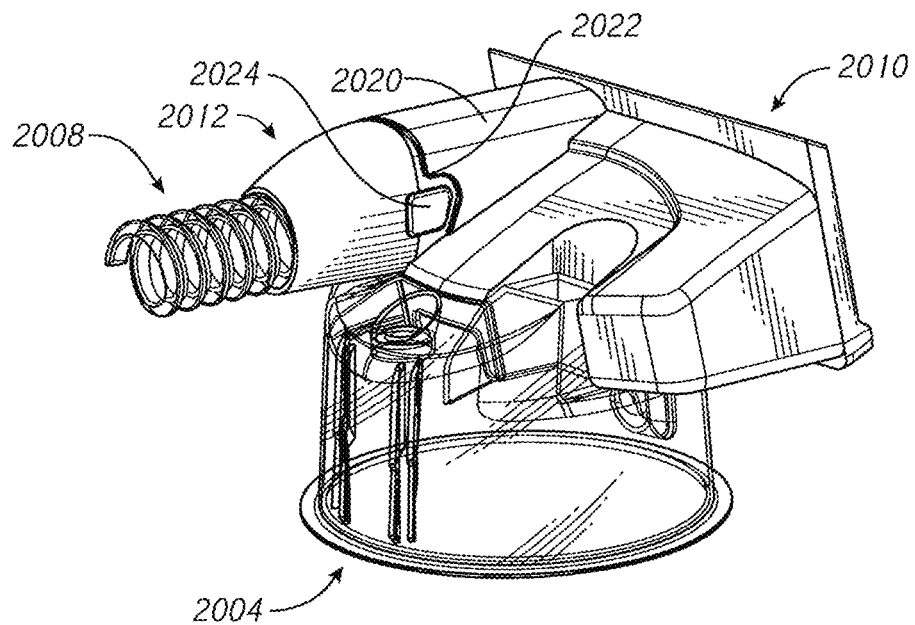
FIG. 13 is an alternative view of a chamber, cartridge, and connector of the humidification system of FIG. 12.

With reference now to FIG. 12, a humidification system 2000 is illustrated therein. The humidification system 2000 may have any suitable configuration. The humidification system 2000 may be used in conjunction with other components for supplying heated and/or humidified gases for continuous, variable, or bi-level positive airway pressure (PAP) or any other type of respiratory therapy. It also may be used in conjunction with devices for surgical applications, such as for laparoscopic surgery or the like.

The illustrated humidification system 2000 comprises a base 2002 that receives a humidification chamber 2004. A supply conduit 2006 and a delivery conduit 2008 may be connected to the humidification chamber 2004. The supply conduit 2006 may deliver to the humidification chamber 2004 a flow of gases to be humidified. The delivery conduit 2008 may deliver to a user or patient the flow of gases after they have been humidified within the chamber 2004.

In some configurations, the base 2002 includes an electrical connection to one or both of the supply conduit 2006 and the delivery conduit 2008 (e.g., an inspiratory limb). In the illustrated configuration, the base 2002 comprises a cartridge or coupler 2010. The cartridge or coupler 2010 may be integrally formed with the base 2002 or may be a separate, replaceable module or cartridge. One or both of the conduits 2006, 2008 may include one or more wires. The wires may comprise one or more resistive heating wires that provide for heating of the conduit wall and/or gases flow. The wires may comprise one or more sensor wires that facilitate the communication of signals relating to one or more parameters of the system 2000. Thus, the term "electrical connection" is used in its broadest meaning and should include light signals via fibre optics or the like, for example but without limitation.

The illustrated delivery conduit 2008 comprises a connector 2012. The connector 2012 facilitates the electrical connection between the conduit 2008 and the cartridge 2010. The connector 2012 also facilitates a pneumatic connection between the conduit 2008 and the chamber 2004. Thus, the connector 2012 facilitates both the electrical connection between the base 2002 (through the cartridge 2010) and the conduit 2008 as well as the pneumatic connection between the chamber 2004 and the conduit 2008.

The connector 2012 in the illustrated configuration is constructed to connect in a horizontal direction (i.e., a direction parallel to a direction of insertion of the chamber 2004 into or onto the base 2002). The connector 2012 is constructed to connect electrically to the cartridge 2010 in the horizontal direction. The connector 2012 is constructed to connect pneumatically to the chamber 2004 in the horizontal direction. The connector 2012 is constructed to connect to both the cartridge 2010 and the chamber 2004 in the same horizontal direction.

Cartridge or Coupler

Figure 14:
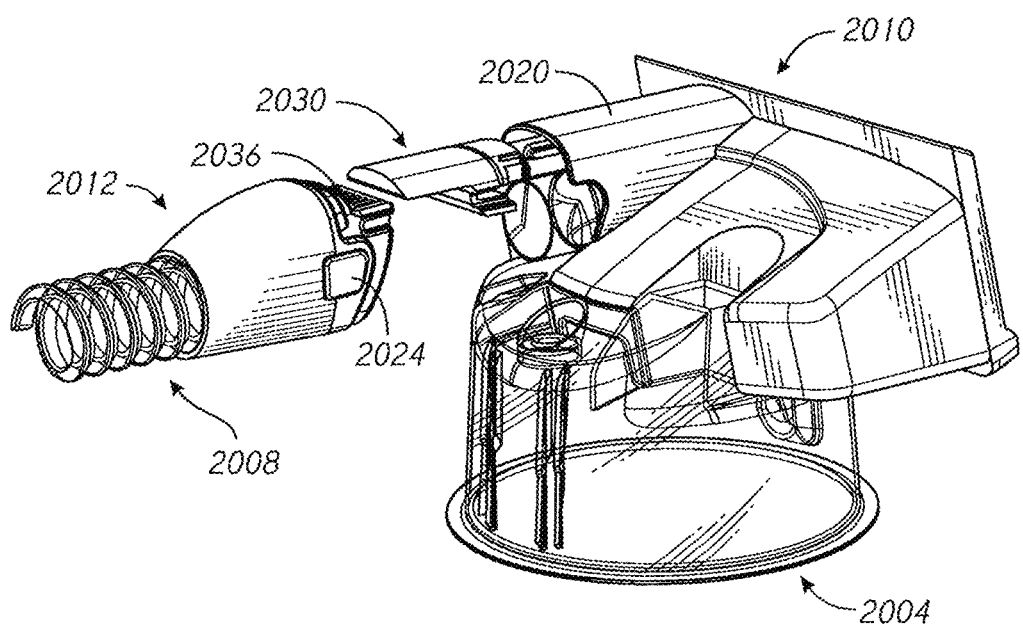
FIG. 14 is an exploded view of FIG. 13 showing an insert block.
Figure 15:
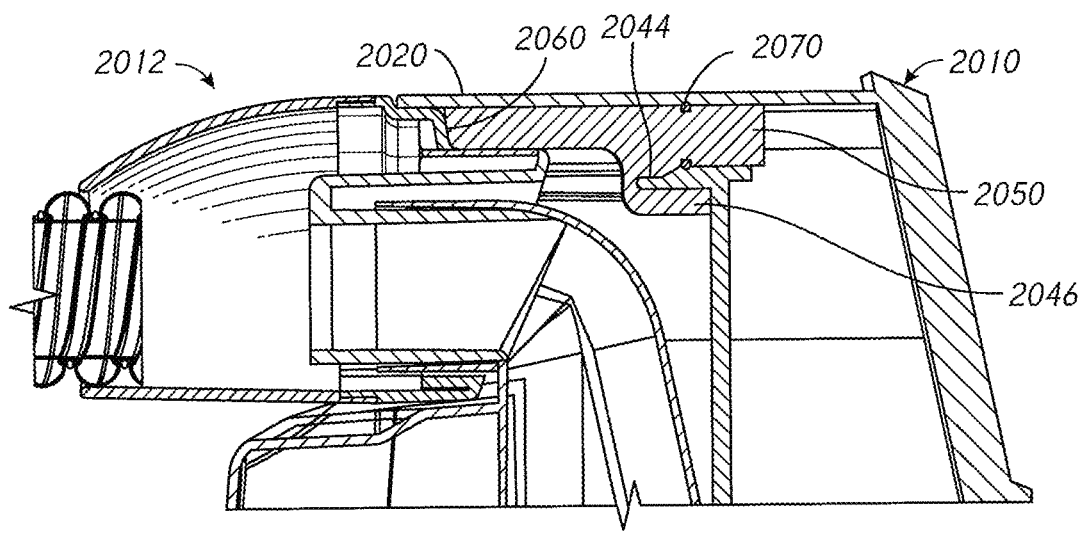
FIG. 15 is a sectional view of the assembly of FIG. 13.
Figure 16:
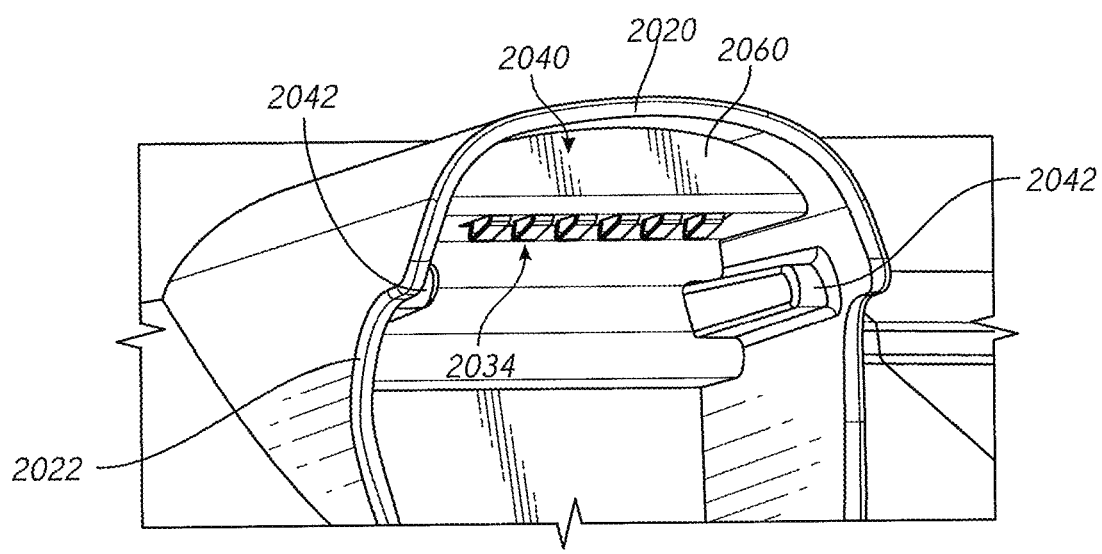
FIG. 16 is an enlarged perspective view of the cartridge and insert block of FIG. 13.

The connections between the cartridge or coupler 2010, the chamber 2004, and the connector 2012 are better shown in FIGS. 13 to 16. As illustrated, the cartridge 2010 may include a hood portion 2020 that overlies an electrical connector (e.g., an electrical junction 2034 as shown in FIG. 16) of the cartridge 2010. The hood portion 2020 may extend forward of the base 2002 in a generally horizontal direction.

The hood portion 2020 may include a recess 2022 along a vertically extending portion. The recess 2022 is sized, positioned and configured to receive a portion of the connector 2012 that comprises a release button 2024. In the illustrated configuration, at least a portion of the hood 2020 extends further along an upper portion of the connector 2012 (when connected to the cartridge 2010) from the base 2002 relative to the location of the release button 2024 on the connector 2012. Other configurations are possible.

Insert Block

With reference to FIG. 14, in the illustrated configuration, an insert block 2030 may facilitate the electrical connection between the connector 2012 and the cartridge 2010. In some configurations, droplets of water or other moisture may be present on the connector 2012. The insert block 2030 helps to isolate the cartridge 2010 from the water or other moisture while facilitating the desired electrical connection between the connector 2012 and the cartridge 2010.

The insert block 2030 may be mounted to the connector 2012 or to the cartridge 2010. In some configurations, the insert block 2030 is not mounted to either of the connector 2012 or the cartridge 2010. In the illustrated configuration, the insert block 2030 is mounted to the cartridge 2010. By mounting the insert block 2030 to the cartridge 2010, the likelihood of the insert block 2030 becoming misplaced during changing of the conduit 2008 or the like is significantly decreased. By not mounting the insert block 2030 to the connector 2012, changing of the conduit 2008 is simplified and there is less waste as compared to an insert block 2030 that might be discarded with the conduit 2008 following each use.

Figure 17:
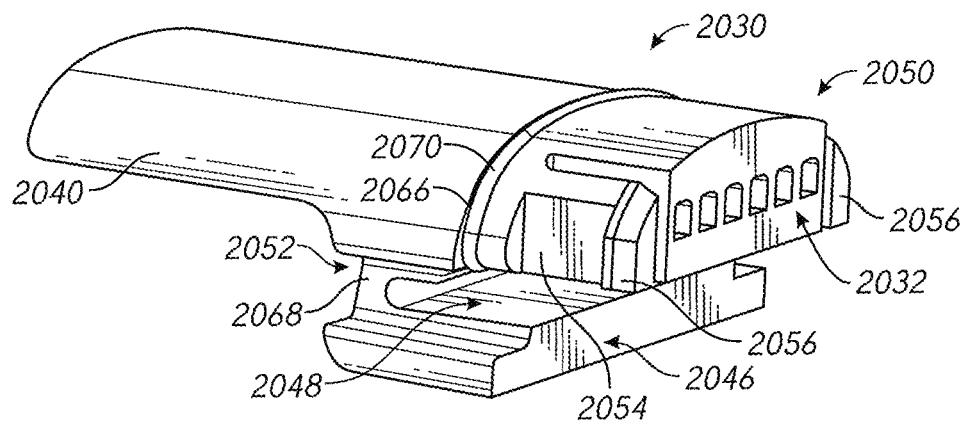
FIGS. 17 and 18 are perspective views of the insert block of FIG. 13.
Figure 18:
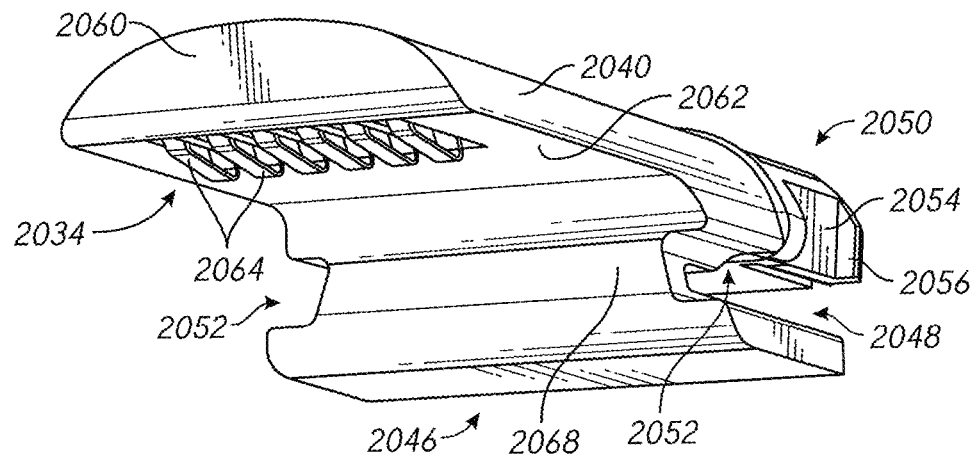

With reference to FIGS. 17 to 18, the insert block 2030 has a first electrical junction 2032 and a second electrical junction 2034. The first electrical junction 2032 is sized, positioned and configured to engage with an electrical connector of the cartridge 2010. The second electrical junction 2034 is sized, positioned and configured to engage with electrical contacts 2036 (see FIG. 14) of the connector 2012. The first electrical junction 2032 and the second electrical junction 2034 may be joined together in any suitable manner Advantageously, the insert block 2030 transforms a generally horizontal connection between the first electrical junction 2032 and an electrical connector of the cartridge 2010 into a generally vertical connection between the second electrical junction 2034 and the electrical contacts 2036 of the connector 2012.

The insert block 2030 comprises a body 2040. The body 2040 is sized and configured to be received within the hood 2020. In some configurations, the body 2040 is sized and configured to be retained within the hood 2020. In some configurations, the hood 2020 comprises one or more alignment features 2042. In the illustrated configuration, the alignment features 2042 of the hood 2020 comprise rails 2042. The rails 2042 may have any suitable configuration. In the illustrated configuration, two rails 2042 are aligned to each other on diametrically opposed sides of the hood 2020. Moreover, as illustrated in FIG. 15, the illustrated cartridge 2010 also comprises a flange 2044. The flange 2044 may be integrally formed with the rails 2042 or may be a separate feature from the rails 2042. The flange 2044 extends generally horizontally and projects forward from a rear wall of the cavity that receives the connector 2012. The flange 2044 is enshrouded by the hood 2020. In some configurations, the flange 2044 has a stepped configuration with a distal end having a reduced thickness relative to a proximal end, wherein the proximal end is closer to the rear wall of the cavity than the distal end.

The body 2040 includes a mounting boss 2046. A recess 2048 may be defined between the mounting boss 2046 and another portion of the body 2040 that extends to the first electrical junction 2032. The recess 2048 may be sized and configured to receive at least a portion of the flange 2044. In particular, an engagement portion 2050 of the body 2040 may be spaced apart from the mounting boss 2046 by the recess 2048. Other configurations are possible.

The mounting boss 2046 may include channels 2052. The channels 2052 may be sized, positioned and configured to receive the rails 2042. The channels 2052 may have a shorter length than the length of the rails 2042 such that a significant portion of the rails 2042 are exposed beyond the mounting boss 2046 when the insert block 2030 has been secured within the hood 2020.

The engagement portion 2050 of the body 2040 may comprise one or more retention elements 2054. In the illustrated configuration, the one or more retention elements 2054 may each comprise a deflectable tab. At least one deflectable tab 2054 may be positioned on each opposing side of the body 2040. In the illustrated configuration, the body 2040 has a deflectable tab 2054 disposed on each lateral side of the body 2040.

The tabs 2054 may include a catch element 2056. The catch element 2056 may extend laterally away from the body 2040. In some configurations, the catch element 2056 may extend generally normal from a recess that spaces at least a portion of the deflectable tab 2054 from the body 2040. In some configurations, a proximal portion of the deflectable tab 2054, including the catch element 2056, may be shaped to encourage deflection of the tab 2054 inwardly toward the body 2040 during insertion of the insert block 2030 into the hood 2020. For example, the proximal surface of the catch element 2056 may taper when viewed from the top.

The body 2040 includes a distal end 2060. Proximally of the distal end 2060, an upper surface of the body 2040 may be shaped to match the inner surface of the hood 2020. In the illustrated configuration, both are curved.

The distal end 2060 of the body 2040 may be recessed within the hood 2020. As shown in FIG. 15, the distal end 2060 may be shaped and configured to complement an adjoining end of the connector 2012. For example, in the illustrated configuration, the distal end 2060 of the body 2040 may taper slightly.

A contact surface 2062 may be positioned between the distal end 2060 and the mounting boss 2046. In the illustrated configuration, the contact surface 2062 faces downward. In some configurations, the contact surface 2062 is generally planar.

The contact surface includes one or more openings through which contact terminals 2064 may extend. The contact terminals 2064 may define at least a portion of the second electrical junction 2034. The contact terminals 2064 may have any suitable configuration.

In some configurations, the contact terminals 2064 are sprung terminals that have been configured to minimize or reduce surfaces to which water may adhere. In some configurations, the contact terminals 2064 are sprung terminals that have been configured to minimize or reduce surfaces upon which a cloth may catch during wiping or cleaning. In a relaxed state, the contact terminals 2064 advantageously protrude downward beyond the contact surface 2062. When compressed, the contact terminals 2064 may be at least partially deflected into the body 2040.

With reference to FIG. 17, in some configurations, the body 2040 may include an encircling groove 2066. The groove 2066 may be positioned rearward of a post 2068 that connects the mounting boss 2046 to the engagement portion 2050. In some configurations, the groove 2066 may receive a sealing component 2070. In some such configurations, the sealing component 2070 may be a seal, an o-ring or the like. In some configurations, neither the groove 2066 nor the sealing component 2070 are present.

With reference to FIG. 15, the insert block 2030 may be inserted into the hook 2020. During insertion, the rails 2042 are positioned within the channels 2052. The insert block 2030 is slid proximally until the flange 2044 is received within the recess 2048. If present, the sealing component 2070 may be compressed between the engagement portion 2050 and the surrounding portions of the cartridge 2010. During insertion, features on an inner surface of the hood 2020 may cause the tabs 2054 to deflect inwardly toward the body 2040 until the catch elements 2056 are proximal of the features on the inner surface, at which point the tabs 2054 may return to a relaxed state with the catch elements 2056 positioned proximally of the features on the inner surface. Any suitable configuration to secure the insert block 2030 within the hood 202 may be used. Once inserted and secured in position, the first electrical junction 2032 (e.g., receptacles) may be in electrical contact with corresponding elements (e.g., pins) of an electrical connector of the cartridge 2010. Once the insert block 2030 is installed, the second electrical junction 2034 (e.g., the terminals 2064) is easily accessed for drying, wiping, cleaning or the like. In addition, due to the configuration of the terminals 2064, coatings applied to the terminals 2064, or the like, water and other liquids are not likely to remain on or adhere to the terminals 2064.

Connector

With reference now to FIGS. 19 to 24, the connector 2012 will be described in further detail. The connector 2012 may be secured to the end of the conduit 2008 in any suitable manner.

Figure 24:
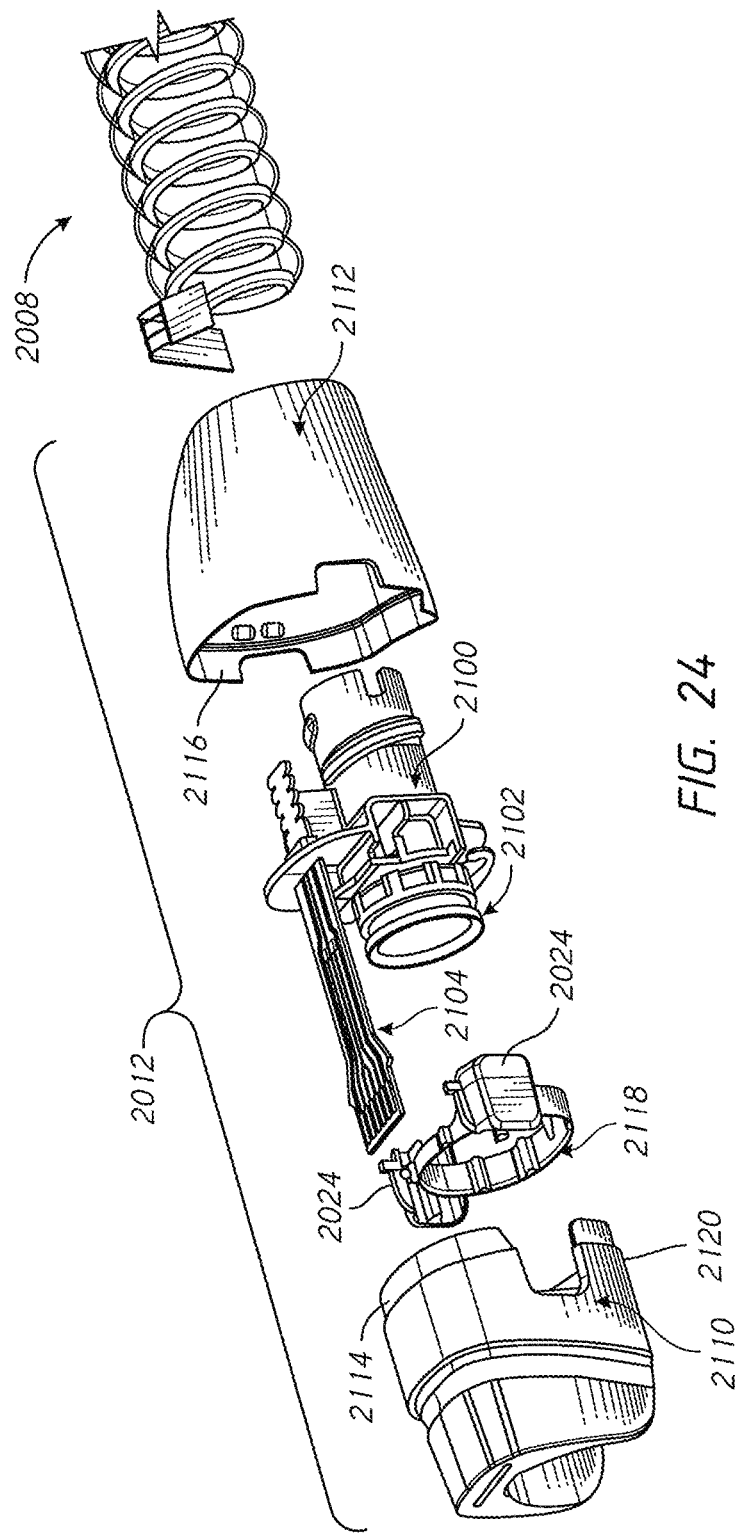
FIG. 24 is an exploded view of an example embodiment of a connector similar to that of FIG. 13, showing the components of the connector.

With reference to FIG. 24, the connector 2012 generally comprises an inner plug 2100. The conduit 2008 may be threaded onto the illustrated inner plug 2100 and secured thereto using overmoulding or any other suitable technique. In some configurations, a seal 2102 may be positioned on an outer surface of the inner plug 2100. The seal 2102 may be used to help form a pneumatic seal with an inner surface of a port of the chamber 2004.

The inner plug 2100 also carries a printed circuit board 2104. The printed circuit board 2104 may include contact pads 2106. The contact pads 2106 may have any suitable configuration. The contact pads 2106 are sized, positioned and configured to be brought into contact with the terminals 2064 of the second electrical junction 2034 of the insert block 2030. In the illustrated configuration, there are six contact pads 2106 that are spaced equally from each other. The contact pads 2106 may be spaced so as to decrease the likelihood of shorting due to the presence of water droplets.

Figure 42:
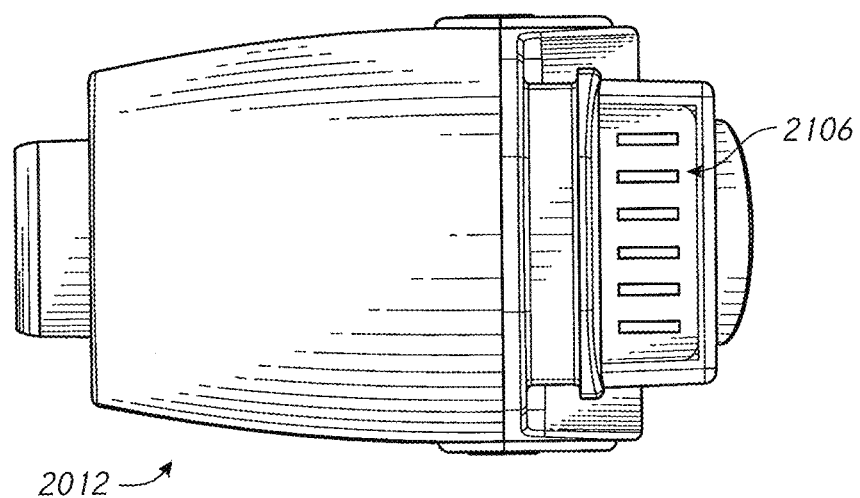
FIGS. 42 to 44 are a top views of example embodiments of a conduit connector, showing differently spaced and sized PCB contact pads.
Figure 43:
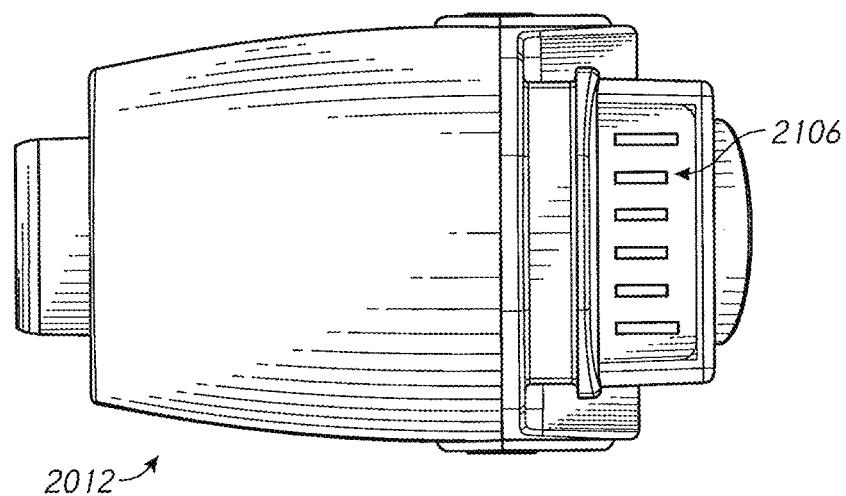
Figure 44:
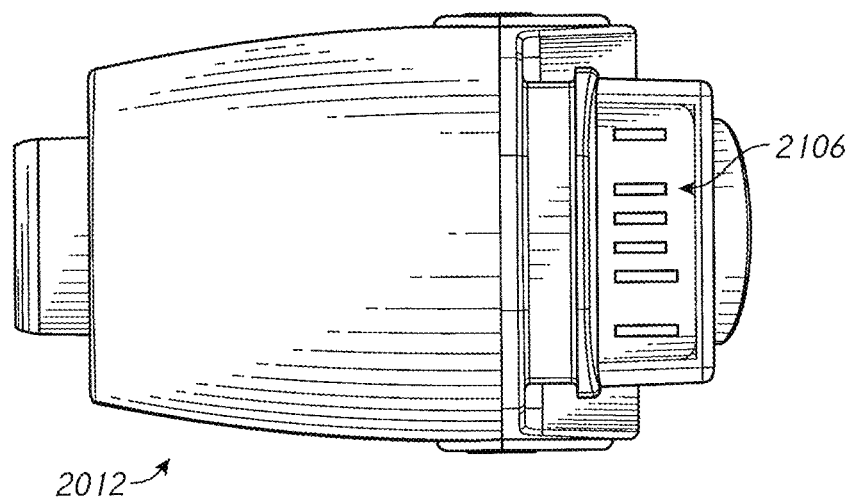

With reference now to FIGS. 42 to 44, example embodiments of the connector 2012 may have the contact pads 2106 sized, positioned, and spaced according to various designs. FIG. 42 shows an example embodiment of the conduit connector 2012, showing the contact pads 2106 uniformly sized and spaced, where the contact pads 2106 are positioned in the order of heater pad, identification pad, sensor pad, sensor pad, identification pad, heater pad (which can be designated HISSIH), each suited for connection to a corresponding wire. FIG. 43 shows an example embodiment of the conduit connector 2012, showing the contact pads 2106 uniformly spaced, and also in HISSIH order, but with longer heater pads that may help to ensure that the heater wire connections are made before, and broken after, the identification and sensor wire connections. FIG. 44 shows an example embodiment of the conduit connector 2012, with the contact pads 2106 also having longer heater pads, but with non-uniformly spaced pads in the order SSIIHH, from top to bottom, which increases the space between the sensor pads and the heater pads. In an embodiment, the first sensor pad (at the top, as illustrated in FIG. 44) is suited for connection to a positive sensor wire and the second sensor pad is suited for connection to a negative sensor wire, which helps to maximize the space between the positive sensor pad and the heater pads. Also, with reference to FIG. 45, an embodiment of the connector 2012 has the contact pads 2106 in the order SSIIHH, from top to bottom, with longer heater pads and a gap between the heater pads and the other pads, again helping to maximize the space between the heater pads and the sensor pads.

Figure 47:
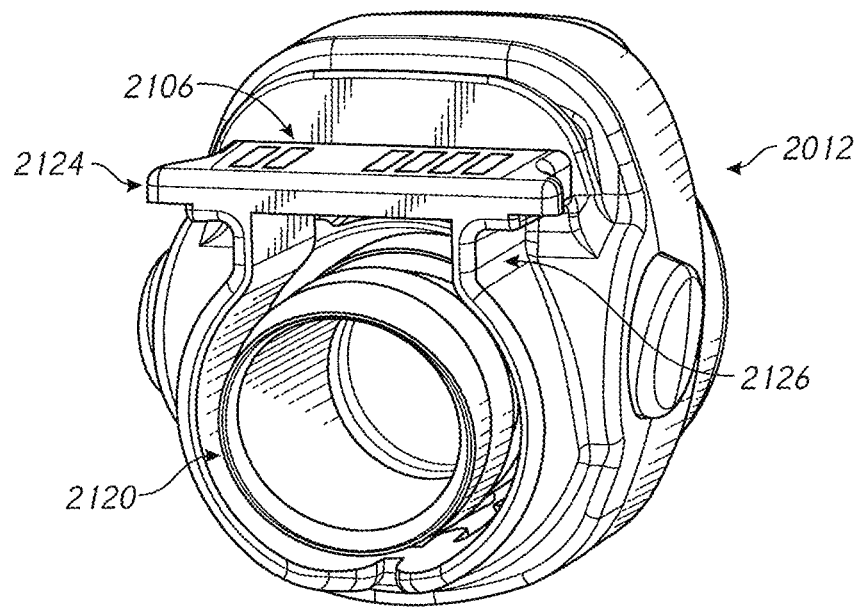
Figure 48:
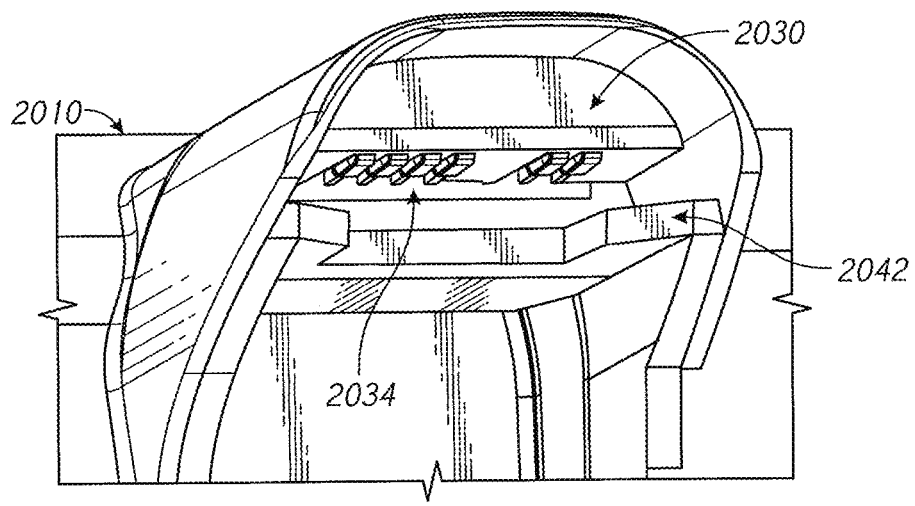
FIG. 48 illustrates a portion of another example embodiment of a cartridge.
Figure 49:
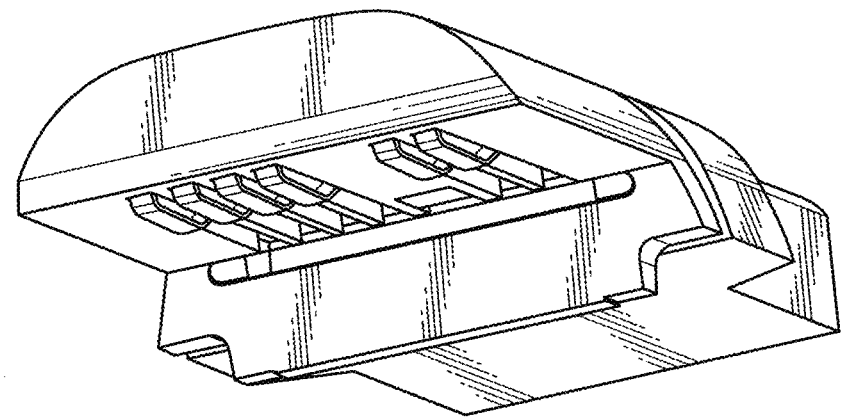
FIGS. 49 to 50 illustrate views of the insert block of FIG. 48.
Figure 50:
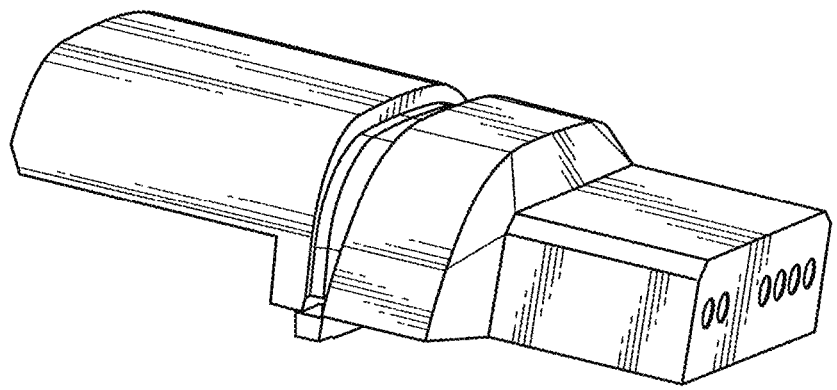

FIG. 48 illustrates a portion of an alternate embodiment of the cartridge 2010, showing the insert block 2030 with the electrical junction or contacts 2034 under the hood portion 2020. In this embodiment, the electrical contacts 2034 have spacing corresponding to the spacing of the contact pads 2106 of FIG. 47, in particular with a gap between the contacts that correspond to the heater pads and the contacts that correspond to the identification and sensor pads. FIGS. 49 and 50 provide additional views of the alternate embodiment of the insert block 2030 shown in FIG. 48.

With reference again to FIGS. 19 to 24, the inner plug 2100 may be retained within a cavity defined within a front cover 2110 and a back cover 2112. The front cover 2110 and the back cover 2112 may be coupled together or coupled to the inner plug 2100 to generally enclose the inner plug 2100 within the covers 2110, 2112. In the illustrated configuration, the back cover 2112 clips onto a portion of the inner plug 2100 and the front cover 2110, and the front cover 2110 also clips onto a portion of the inner plug 2100.

In some configurations, a seam between the front cover 2110 and the back cover 2112 is obscured by having at least a portion of one of the front cover 2110 and the back cover 2112 overlie a corresponding portion of the other of the two covers 2110, 2112. In the illustrated configuration, the front cover 2110 includes a recess 2114 over which a lip 2116 of the back cover 2112 slips. Thus, the lip 2116 obscures the seam between the two covers 2110, 2112 and an abutting relationship between the two covers 2110, 2112 reduces the likelihood of water infiltrating the connector 2012.

In the illustrated configuration, a locking ring 2118 may be secured between the front cover 2110 and the inner plug 2100. The locking ring 2118 includes the release buttons 2024. The release buttons 2024 protrude through openings 2120 provided in the front cover 2110 and/or the rear cover 2112. The locking ring 2118 is configured to latch onto a port of the chamber 2004 and the locking ring 2118 may be deflected by squeezing the release buttons 2024 toward each other, which allows for removal of the locking ring 2118 (and, therefore, the connector 2012) from the port of the chamber 2004.

With reference again to FIGS. 19 to 22, the illustrated front cover 2110 has a slightly different configuration from the configuration illustrated in FIG. 24. As illustrated in FIGS. 19 to 22, a distal end 2120 of the front cover 2110 may have a sloping face 2122. The sloping face 2122 may result from the top portion of the front cover 2110 extend further distally than the bottom portion of the front cover 2110. In some configurations, the sloping face 2122 is generally planar. In some configurations, the sloping face 2122 may be curvilinear. Other configurations are possible.

Figure 19:
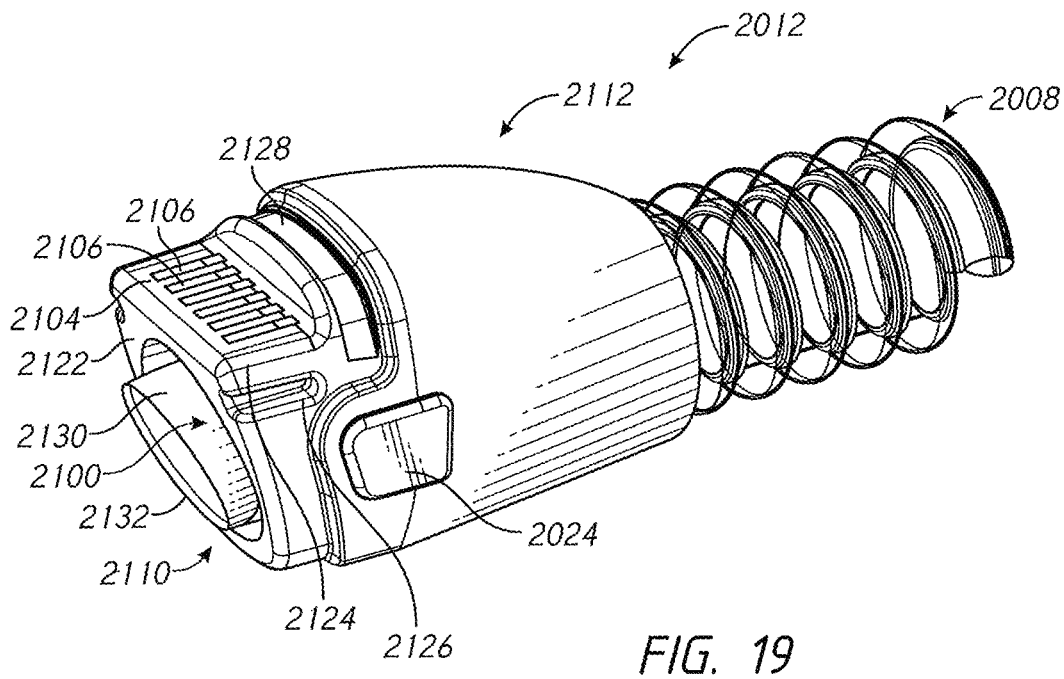
FIGS. 19 to 22 are views of the connector of FIG. 13.
Figure 20:
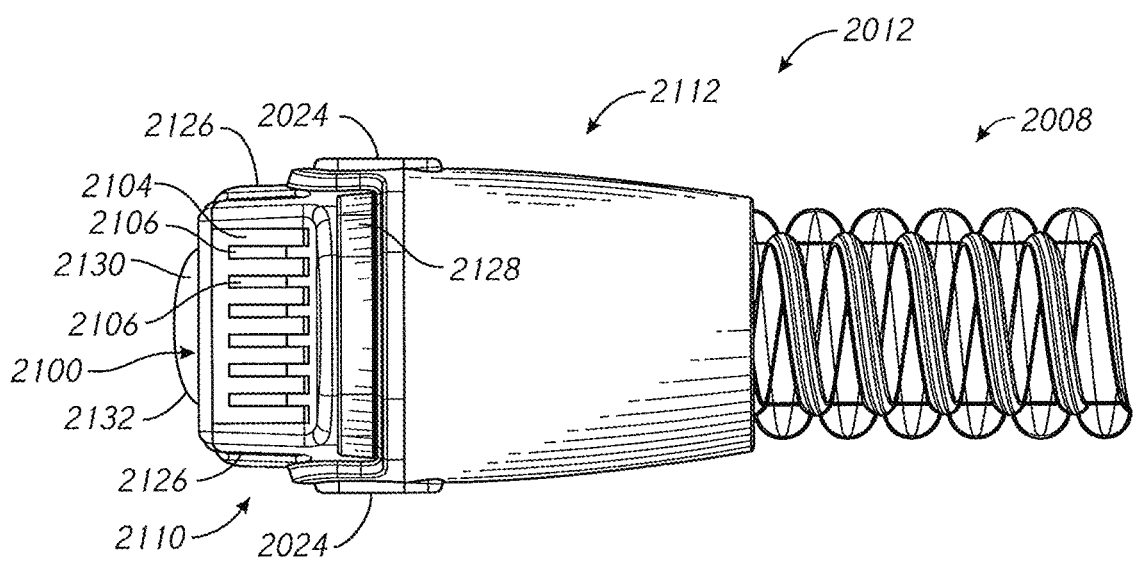
Figure 21:
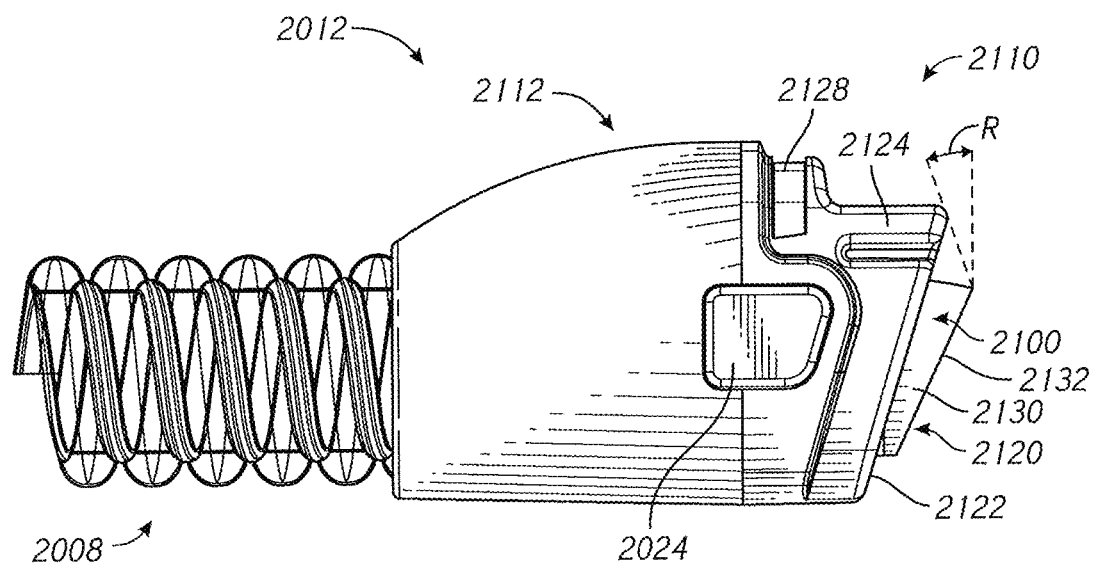
Figure 23:
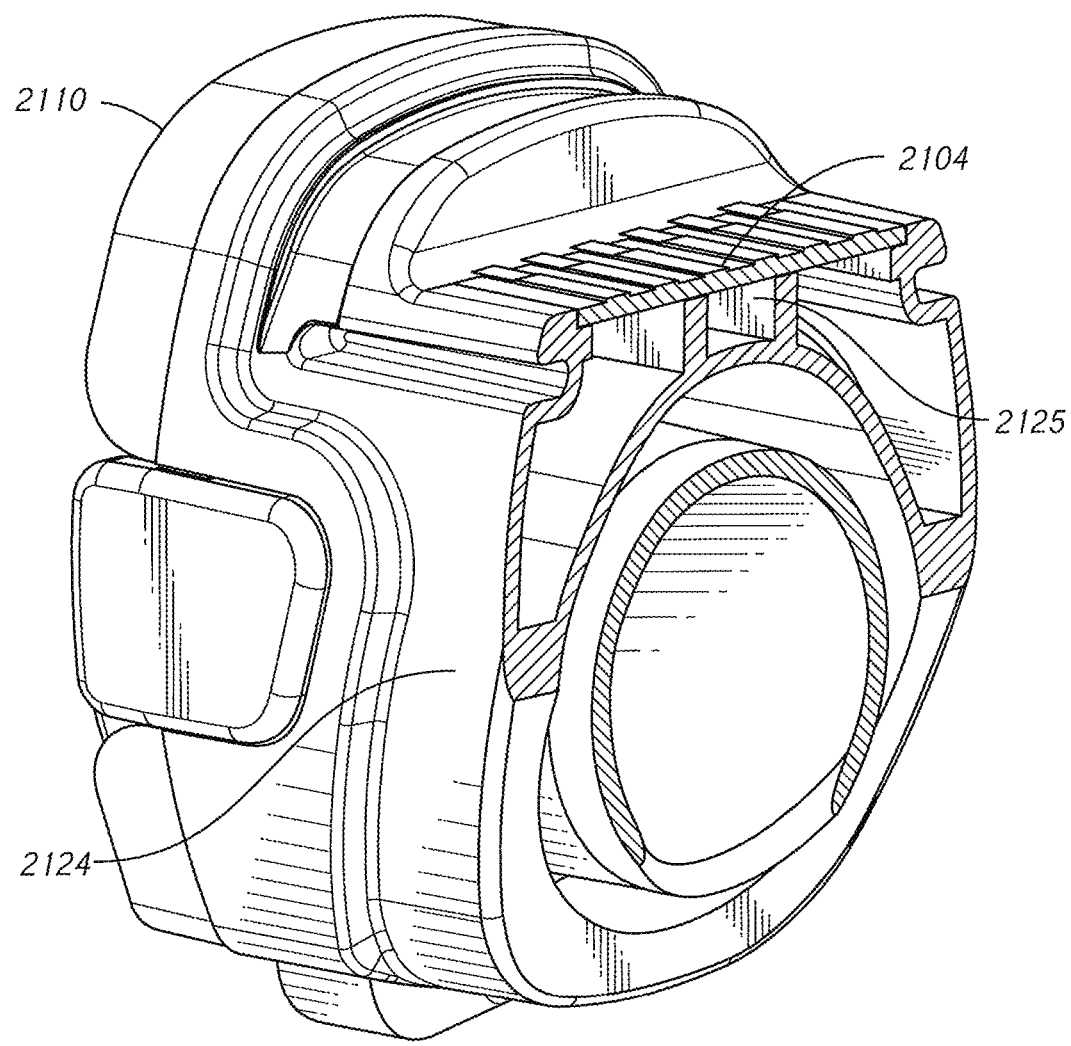
FIG. 23 is a sectional view of the connector of FIG. 13.

With reference to FIGS. 19, 21, and 23, the printed circuit board 2104 may be supported by the front cover 2110. In the illustrated configuration, the front cover 2110 incorporates a support region 2125 that may be generally surrounded by an outer surface 2124. The support region 2125 may underlie the printed circuit board 2104. The support region 2125 may provide support to the printed circuit board 2104 to reduce the likelihood of flexure or deflection of the printed circuit board 2104 during connection and use of the connector 2012. In the illustrated configuration (see FIG. 23), the support region may comprise one or more ribs or the like. In the illustrated configuration, the support region comprises a ledge that is formed around a rim that generally encircles the printed circuit board 2104. The illustrated ledge is recessed such that the printed circuit board 2104 is either recessed or flush with the surrounding portion of the front cover 2110. The one or more ribs may extend under a more central portion of the printed circuit board 2104 and may define supports for at least a central portion of the printed circuit board 2104. Any number of ribs may be used. In some configurations, other forms of support (bosses, plateaus or the like) may be used. In some configurations, no central supports are used.

Figure 22:
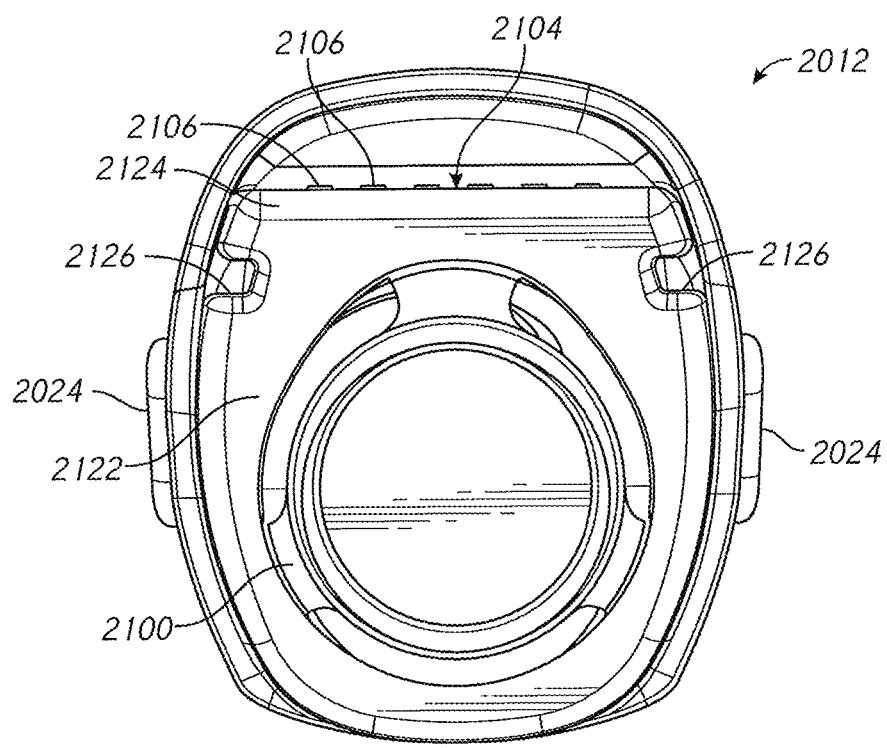

With reference to FIG. 22, the front cover 2110 also comprises at least one channel 2126. In the illustrated configuration, the front cover 2110 includes two channels 2126. The illustrated channels 2126 are generally diametrically opposed. The channels 2126 align with and receive the rails 2042 of the hood 2020. As such, the channels 2126 may help to align the connector 2012 during coupling with the cartridge 2010. The channels 2126 and the rails 2042 also help to resist vertical movement (e.g., up and down), twisting (e.g., rotation relative to the axis of the lumen) and yawing (e.g., rotation relative to an axis normal to the axis of the lumen) of the connector 2012 relative to the cartridge 2010 when the two are coupled together.

With reference again to FIG. 21, the front cover 2110 comprises a furrow 2128. The furrow 2128 extends over at least an upper portion of the front cover 2110. In the illustrated configuration, the furrow 2128 has a lateral expanse that is at least as great as the width of the printed circuit board 2104 (see FIG. 20). The furrow 2128 helps to divert away from the printed circuit board 2104 liquids that may be spilled onto the connector 2012. The furrow 2128 is thus proximal of the printed circuit board 2104 and may be recessed into the front cover 2110 such that at least a lip is defined between the furrow 2128 and the printed circuit board 2104. Other configurations are possible.

With reference to FIG. 21, the inner plug 2100 defines a lumen 2130. The lumen 2130 is in fluid communication with the conduit 2008. The lumen 2130 has a distal end 2132. The distal end 2132 has a non-normal configuration. In other words, the distal end 2132 is not simply squared off relative to an axis of the lumen 2130. In some configurations, the distal end 2132 is configured to complement the inner shape of a port of the humidification chamber 2004 within which it will be inserted. In some configurations, the distal end 2132 of the lumen 2130 will slope and extend as far into the port as possible to improve the ability of condensate to drain back into the humidification chamber 2004. This is most clearly shown in FIG. 15.

The distal end 2132 of the lumen 2130 has a sloping configuration. In the illustrated configuration, the distal end 2132 of the lumen 2130 slopes at a different slope relative to the sloping face 2122 of the front cover 2110. The top of the lumen 2130 projects further distally relative to the bottom of the lumen 2130. Moreover, the top of the lumen 2130 projects forward of a forwardmost portion of the sloping face 2122 of the front cover 2110. The top of the lumen 2130 projects further distally than any portion of the front cover 2110. In some configurations, the front cover 2110 projects distally of the bottom portion of the lumen 2130 but the top portion of the lumen 2130 projects further distally than the upper portion of the front cover 2110.

In some configurations, a recess angle R may be defined. The recess angle R may be the angle when viewed from the side between the upper portion of the front cover 2110 and the upper portion of the lumen 2130. The recess angle R may be 18 degrees in some configurations. It is believed that, if the recess angle R is greater than 18 degrees and if condensate is drained from the conduit 2008 with the connector 2012 upside down (i.e., with the printed circuit board 2104 horizontal and the contact pads 2106 facing the floor), the likelihood of condensate dripping back onto the printed circuit board 2104 is greatly reduced or eliminated.

Figure 45:
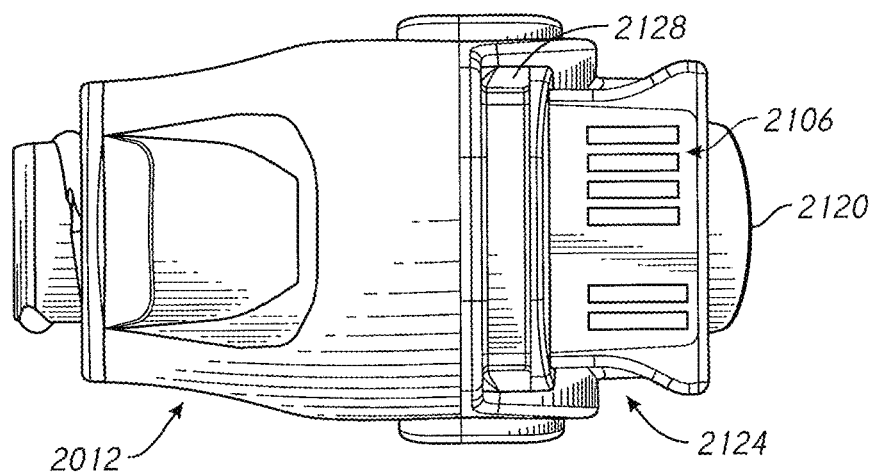
FIGS. 45 to 47 illustrate another example embodiment of a conduit connector.
Figure 46:
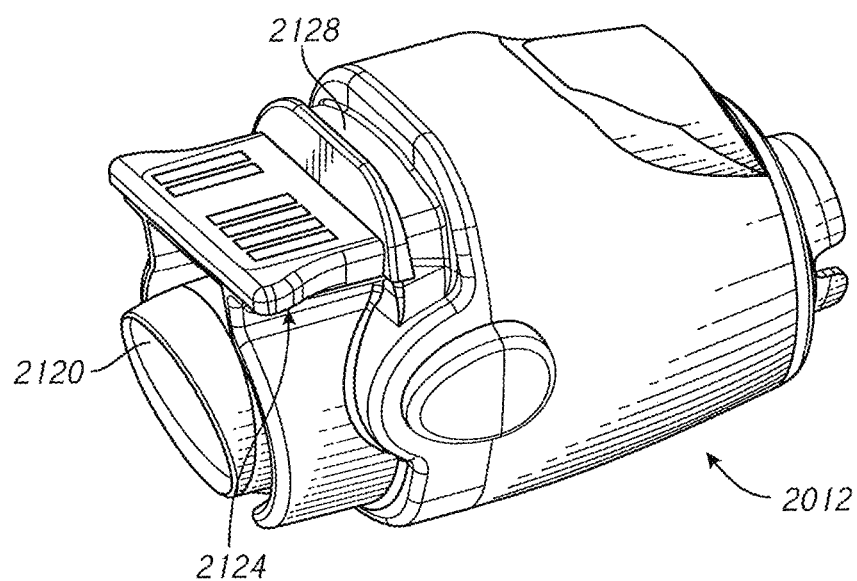

With reference to FIGS. 45 and 46, in an alternate embodiment of the connector 2012, the outer support surface 2124 may be flared, i.e., wider at the distal end 2120 than by the furrow 2128. This flaring helps to ensure that the channels 2126 are properly vertically aligned with the rails 2042 during insertion of the connector 2012 under the hood 2020.

Figure 25:
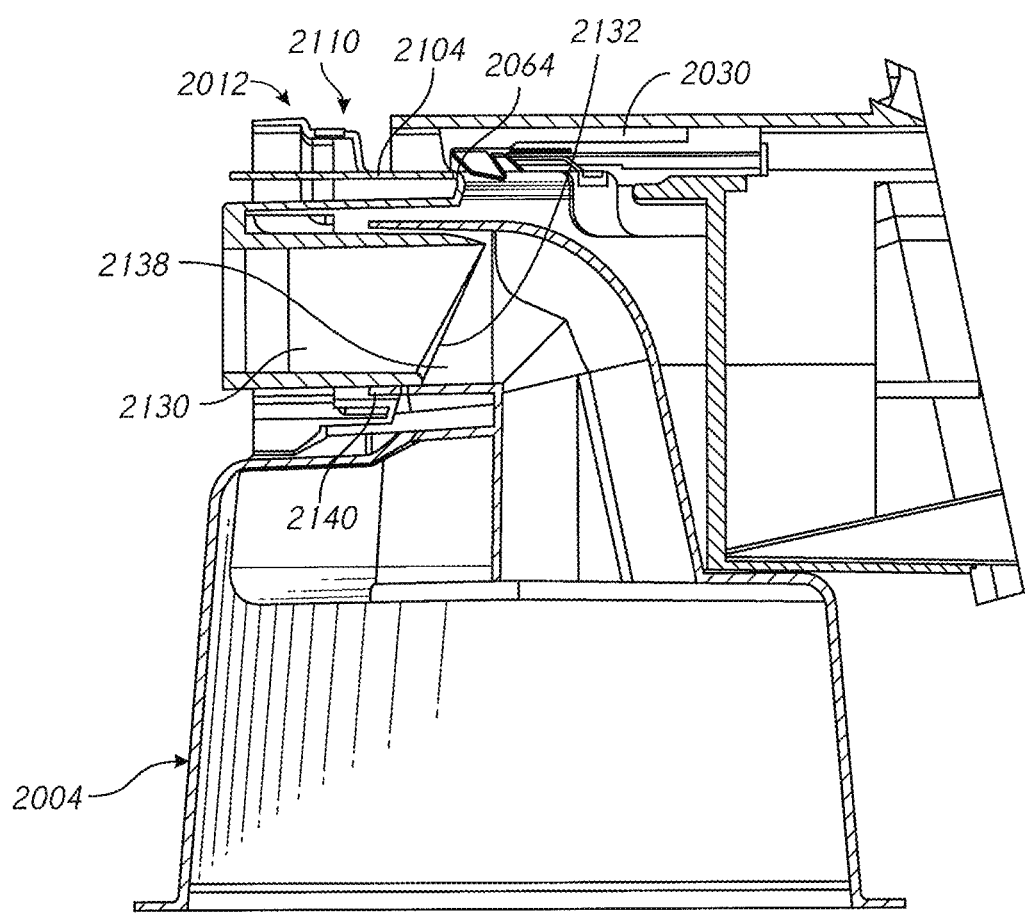
FIG. 25 is a sectional view of the chamber, cartridge, insert block, and a portion of the connector of FIG. 13.
Figure 26:
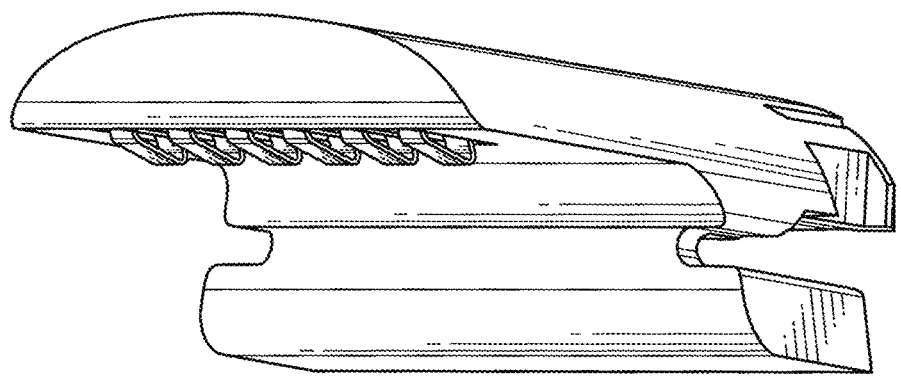
FIG. 26 is a front perspective view of another example embodiment of an insert block.
Figure 27:
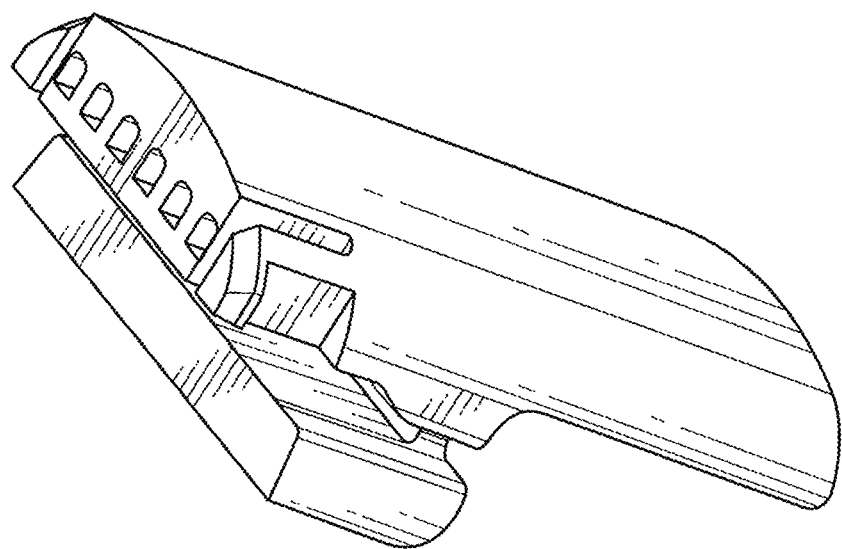
FIG. 27 is a rear perspective view of the insert block of FIG. 26, showing exit holes for wires.
Figure 28:
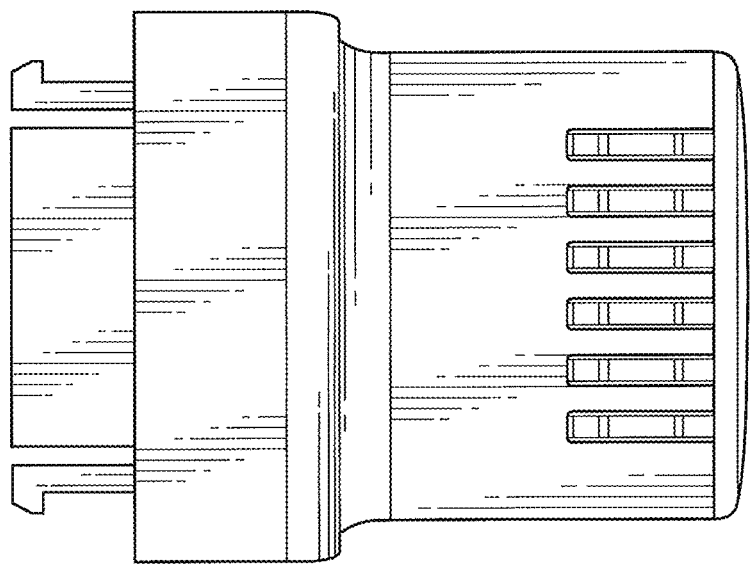
FIG. 28 is a bottom view of the insert block of FIG. 26.
Figure 29:
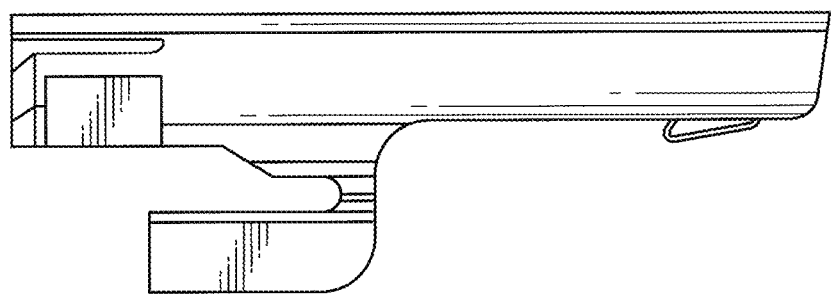
FIG. 29 is a side view of the insert block of FIG. 26.
Figure 30:
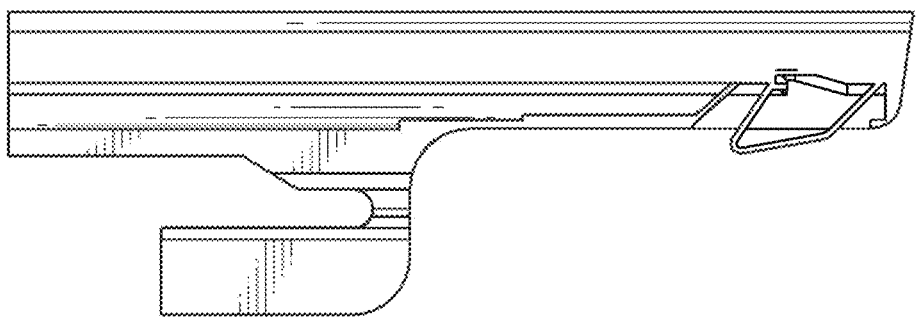
FIG. 30 is a sectional side view of the insert block of FIG. 26.
Figure 31:
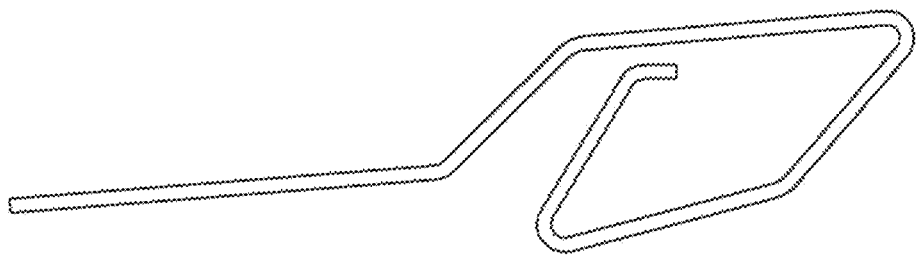
FIG. 31 is a detailed image of a rotating leaf pin used in the insert block of FIG. 26.
Figure 32:
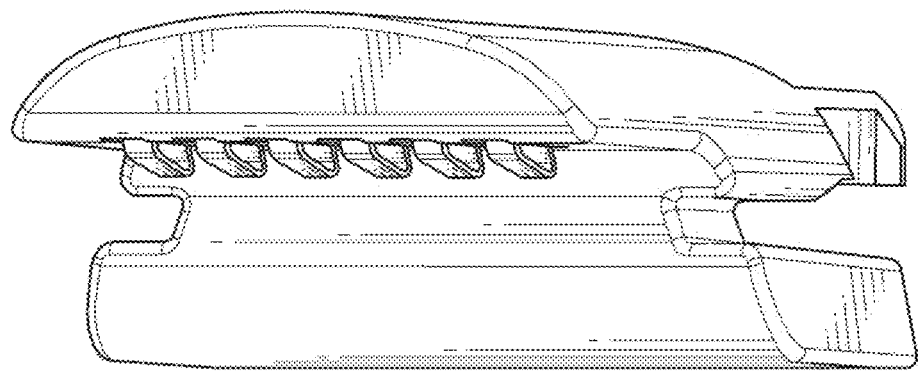
FIG. 32 is a front perspective view of another example embodiment of an insert block.
Figure 33:
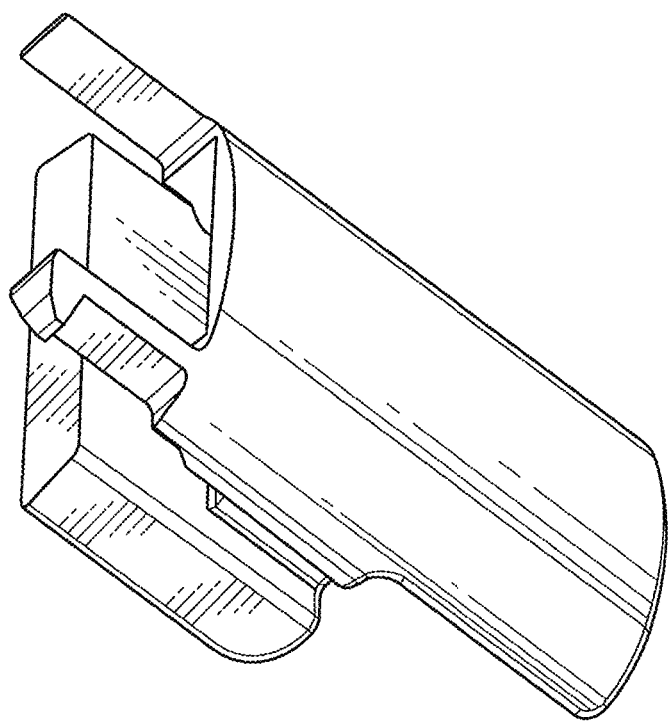
FIG. 33 is a rear perspective view of the insert block of FIG. 32.
Figure 34:
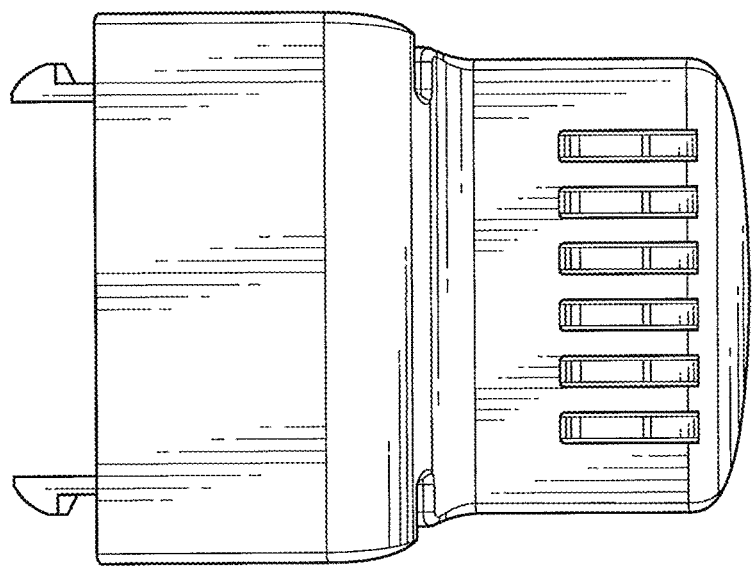
FIG. 34 is a bottom view of the insert block of FIG. 32.
Figure 35:
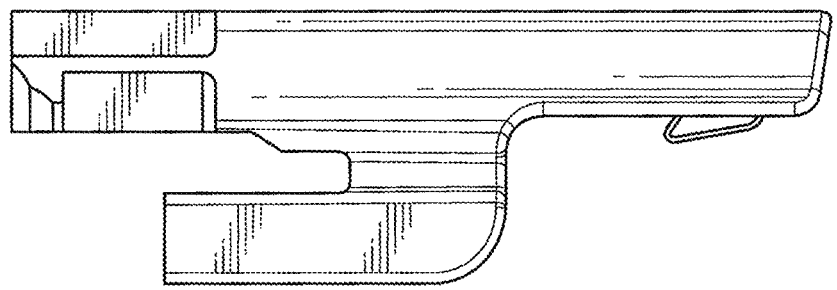
FIG. 35 is a side view of the insert block of FIG. 32.
Figure 36:
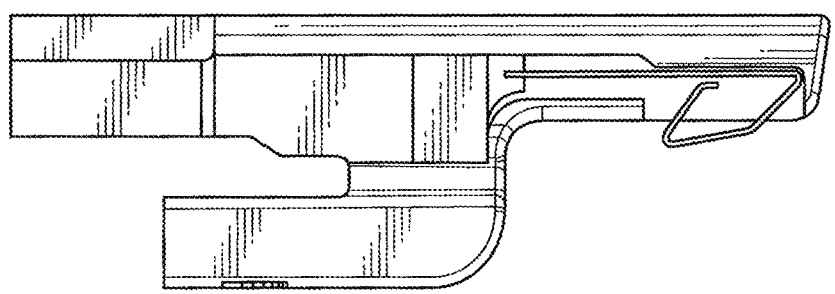
FIG. 36 is a sectional side view of the insert block of FIG. 32.
Figure 37:
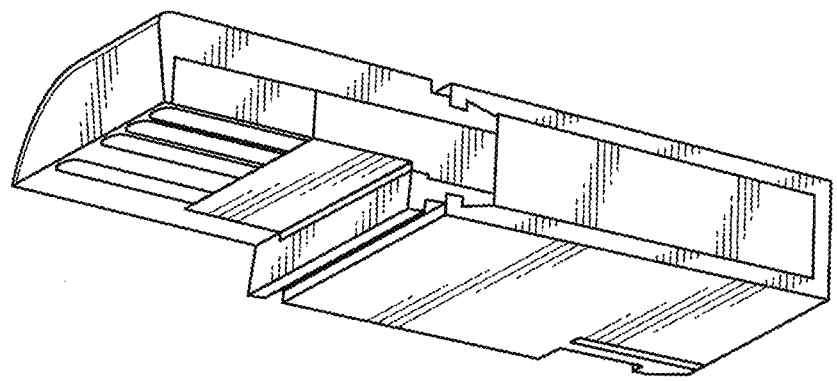
FIG. 37 is a perspective view of an example embodiment of an insert block formed of multiple pieces, in which one or more of the pieces may be overmoulded.
Figure 38:
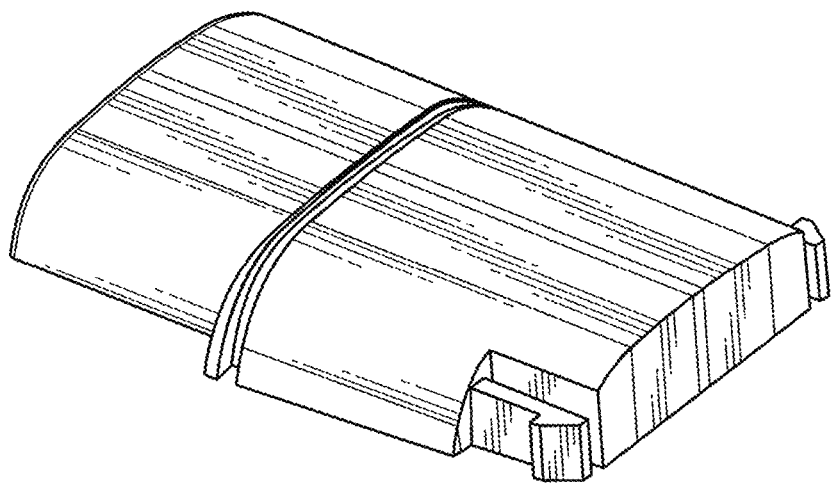
FIG. 38 is another perspective view of the insert block of FIG. 37.
Figure 39:
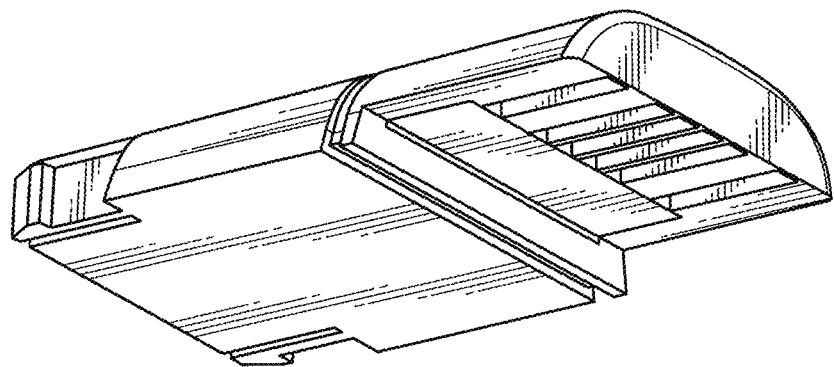
FIG. 39 is another perspective view of the insert block of FIG. 38.
Figure 40:
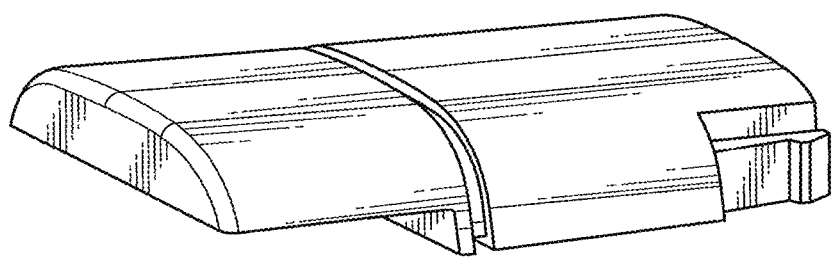
FIG. 40 is another perspective view of the insert block of FIG. 39.
Figure 41:
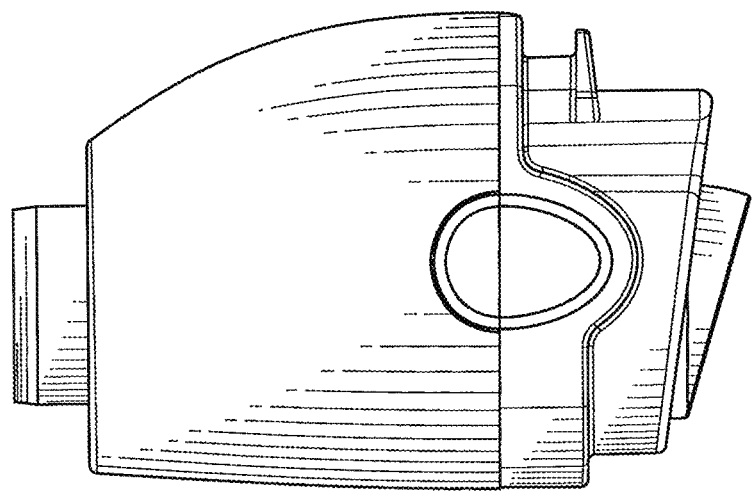
FIG. 41 is a side view of another example embodiment of a conduit connector.

With reference to FIG. 25, the chamber 2004 includes a port 2138. The port 2138 terminates in an opening 2140. As illustrated, the distal end 2132 of the lumen 2130 is well within the port 2138 at the time the printed circuit board 2104 approaches contact with the terminals 2064 of the insert block 2030. As such, in the illustrated configurations, during decoupling of the connector 2012 from the cartridge 2010 and the port 2138, the electrical connection between the printed circuit board 2104 and the insert block 2030 will break before the pneumatic connection between the lumen 2130 and the port 2138 will break. In other words, the electrical connection breaks before the pneumatic connection. Similarly, during coupling of the connector 2012 with the cartridge 2010 and the port 2138, the pneumatic connection will be established before the electrical connection. More particularly, the lumen 2130 and the port 2138 will mate before the terminals 2064 contact the pads 2106 of the printed circuit board 2104.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, some structures described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A coupler for a humidification system, the coupler comprising:
    a plurality of electrical contact terminals, the plurality of electrical contact terminals being located on a downward facing surface of an extension portion such that the extension portion reduces a likelihood of spilled liquid contacting the plurality of electrical contact terminals during use, the coupler being configured to removably connect to a humidification system base unit and a circuit connector of a breathing tube, the extension portion extending outwardly relative to the humidification system base unit when the coupler is connected to the humidification system base unit, and the plurality of electrical contact terminals being complementary to electrical contacts of the circuit connector of the breathing tube.

2. The coupler of claim 1, wherein the extension portion comprises a hood or shroud portion extending in a forward, horizontal direction relative to the humidification system base unit when the coupler is connected to the humidification system base unit, the plurality of electrical contact terminals being positioned on an underside of the hood or shroud portion.

3. The coupler of claim 1, wherein the plurality of electrical contact terminals are sprung terminals.

4. The coupler of claim 1, wherein the plurality of electrical contact terminals are bent backwards.

5. The coupler of claim 1, wherein:
    the plurality of electrical contact terminals protrude downward beyond the downward facing surface; and/or
    the downward facing surface is configured to contact an upper contact surface of the circuit connector; and/or
    the downward facing surface is substantially planar.

6. The coupler of claim 1, wherein the plurality of electrical contact terminals and the downward facing surface are disposed on an insert block.

7. The coupler of claim 6, wherein the coupler further comprises a hood or shroud portion, wherein the insert block is configured to be received and/or retained within the hood or shroud portion, the hood or shroud portion substantially covering the insert block when the insert block is positioned within the hood or shroud portion.

8. The coupler of claim 7, wherein the insert block is configured to be slidably inserted into the hood or shroud portion in a proximal direction relative to the humidification system base unit.

9. The coupler of claim 7, further comprising a flange, wherein the insert block comprises a recess that is configured to receive at least a portion of the flange when the insert block is received and/or retained in the hood or shroud portion.

10. The coupler of claim 7, wherein the hood or shroud portion comprises one or more alignment features configured to guide insertion of the insert block and/or insertion of the circuit connector such that the circuit connector is brought into engagement with the humidification system base unit.

11. The coupler of claim 10, wherein the one or more alignment features comprise a first rail on a first side of the hood or shroud portion and a second rail on a second side of the hood or shroud portion.

12. The coupler of claim 10, wherein the insert block comprises one or more channels that are configured to receive the one or more alignment features.

13. The coupler of claim 12, wherein a length of the one or more channels is shorter than a length of the one or more alignment features.

14. The coupler of claim 7, wherein the insert block further comprises one or more deflectable tabs, each having a catch element.

15. The coupler of claim 14, wherein the one or more deflectable tabs and/or the catch element are configured to deflect inwardly during insertion of the insert block into the hood or shroud portion and to deflect outwardly to secure the insert block into the hood or shroud portion, thereby forming a releasable and lockable connection between the insert block and the humidification system base unit.

16. A humidification system base unit for a humidification system, the humidification system base unit comprising:
    a heater plate; and
    a coupler according to claim 1 configured to connect the circuit connector to the humidification system base unit.

17. The humidification system base unit of claim 16, wherein the humidification system base unit is configured to operatively connect in use to a humidification chamber.

18. The humidification system base unit of claim 17, wherein the humidification system base unit comprises the humidification chamber.

19. The humidification system base unit of claim 16, wherein the coupler electrically and/or structurally couples to the humidification system base unit.

20. The humidification system base unit of claim 16, wherein the coupler electrically and/or structurally couples to the circuit connector.

* * * * *